United States Patent
Zhang et al.

(10) Patent No.: US 8,501,755 B2
(45) Date of Patent: Aug. 6, 2013

(54) TETRAHYDROPYRIDOTHIENOPYRIMIDINE COMPOUNDS AND METHODS OF USE THEREOF

(75) Inventors: Chengzhi Zhang, San Diego, CA (US); Kanwar Sidhu, Orange, CT (US); Mario Lobell, Wuppertal (DE); Gaetan Ladouceur, Rockville, MD (US); Qian Zhao, Wallingford, CT (US); Zheng Liu, Beacon Falls, CT (US); Kristen M. Allegue, Rocky Hill, CT (US); Chetan P. Darne, Orange, CT (US); Jason Newcom, Northford, CT (US)

(73) Assignee: Bayer Intellectual Property GmbH, Monheim (DE)

( * ) Notice: Subject to any disclaimer, the term of this patent is extended or adjusted under 35 U.S.C. 154(b) by 598 days.

(21) Appl. No.: 12/225,285

(22) PCT Filed: Mar. 20, 2007

(86) PCT No.: PCT/US2007/006927
§ 371 (c)(1),
(2), (4) Date: Aug. 9, 2010

(87) PCT Pub. No.: WO2007/109279
PCT Pub. Date: Sep. 27, 2007

(65) Prior Publication Data
US 2010/0298297 A1   Nov. 25, 2010

Related U.S. Application Data

(60) Provisional application No. 60/784,146, filed on Mar. 20, 2006.

(51) Int. Cl.
*A61K 31/519* (2006.01)
*C07D 471/14* (2006.01)

(52) U.S. Cl.
USPC .......................................... 514/267; 544/250

(58) Field of Classification Search
USPC .......................................... 514/267; 544/250
See application file for complete search history.

(56) References Cited

U.S. PATENT DOCUMENTS 6,482,948 B1   11/2002   Yamada et al.
2003/0236271 A1   12/2003   Hayakawa et al.

FOREIGN PATENT DOCUMENTS

| CA | 2387520 | | 3/2001 |
|---|---|---|---|
| WO | WO03/035653 | * | 5/2003 |
| WO | WO-2005/010008 | | 2/2005 |

OTHER PUBLICATIONS

Golub et al, 1999, Science, vol. 286, p. 531-537.*
Targeted Cancer Therapies, http://www.cancer.gov/cancertopics/factsheet/therapy/targeted, accessed Jan. 12, 2011.*
Voskoglou-Nomikos, 2003, Clinical Cancer Research, vol. 9, p. 4227-4239.*
Pech, R. et al.:"Uber Thienoverbindungen 11. Mitteilung: Darstellung 4-Aminosubstituierterthieno2,3-Dpyrimidin-2-Ylcarbonsaeurederivate," Pharmazie, Die, Govi Verlag, Eschborn, Germany, vol. 46, No. 6, 1991 pp. 422-423.

* cited by examiner

*Primary Examiner* — Wu-Cheng Winston Shen
*Assistant Examiner* — Karen Cheng

(57) ABSTRACT

This invention relates to compounds of Formula (I),

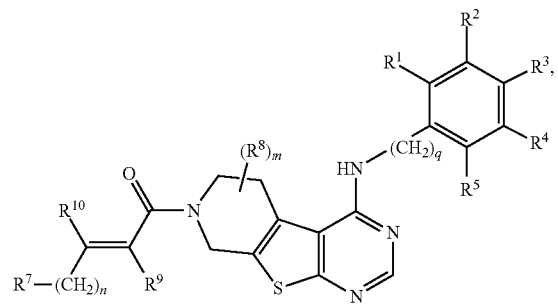

wherein the variables are as disclosed in the specification, to pharmaceutical compositions containing them, to methods of making the compounds and pharmaceutical compositions, and to methods of using the compounds and pharmaceutical compositions for treating or preventing disorders, in particular cancer.

21 Claims, No Drawings

TETRAHYDROPYRIDOTHIENOPYRIMIDINE COMPOUNDS AND METHODS OF USE THEREOF

RELATED APPLICATIONS/PATENTS AND INCORPORATION BY REFERENCE

This application is a National Stage Application filed under 35 U.S.C. §371 based on International Application No. PCT/US2007/006927, filed Mar. 20, 2007, which claims priority to U.S. Provisional Patent Application No. 60/784,146, filed Mar. 20, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

FIELD OF THE INVENTION

This invention relates to novel compounds and processes for their preparation, methods of treating diseases, particularly cancer, comprising administering said compounds, and methods of making pharmaceutical compositions for the treatment or prevention of disorders, particularly cancer.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were expected in 2005. The majority of these new cases will be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005).

Cancer treatments are of two major types, either curative or palliative. The main curative therapies for cancer are surgery and radiation. These options are generally successful only if the cancer is found at an early localized stage. Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common.

Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA interchalators that interfere with DNA polymerase and Topoisomerase II (e.g. doxorubicin, epirubicin); and the non-anthracycline inhibitors of Topoisomerase II and I enzymatic activity (e.g. topotecan, irinotecan, and etoposide). Even though different cytotoxic drugs act via different mechanisms of action, each generally leads to at least transient shrinkage of tumors.

Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification (e.g. histone deacetylase (HDAC)), inhibition of proteins involved in microtubule movement and cell cycle progression (e.g. kinesins, aurora kinase), and novel inducers of the apoptotic pathway (e.g. bcl-2 inhibitors).

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

In addition to direct inhibition of tumor cell targets, cytostatic drugs are being developed to block the process of tumor angiogenesis. This process supplies the tumor with existing and new blood vessels to support continued nourishment and therefore help promote tumor growth. Key tyrosine kinase receptors including Vascular Endothelial Growth Factor Receptor 2 (VEGFR2), Fibroblast Growth Factor 1 (FGFR1) and Tie2 have been shown to regulate angiogenesis and have emerged as highly attractive drug targets.

Several new drugs that are directed at various molecular targets have been approved over the past five years for the treatment of cancer. Imatinib is an inhibitor of the Abl tyrosine kinase and was the first small molecule tyrosine kinase inhibitor to be approved for the treatment of chronic myeloid leukemia (CML). Based on additional activity of imatinib against the receptor tyrosine kinase activated in gastrointestinal stromal tumors (GIST), c-KIT, it was subsequently approved for the treatment of advanced GIST. Erlotinib, a small molecule inhibitor of EGFR, was approved in late 2004 for the treatment of non-small cell lung carcinoma (NSCLC). Sorafenib, an inhibitor of multiple kinases including c-Raf and VEGFR2 was approved for the treatment of advanced renal cell carcinoma (RCC) in December, 2005. Recently in January of 2006, Sunitinib, a multi-kinase inhibitor was approved for the treatment of refractory- or resistant-GIST and advanced RCC. These small molecule inhibitors demonstrate that targeted approaches are successful for the treatment of different types of cancers.

SUMMARY OF THE INVENTION

In one aspect, the invention provides a compound of formula (I)

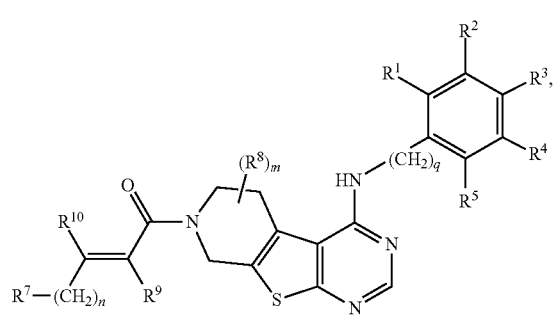

(I)

in which
m is 0, 1, or 2;
n is 0, 1, 2, or 3;
q is 0 or 1;
$R^1$ represents H, $(C_1-C_4)$alkyl, or halo;
$R^2$ is selected from the group consisting of H, —CN, halo, $(C_1-C_4)$alkyl, —O$(C_1-C_4)$alkyl, $(C_2-C_4)$alkenyl, and $(C_2-C_4)$alkynyl;
$R^3$ is selected from the group consisting of H, halo, —CN, $(C_1-C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1-C_4)$alkyl and halo; or
$R^2$ and $R^3$ may be joined, and taken together with the carbon atoms to which they are attached, form a fused five- or six-membered saturated or unsaturated carbocycle, or form a fused heterocycle in which the combined $R^2$ and $R^3$ groups are represented by the formula

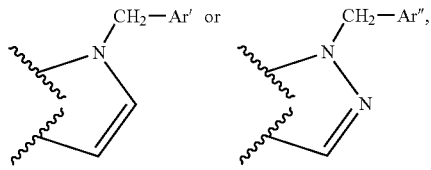

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;

$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;
$R^5$ represents H or halo;
when n is 0, $R^7$ is H;
when n is 1, 2 or 3, $R^7$ represents:
H;
hydroxyl;
—NR$^{12}$R$^{13}$ wherein
$R^{12}$ represents H or $(C_1-C_6)$alkyl which optionally bears 1 or 2 hydroxyl or mono- or di-($(C_1-C_4)$alkyl) amino groups; and
$R^{13}$ represents H, $(C_1-C_6)$alkyl, or $(C_3-C_6)$cycloalkyl, said alkyl and cycloalkyl groups optionally bearing 1 or 2 hydroxyl or mono- or di-($(C_1-C_4)$alkyl) amino groups;

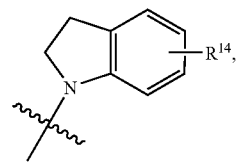

in which $R^{14}$ is hydroxyl, $(C_1-C_4)$alkyl, $(C_1-C_4)$alkoxy, or mono- or di-($(C_1-C_4)$alkyl)amino, each alkyl substituent in turn optionally bearing a hydroxyl substituent;

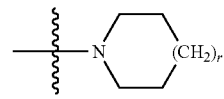

which optionally bears 1 or 2 hydroxyl, $(C_1-C_4)$alkyl, $(C_1-C_4)$alkoxy, or mono- or di-($(C_1-C_4)$alkyl)amino substituents, each alkyl substituent in turn optionally bearing a hydroxyl substituent; and wherein r is 0, 1, or 2;

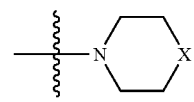

which optionally bears 1 or 2 $(C_1-C_4)$alkyl substituents, each alkyl substituent in turn optionally bearing a hydroxyl substituent; and wherein
X represents O, S(O)$_s$, or NR$^{15}$, in which s is 0, 1 or 2; and
$R^{15}$ represents $(C_1-C_4)$alkyl;

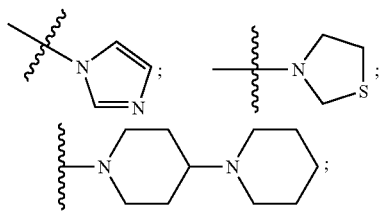

or
when n=2, $R^7$ and $R^9$ may be joined, and taken together with the carbon atoms to which they are attached and the intervening carbon atoms, form a ring of structure

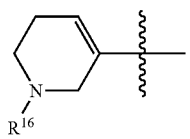

wherein $R^{16}$ represents $(C_1\text{-}C_4)$alkyl;
$R^8$ represents halo, hydroxyl, or $(C_1\text{-}C_4)$alkyl;
$R^9$ represents H or —$CH_2$—Y, wherein Y is mono- or di-$((C_1\text{-}C_4)$alkyl$)$amino, or

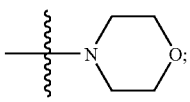 [SMILES: *N1CCOCC1]

$R^{10}$ represents H;
or
$R^9$ and $R^{10}$ may be taken together to form a bond, resulting in an acetylenic linkage;
or a pharmaceutically acceptable salt thereof.

In certain embodiments, m is 0. In certain embodiments, n is 1. In certain embodiments, q is 0.

In certain embodiments, $R^1$ is hydrogen or fluoro; $R^2$ is selected from the group consisting of H, —CN, halo, $(C_1\text{-}C_4)$alkyl, and $(C_2\text{-}C_4)$alkynyl; $R^3$ is selected from the group consisting of H, halo, and *—$O(CH_2)_p$Ar, wherein Ar is phenyl, pyridyl, or pyrazinyl, and wherein Ar can optionally be substituted with 1 or 2 halogens, and wherein p is 0 or 1; $R^4$ is selected from the group consisting of H, —CN, and halo; $R^5$ is hydrogen; and $R^7$ is —$NR^{12}R^{13}$ wherein $R^{12}$ represents H or $(C_1\text{-}C_6)$alkyl, and $R^{13}$ represents H or $(C_1\text{-}C_6)$alkyl.

In certain embodiments, $R^1$ is H; $R^2$ is selected from the group consisting of H, halo, and ethynyl; $R^3$ is selected from the group consisting of H, halo, —CN, methyl, and *—O$(CH_2)_p$Ar, wherein Ar is phenyl, pyridyl, or pyrazinyl, and wherein Ar can alternatively be substituted with 0, 1 or 2 halogens, and wherein p is 0 or 1; $R^4$ is selected from the group consisting of H, halo, and $(C_1\text{-}C_4)$alkyl; $R^5$ is hydrogen; and $R^7$ is a mono- or di-$((C_1\text{-}C_4)$alkyl$)$amino group. In certain embodiments, $R^2$ is ethynyl; $R^3$ is selected from the group consisting of H, halo, and *—$O(CH_2)_p$Ar, wherein Ar is phenyl, pyridyl, or pyrazinyl, and wherein Ar can alternatively be substituted with 0, 1 or 2 halogens, and wherein p is 0 or 1; and $R^4$ is hydrogen.

In certain embodiments, $R^2$ is halo; and $R^3$ is selected from the group consisting of H, halo, and *—$O(CH_2)_p$Ar, wherein Ar is phenyl, pyridyl, or pyrazinyl, and wherein Ar can alternatively be substituted with 0, 1 or 2 halogens, and wherein p is 0 or 1. In certain embodiments, $R^3$ is halo.

In another aspect, the invention provides a compound selected from the group consisting of: N-[3-chloro-4-(pyridin-2-ylmethoxy)phenyl]-7-[(2E)-4-(diethylamino)but-2-enoyl]-5,6,7,8-tetrahydropyrido[4',3':4,5]thieno[2,3-d]pyrimidin-4-amine; N-[3-chloro-4-(pyridin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine; N-(3-chloro-4-fluorophenyl)-7-[(2E)-4-(dimethylamino)but-2-enoyl]-5,6,7,8-tetrahydropyrido[4',3':4,5]thieno[2,3-d]pyrimidin-4-amine; N-(3-chloro-4-fluorophenyl)-7-[(2E)-4-(diethylamino)but-2-enoyl]-5,6,7,8-tetrahydropyrido[4',3':4,5]thieno[2,3-d]pyrimidin-4-amine; 7-[(2E)-4-(diethylamino)but-2-enoyl]-N-(3-ethynylphenyl)-5,6,7,8-tetrahydropyrido[4',3':4,5]thieno[2,3-d]pyrimidin-4-amine; 7-[(2E)-4-(dimethylamino)but-2-enoyl]-N-(3-ethynylphenyl)-5,6,7,8-tetrahydropyrido[4',3':4,5]thieno[2,3-d]pyrimidin-4-amine; N-(3-chloro-4-fluorophenyl)-7-{(2E)-4-[isopropyl(methyl)amino]but-2-enoyl}-5,6,7,8-tetrahydropyrido[4',3':4,5]thieno[2,3-d]pyrimidin-4-amine; N-(3-chloro-4-fluorophenyl)-7-{(2E)-4-[ethyl(isopropyl)amino]but-2-enoyl}-5,6,7,8-tetrahydropyrido[4',3':4,5]thieno[2,3-d]pyrimidin-4-amine; N-(3,4-dichlorophenyl)-7-[(2E)-4-(dimethylamino)but-2-enoyl]-5,6,7,8-tetrahydropyrido[4',3':4,5]thieno[2,3-d]pyrimidin-4-amine; and N-(3,4-dichlorophenyl)-7-{(2E)-4-[isopropyl(methyl)amino]but-2-enoyl}-5,6,7,8-tetrahydropyrido[4',3':4,5]thieno[2,3-d]pyrimidin-4-amine.

In another aspect, the invention provides a process for preparing a compound of Formula (I), comprising
(i) reacting a compound of formula (7)

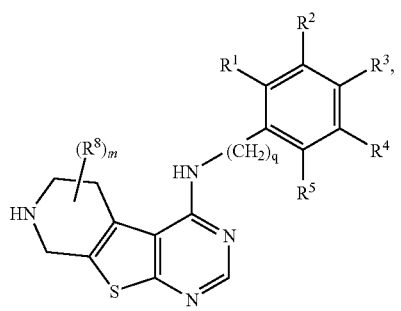

wherein $R^1$ to $R^5$, $R^8$, m and q have the meanings indicated above, with a compound of formula (10)

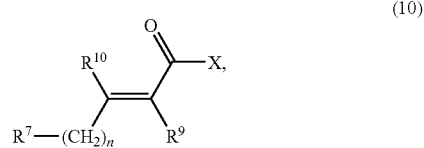

wherein $R^7$, $R^9$ and $R^{10}$ and n have the meanings indicated above, and X is hydroxy, chloro or bromo; or
(ii) reacting a compound of formula (9)

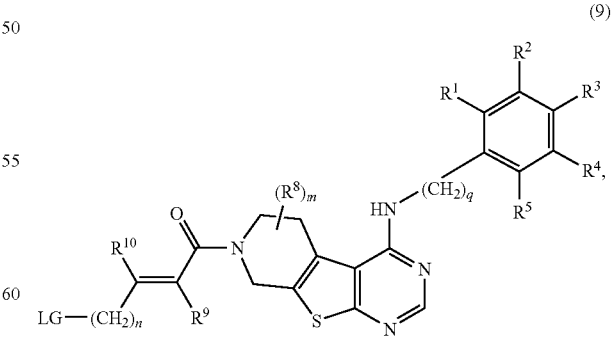

wherein $R^1$ to $R^5$, $R^8$ to $R^{10}$, m, n and q have the meanings indicated above, and LG is a leaving group, with a compound of formula $R^7$—H, wherein $R^7$ has the meaning indicated above; or (iii) reacting a compound of the formula (14):

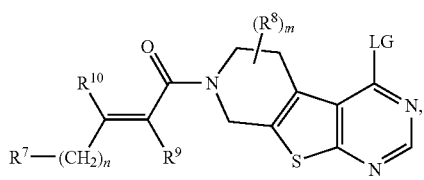

(14)

wherein $R^7$-$R^{10}$, m and n have the meanings indicated above, and LG is a leaving group, with a compound of the formula (15):

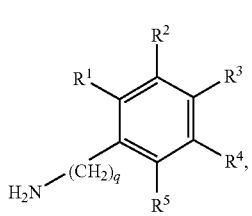

(15)

wherein $R^1$ to $R^5$, n and q have the meanings indicated above, and LG is a leaving group, under conditions such that a compound of Formula (I) is prepared.

In another aspect, the invention provides a pharmaceutical composition comprising a compound as defined above, together with a pharmaceutically acceptable carrier. In certain embodiments, the pharmaceutical composition is provided in a form suitable for intravenous administration.

In still another aspect, the invention provides a process for preparing a pharmaceutical composition. The process includes the step of comprising combining at least one compound as defined above with at least one pharmaceutically acceptable carrier, and bringing the resulting combination into a suitable administration form.

In still another aspect, the invention provides use of a compound as defined above for manufacturing a pharmaceutical composition for the treatment or prevention of a cell proliferative disorder. In certain embodiments, the cell proliferative disorder is cancer.

In yet another aspect, the invention provides a compound of formula (7)

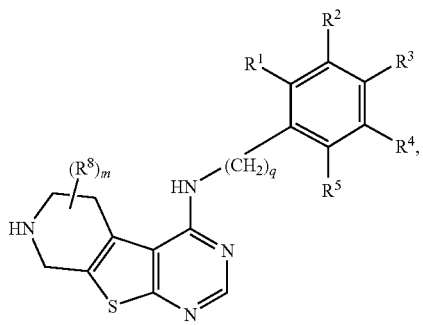

(7)

wherein
m is 0, 1, or 2;
q is 0 or 1;
$R^1$ represents H, $(C_1$-$C_4)$alkyl, or halo;

$R^2$ is selected from the group consisting of H, —CN, halo, $(C_1$-$C_4)$alkyl, —O$(C_1$-$C_4)$alkyl, $(C_2$-$C_4)$alkenyl, and $(C_2$-$C_4)$alkynyl;
$R^3$ is selected from the group consisting of H, halo, —CN, $(C_1$-$C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1$-$C_4)$alkyl and halo; or
$R^2$ and $R^3$ may be joined, and taken together with the carbon atoms to which they are attached, form a fused five- or six-membered saturated or unsaturated carbocycle, or form a fused heterocycle in which the combined $R^2$ and $R^3$ groups are represented by the formula

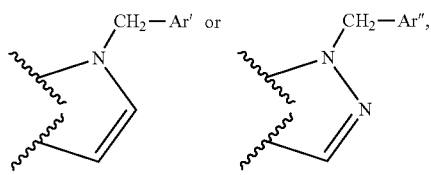

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1$-$C_4)$alkyl and halo;
$R^4$ is selected from the group consisting of H, —CN, $(C_1$-$C_4)$alkyl, —O$(C_1$-$C_4)$alkyl, halo, $(C_2$-$C_4)$alkenyl, and $(C_2$-$C_4)$alkynyl;
$R^5$ represents H or halo; and
$R^8$ represents halo, hydroxyl, or $(C_1$-$C_4)$alkyl.

In still a further aspect, the invention provides a compound of formula (9)

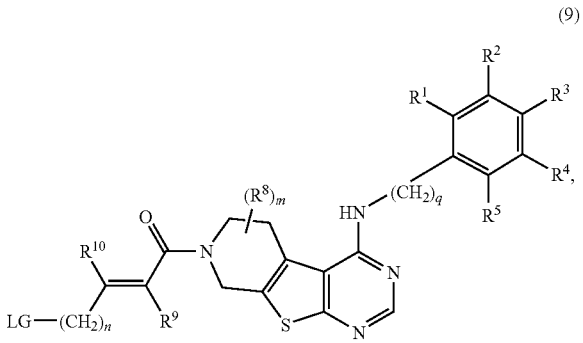

(9)

wherein
m is 0, 1, or 2;
n is 0, 1, 2, or 3;
q is 0 or 1;
$R^1$ represents H, $(C_1$-$C_4)$alkyl, or halo;
$R^2$ is selected from the group consisting of H, —CN, halo, $(C_1$-$C_4)$alkyl, —O$(C_1$-$C_4)$alkyl, $(C_2$-$C_4)$alkenyl, and $(C_2$-$C_4)$alkynyl;
$R^3$ is selected from the group consisting of H, halo, —CN, $(C_1$-$C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1$-$C_4)$alkyl and halo; or
$R^2$ and $R^3$ may be joined, and taken together with the carbon atoms to which they are attached, form a fused five- or six-membered saturated or unsaturated carbocycle, or form a fused heterocycle in which the combined $R^2$ and $R^3$ groups are represented by the formula

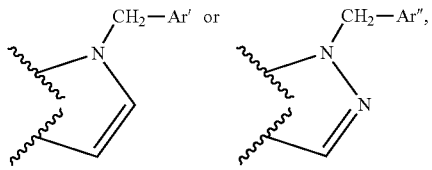

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;

$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;

$R^5$ represents H or halo;

$R^8$ represents halo, hydroxyl, or $(C_1-C_4)$alkyl;

$R^9$ represents H or —CH$_2$—Y, wherein Y is mono- or di-$((C_1-C_4)$alkyl)amino, or

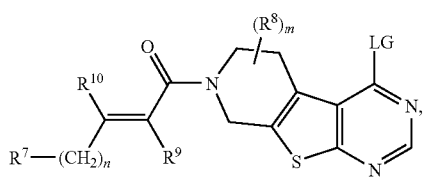

$R^{10}$ represents H;

or $R^9$ and $R^{10}$ may be taken together to form a bond, resulting in an acetylenic linkage; and LG is a leaving group.

In still another embodiment, the invention provides a compound of formula (14):

(14)

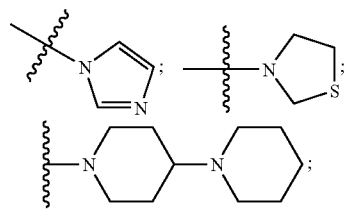

wherein m is 0, 1, or 2;

n is 0, 1, 2, or 3; q is 0 or 1;

when n is 0, $R^7$ is H;

when n is 1, 2 or 3, $R^7$ represents:

H;

hydroxyl;

—NR$^{12}$R$^{13}$ wherein $R^{12}$ represents H or $(C_1-C_6)$alkyl which optionally bears 1 or 2 hydroxyl or mono- or di-$((C_1-C_4)$alkyl)amino groups; and $R^{13}$ represents H, $(C_1-C_6)$alkyl, or $(C_3-C_6)$cycloalkyl, said alkyl and cycloalkyl groups optionally bearing 1 or 2 hydroxyl or mono- or di-$((C_1-C_4)$alkyl)amino groups;

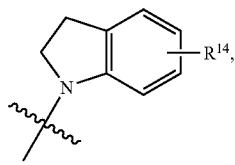

in which $R^{14}$ is hydroxyl, $(C_1-C_4)$alkyl, $(C_1-C_4)$alkoxy, or mono- or di-$((C_1-C_4)$alkyl)amino, each alkyl substituent in turn optionally bearing a hydroxyl substituent;

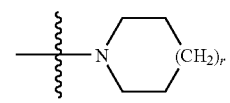

which optionally bears 1 or 2 hydroxyl, $(C_1-C_4)$alkyl, $(C_1-C_4)$alkoxy, or mono- or di-$((C_1-C_4)$alkyl)amino substituents, each alkyl substituent in turn optionally bearing a hydroxyl substituent; and wherein r is 0, 1, or 2;

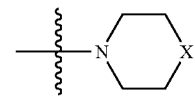

which optionally bears 1 or 2 $(C_1-C_4)$alkyl substituents, each alkyl substituent in turn optionally bearing a hydroxyl substituent; and wherein X represents O, S(O)$_s$, or NR$^{15}$, in which s is 0, 1 or 2; and $R^{15}$ represents $(C_1-C_4)$alkyl;

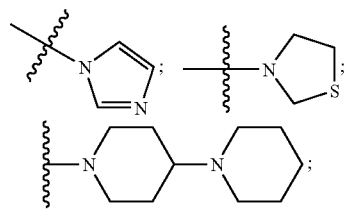

or when n=2, $R^7$ and $R^9$ may be joined, and taken together with the carbon atoms to which they are attached and the intervening carbon atoms, form a ring of structure

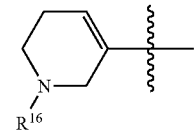

wherein $R^{16}$ represents $(C_1-C_4)$alkyl;

$R^8$ represents halo, hydroxyl, or $(C_1-C_4)$alkyl;

$R^9$ represents H or —CH$_2$—Y, wherein Y is mono- or di-$((C_1-C_4)$alkyl)amino, or

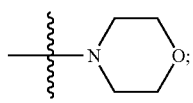

$R^{10}$ represents H;

or $R^9$ and $R^{10}$ may be taken together to form a bond, resulting in an acetylenic linkage; and LG is a leaving group.

In another embodiment, the invention provides a method of treating a cell proliferative disorder in a patient in need of such treatment, comprising administering to the patient an effective amount of a compound as above. In certain embodiments, the cell proliferative disorder is cancer.

DETAILED DESCRIPTION OF THE INVENTION

Unless otherwise stated, the following definitions apply for the technical expressions used throughout this specification and claims:

Salts for the purposes of the invention are preferably pharmaceutically acceptable salts of the compounds according to the invention. For example, see S. M. Berge, et al. "Pharmaceutical Salts," *J. Pharm. Sci.* 1977, 66, 1-19.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Alkyl represents a straight-chain or branched alkyl radical having generally 1 to 6, 1 to 4 or 1 to 3 carbon atoms, illustratively representing methyl, ethyl, n-propyl, isopropyl, tert-butyl, n-pentyl and n-hexyl.

Alkylamino represents an alkylamino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. The language "mono- or di-(($C_1$-$C_4$)alkyl) amino" refers to an alkylamino radical having one or two (independently selected) $C_1$-$C_4$alkyl substituents.

Halo represents fluorine, chlorine, bromine or iodine.

An asterisk * next to a bond denotes the point of attachment in the molecule.

The term "cell proliferative disorder" includes disorders involving the undesired or uncontrolled proliferation of a cell. Compounds can be utilized to inhibit, block, reduce, decrease, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate, solvate or ester thereof; etc. which is effective to treat the disorder. Cell proliferative or hyperproliferative disorders include but are not limited to, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other animal, including mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, e.g., rodents, e.g., mice, and non-mammals, such as non-human primates, e.g., sheep, dog, cow, chickens, amphibians, reptiles, etc.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of claim 1" is meant to include the simultaneous treatment of more than one disease as well as the administration of more than one compound of claim 1.

Depending on their structure, the compounds according to the invention can exist in stereoisomeric forms (enantiomers or diastereomers). The invention therefore relates to the enantiomers or diastereomers and to their respective mixtures. Such mixtures of enantiomers or diastereomers can be separated into stereoisomerically unitary constituents in a known manner. In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention.

In one aspect, the invention provides a compound of formula (I)

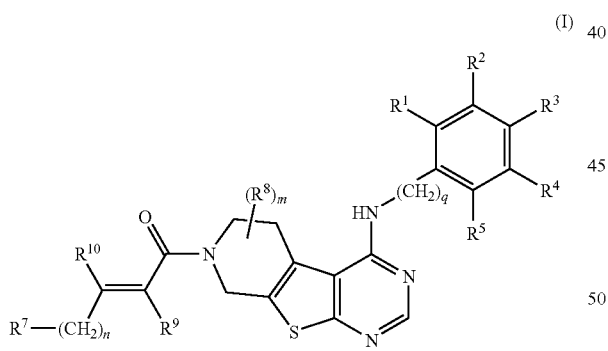

in which
m is 0, 1, or 2;
n is 0, 1, 2, or 3;
q is 0 or 1;
$R^1$ represents H, $(C_1-C_4)$alkyl, or halo;
$R^2$ is selected from the group consisting of H, —CN, halo, $(C_1-C_4)$alkyl, —O$(C_1-C_4)$alkyl, $(C_2-C_4)$alkenyl, and $(C_2-C_4)$alkynyl;
$R^3$ is selected from the group consisting of H, halo, —CN, $(C_1-C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1-C_4)$alkyl and halo; or $R^2$ and $R^3$ may be joined, and taken together with the carbon atoms to which they are attached, form a fused five- or six-membered saturated or unsaturated carbocycle, or form a fused heterocycle in which the combined $R^2$ and $R^3$ groups are represented by the formula

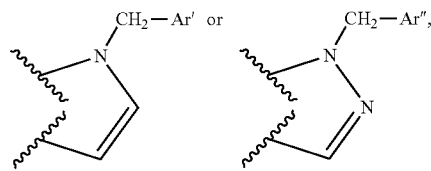

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;
$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;
$R^5$ represents H or halo;
when n is 0, $R^7$ is H;
when n is 1, 2 or 3, $R^7$ represents:
H;
hydroxyl;
—$NR^{12}R^{13}$ wherein
$R^{12}$ represents H or $(C_1-C_6)$alkyl which optionally bears 1 or 2 hydroxyl or mono- or di-$((C_1-C_4)$alkyl) amino groups; and
$R^{13}$ represents H, $(C_1-C_6)$alkyl, or $(C_3-C_6)$cycloalkyl, said alkyl and cycloalkyl groups optionally bearing 1 or 2 hydroxyl or mono- or di-$((C_1-C_4)$alkyl) amino groups;

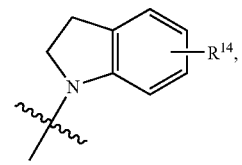

in which $R^{14}$ is hydroxyl, $(C_1-C_4)$alkyl, $(C_1-C_4)$alkoxy, or mono- or di-$((C_1-C_4)$alkyl)amino, each alkyl substituent in turn optionally bearing a hydroxyl substituent;

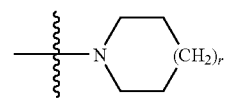

which optionally bears 1 or 2 hydroxyl, $(C_1-C_4)$alkyl, $(C_1-C_4)$alkoxy, or mono- or di-$((C_1-C_4)$alkyl)amino substituents, each alkyl substituent in turn optionally bearing a hydroxyl substituent; and wherein r is 0, 1, or 2;

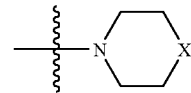

which optionally bears 1 or 2 ($C_1$-$C_4$)alkyl substituents, each alkyl substituent in turn optionally bearing a hydroxyl substituent; and wherein X represents O, $S(O)_s$, or $NR^{15}$, in which s is 0, 1 or 2; and $R^{15}$ represents ($C_1$-$C_4$)alkyl;

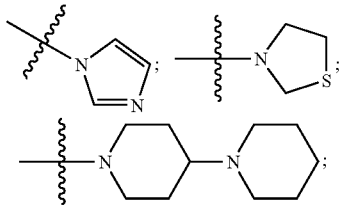

or
when n=2, $R^7$ and $R^9$ may be joined, and taken together with the carbon atoms to which they are attached and the intervening carbon atoms, form a ring of structure

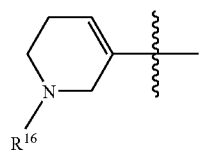

wherein $R^{16}$ represents ($C_1$-$C_4$)alkyl;

$R^8$ represents halo, hydroxyl, or ($C_1$-$C_4$)alkyl;

$R^9$ represents H or —$CH_2$—Y, wherein Y is mono- or di-(($C_1$-$C_4$)alkyl)amino, or

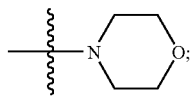 [SMILES: *N1CCOCC1]

$R^{10}$ represents H;
or
$R^9$ and $R^{10}$ may be taken together to form a bond, resulting in an acetylenic linkage;
or a pharmaceutically acceptable salt thereof.

In certain embodiments of Formula (I), m is 0. In certain embodiments, n is 1. In certain embodiments, q is 0.

In certain embodiments of Formula (I), $R^1$ is hydrogen or fluoro; $R^2$ is selected from the group consisting of H, —CN, halo, ($C_1$-$C_4$)alkyl, and ($C_2$-$C_4$)alkynyl; $R^3$ is selected from the group consisting of H, halo, and *—$O(CH_2)_p$Ar, wherein Ar is phenyl, pyridyl, or pyrazinyl, and wherein Ar can optionally be substituted with 1 or 2 halogens, and wherein p is 0 or 1; $R^4$ is selected from the group consisting of H, —CN, and halo; $R^5$ is hydrogen; and $R^7$ is —$NR^{12}R^{13}$ wherein $R^{12}$ represents H or ($C_1$-$C_6$)alkyl, and $R^{13}$ represents H or ($C_1$-$C_6$)alkyl.

In certain embodiments of Formula (I), $R^1$ is H; $R^2$ is selected from the group consisting of H, halo, and ethynyl; $R^3$ is selected from the group consisting of H, halo, —CN, methyl, and *—$O(CH_2)_p$Ar, wherein Ar is phenyl, pyridyl, or pyrazinyl, and wherein Ar can alternatively be substituted with 0, 1 or 2 halogens, and wherein p is 0 or 1; $R^4$ is selected from the group consisting of H, halo, and ($C_1$-$C_4$)alkyl; $R^5$ is hydrogen; and $R^7$ is a mono- or di-(($C_1$-$C_4$)alkyl)amino group. In certain embodiments, $R^2$ is ethynyl; $R^3$ is selected from the group consisting of H, halo, and *—$O(CH_2)_p$Ar, wherein Ar is phenyl, pyridyl, or pyrazinyl, and wherein Ar can alternatively be substituted with 0, 1 or 2 halogens, and wherein p is 0 or 1; and $R^4$ is hydrogen.

In certain embodiments of Formula (I), $R^2$ is halo; and $R^3$ is selected from the group consisting of H, halo, and *—O($CH_2)_p$Ar, wherein Ar is phenyl, pyridyl, or pyrazinyl, and wherein Ar can alternatively be substituted with 0, 1 or 2 halogens, and wherein p is 0 or 1. In certain embodiments, $R^3$ is halo.

In certain embodiments, $R^9$ and $R^{10}$ are not taken together to form an acetylenic linkage; instead, $R^9$ represents H or —$CH_2$—Y, wherein Y is mono- or di-(($C_1$-$C_4$)alkyl)amino, or

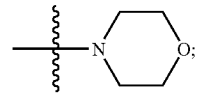

and $R^{10}$ represents H.

In certain embodiments, $R^9$ and $R^{10}$ are taken together to form a bond, resulting in an acetylenic linkage. In these embodiments, the compounds of the invention can be represented by Formula (Ia):

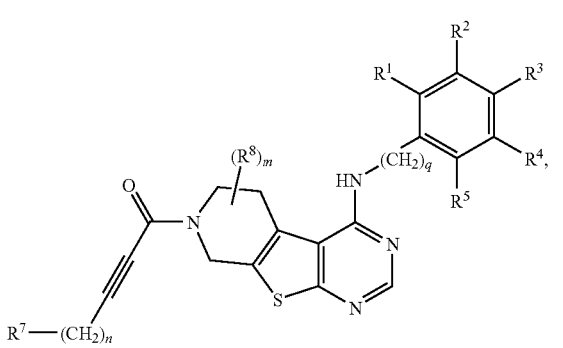

(Ia)

in which m, n, q, and $R^1$-$R^5$, and $R^7$-$R^8$ are as defined above for Formula (I), except that $R^7$ cannot be joined with $R^9$ (in these embodiments, $R^9$ and $R^{10}$ of Formula (I) have been joined, resulting in a carbon-carbon triple bond, as shown in Formula (Ia)).

In another aspect, the invention provides a compound selected from the group consisting of: N-[3-chloro-4-(pyridin-2-ylmethoxy)phenyl]-7-[(2E)-4-(diethylamino)but-2-enoyl]-5,6,7,8-tetrahydropyrido[4',3':4,5]thieno[2,3-d]pyrimidin-4-amine; N-[3-chloro-4-(pyridin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine; N-(3-chloro-4-fluorophenyl)-7-[(2E)-4-(dimethylamino)but-2-enoyl]-5,6,7,8-tetrahydropyrido[4',3':4,5]thieno[2,3-d]pyrimidin-4-amine; N-(3-chloro-4-fluorophenyl)-7-[(2E)-4-(diethylamino)but-2-enoyl]-5,6,7,8-tetrahydropyrido[4',3':4,5]thieno[2,3-d]pyrimidin-4-amine; 7-[(2E)-4-(diethylamino)but-2-enoyl]-N-(3-ethynylphenyl)-5,6,7,8-tetrahydropyrido[4',3':4,5]thieno[2,3-d]pyrimidin-4-amine; 7-[(2E)-4-(dimethylamino)but-2-enoyl]-N-(3-ethynylphenyl)-5,6,7,8-tetrahydropyrido[4',3':4,5]thieno[2,3-d]pyrimidin-4-amine; N-(3-chloro-4-fluorophenyl)-7-{(2E)-4-[isopropyl(methyl)amino]but-2-enoyl}-5,6,7,8-tetrahydropyrido[4',3':4,5]thieno[2,3-d]pyrimidin-4-amine; N-(3-chloro-4-fluorophenyl)-7-{(2E)-4-[ethyl(isopropyl)amino]but-2-enoyl}-5,6,7,8-tetrahydropyrido[4',3':4,5]thieno[2,3-d]pyrimidin-4-amine; N-(3,4-dichlorophenyl)-7-[(2E)-4-(dimethylamino)but-2-enoyl]-5,6,7,8-tetrahydropyrido[4',3':4,5]thieno[2,3-d]pyrimidin-4-amine; and N-(3,4-dichlorophenyl)-7-{(2E)-4-[isopropyl(methyl)amino]but-2-enoyl}-5,6,7,8-tetrahydropyrido[4',3':4,5]thieno[2,3-d]pyrimidin-4-amine.

In another aspect, the invention provides a process for preparing a compound of formula (I), comprising (i) reacting a compound of formula (7)

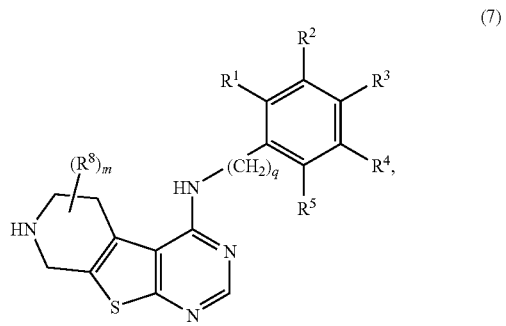

(7)

wherein $R^1$ to $R^5$, $R^8$, m and q have the meanings indicated above, with a compound of formula (10)

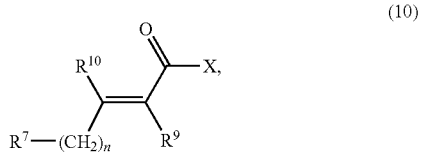

(10)

wherein $R^7$, $R^9$ and $R^{10}$ and n have the meanings indicated above, and X is hydroxy, chloro or bromo; or (ii) reacting a compound of formula (9)

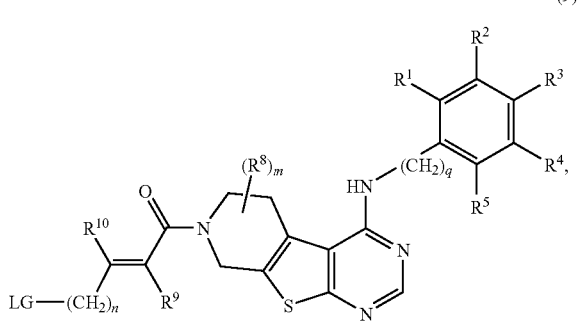

(9)

wherein $R^1$ to $R^5$, $R^8$ to $R^{10}$, m, n and q have the meanings indicated above, and LG is a leaving group, with a compound of formula $R^7$—H, wherein $R^7$ has the meaning indicated above; or (iii) reacting a compound of the formula (14):

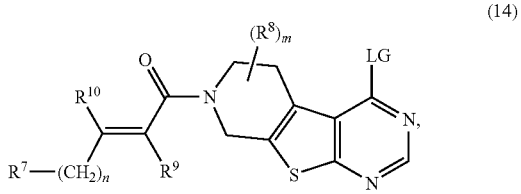

(14)

wherein $R^7$-$R^{10}$, m and n have the meanings indicated above, and LG is a leaving group, with a compound of the formula (15):

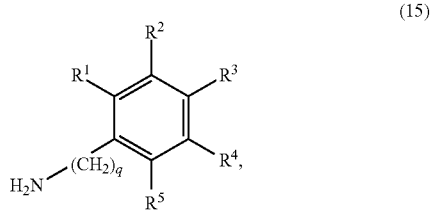

(15)

wherein $R^1$ to $R^5$, n and q have the meanings indicated above, and LG is a leaving group, under conditions such that a compound of Formula (1) is prepared.

Compounds (7), (9), and (14) as described above are useful intermediates to prepare a compound of Formula (1). For this reason, they are also part of the present invention.

It will also be understood that starting materials are commercially available or readily prepared by standard methods well known in the art. Such methods include, but are not limited to the transformations listed herein.

If not mentioned otherwise, the reactions are usually carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

The compounds of the invention may be prepared by use of known chemical reactions and procedures. Nevertheless, the following general preparative methods are presented to aid the reader in synthesizing said compounds, with more detailed particular examples being presented below in the experimental section describing the examples. The preparation of a compound of the present invention can be illustrated by means of the following synthetic scheme (I):

Schemes (I) and (II) depict the synthesis of certain compounds of Formula (I).

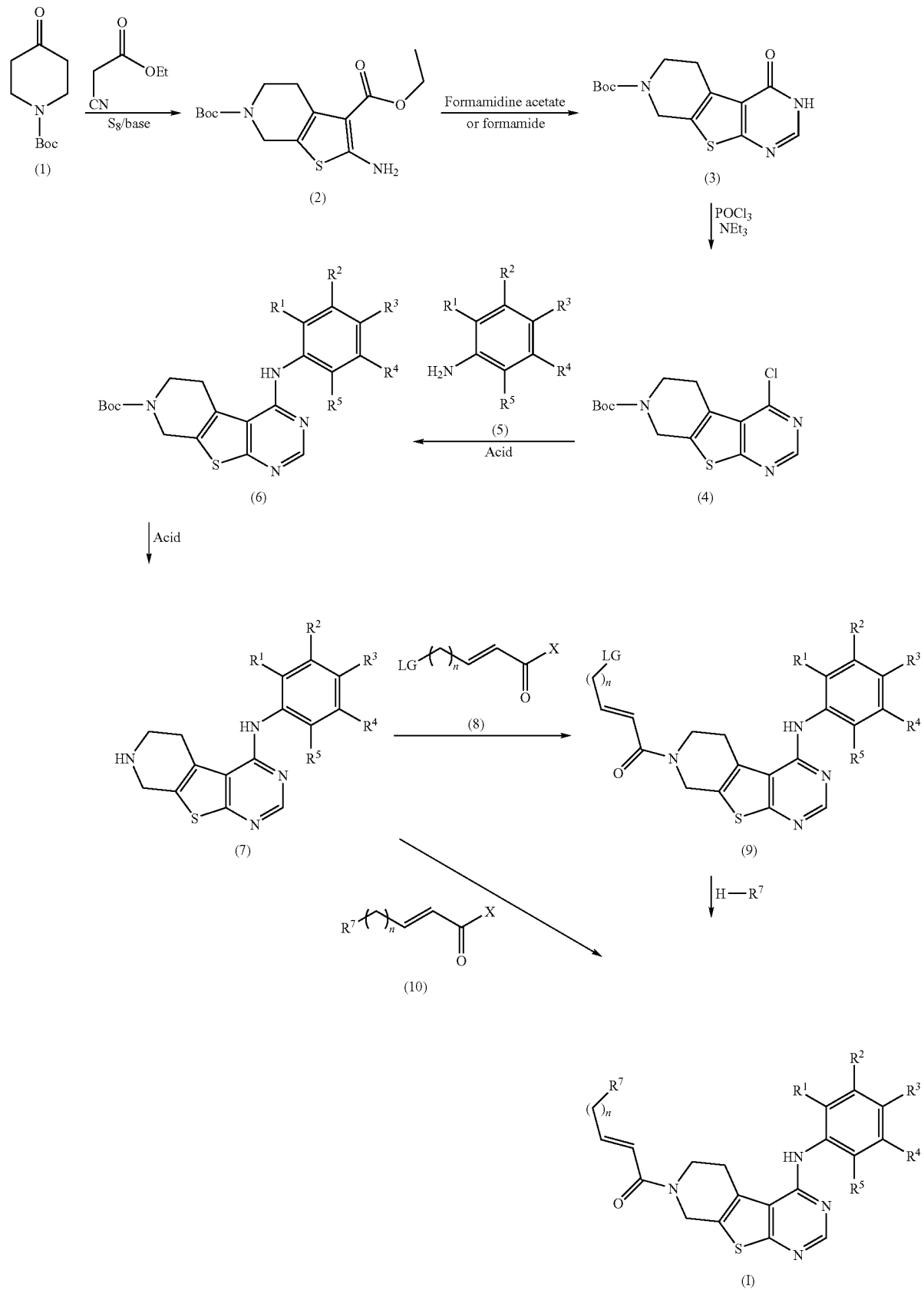
Synthetic Scheme (I)

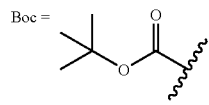

X = OH, Cl, Br
LG = Br, OTs, OMs, Cl

As shown in Scheme I, piperidinone (1) is coupled with an appropriate cyanoacetic ester (ii) in the presence of elemental sulfur and a base such as morpholine, preferably at room temperature, to yield the aminothiophene ester of formula (2) according to the procedure of Gewald, *J. Heterocyclic Chem.*, 1999, 36, 333-345. The aminothiophene ester (2) is then converted to a compound of formula (3) by reaction with a formamide-containing reagent such as neat formamide, or formamidine acetate, in a polar solvent such as DMF, with heat, preferably to 100° C. or above. Heating the compound of formula (3) with a reagent such as phosphorous oxychloride provides compound (4) which may be reacted with a variety of substituted anilines (5), each of which is readily available or can be synthesized by means well known in the art, in the presence of a catalytic amount of concentrated acid, such as HCl, and a protic solvents, such as ethanol, isopropyl alcohol to yield compound (6). Deprotection of the protecting group under acidic conditions affords compound of formula (7) which reacts with reagent (10) under classical well-established conditions to give the compound of formula (I) wherein the R$^7$ is as specified above. Alternatively, compound of formula (7) may react with reagent (8) that contains leaving group (LG) or functional group convertible to LG to give compound (9). Displacement of the leaving group in formula (9) with R$^7$—H then affords compound of formula (I).

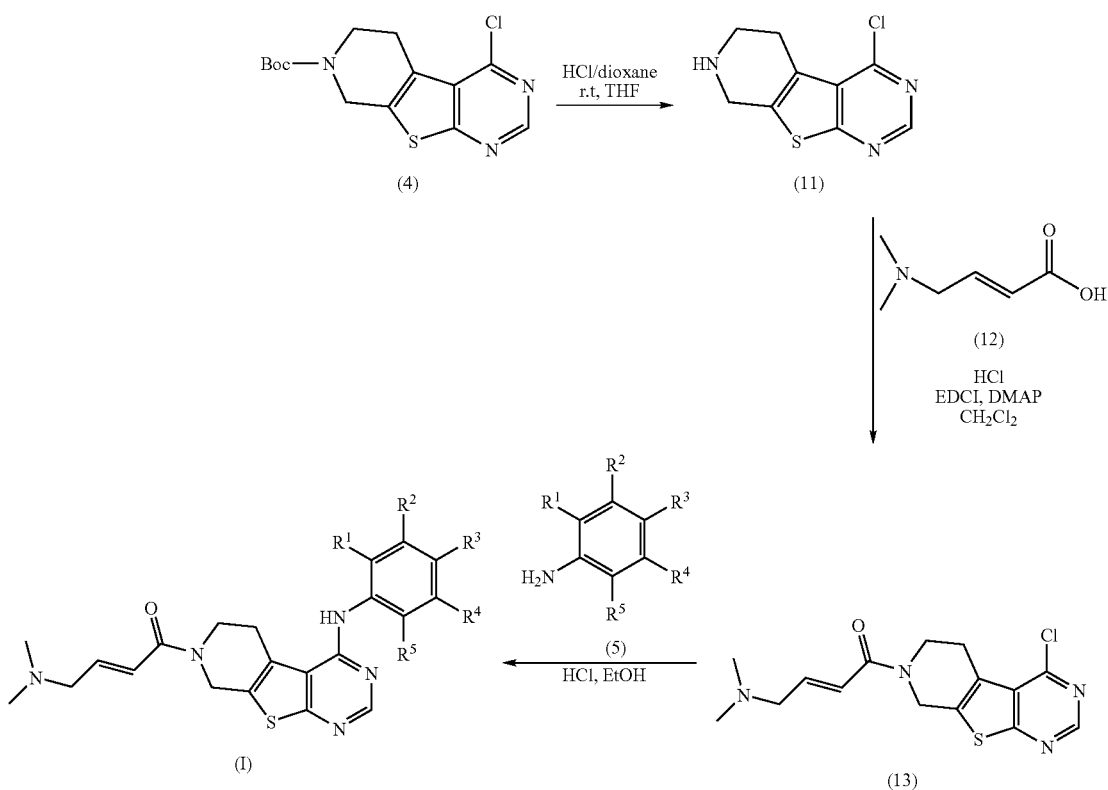

As shown in Scheme II, compound (4) was treated with acidic conditions to deprotect the Boc group and the resulting intermediate (11) was coupled with amino acid (12) (prepared according to WO 2004066919) to give compound (13) which may be reacted with a variety of substituted anilines (5), each of which is readily available or can be synthesized by means well known in the art, in the presence of a catalytic amount of concentrated acid, such as HCl, and a protic solvents, such as ethanol, isopropyl alcohol to yield compound of formula (I).

Pharmaceutical Compositions and Methods of Treatment

In another aspect, the invention provides a pharmaceutical composition comprising a compound of Formula (I) as defined above, together with a pharmaceutically acceptable carrier. In certain embodiments, the pharmaceutical composition is provided in a form suitable for intravenous administration.

In still another aspect, the invention provides a process for preparing a pharmaceutical composition. The process includes the step of comprising combining at least one compound of Formula (I) as defined above with at least one pharmaceutically acceptable carrier, and bringing the resulting combination into a suitable administration form.

In another embodiment, the invention provides a method of treating a cell proliferative disorder in a patient in need of such treatment, comprising administering to the patient an effective amount of a compound of Formula (I) as above. In certain embodiments, the cell proliferative disorder is cancer.

In still another aspect, the invention provides use of a compound of Formula (I) as defined above for manufacturing a pharmaceutical composition for the treatment or prevention of a cell proliferative disorder. In certain embodiments, the cell proliferative disorder is cancer.

When the compound(s) of the invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg/kg per day or 0.1 to 15 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention may be expected to vary from about 0.1 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the invention of the present invention is administered at a concentration of about 0.001 mg/kg to about 100 mg per kilogram of body weight, about 0.01-about 10 mg/kg or about 0.1 mg/kg-about 10 mg/kg of body weight. Ranges intermediate to the above-recited values are also intended to be part of the invention.

A. Examples

Abbreviations and Acronyms

When the following abbreviations are used throughout the disclosure, they have the following meaning:

$CDCl_3$-d chloroform-d
$CD_2Cl_2$-$d_2$ methylene chloride-$d_2$
Celite® registered trademark of Celite Corp. brand of diatomaceous earth
$CH_3CN$ acetonitrile
DCM methylene chloride
DIPEA diisoporpylethylamine
DMF N,N-dimethyl formamide
DMSO-$d_6$ dimethylsulfoxide-$d_6$
EtOAc ethyl acetate
equiv equivalent(s)
h hour(s)
$^1H$ NMR proton nuclear magnetic resonance
HCl hydrochloric acid
Hex hexanes
HPLC high performance liquid chromatography
IPA isopropyl alcohol
LCMS liquid chromatography/mass spectroscopy
MeOH methanol
min minute(s)
MS mass spectrometry
$Na_2CO_3$ Sodium carbonate
$NaHCO_3$ Sodium bicarbonate
$Na_2SO_4$ Sodium Sulfate
NMP N-Methylpyrrolidinone
$R_f$ TLC retention factor
rt room temperature
RT retention time (HPLC)
satd saturated
TFA trifluoroacetic acid
THF tetrahydrofuran
TLC thin layer chromatography General Analytical Procedures The structure of representative compounds of this invention were confirmed using the following procedures.

High pressure liquid chromatography-electrospray mass spectra (LC-MS) were obtained using one of the three analytical LC/MS systems (BRLCQ1, 2 and 5) with conditions specified below:

(A) BRLCQ1 & 2: Hewlett-Packard 1100 HPLC equipped with a quaternary pump, a variable wavelength detector set at 254 nm, a Waters Sunfire C18 column (2.1×30 mm, 3.5 uM), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flowrate of 1.0 mL/min was used with an initial hold of 0.5 minutes and a final hold at 95% B of 0.5 minutes. Total run time was 6.5 minutes.
or (B) BRLCQ5: HPLC—electrospray mass spectra (HPLC ES-MS) were obtained using a Agilent 1100 HPLC system. The Agilent 1100 HPLC system was equipped with an Agilent 1100 autosampler, quaternary pump, a variable wavelength detector set at 254 nm. The HPLC column used was a Waters Sunfire C18 (2.1×30 mm, 3.5 uM). The HPLC eluent was directly coupled without splitting to a Finnigan LCQ DECA ion trap mass spectrometer with electrospray ionization. Spectra were scanned from 140-1200 amu using a variable ion time according to the number of ions in the source. The eluents were A: 2% acetonitrile in water with 0.02% TFA and B: 2% water in acetonitrile with 0.02% TFA. Gradient elution from 10% B to 90% B over 3.0 minutes at a flowrate of 1.0 mL/min was used with an initial hold of 1.0 minutes and a final hold at 95% B of 1.0 minutes. Total run time was 7.0 minutes.

Routine one-dimensional NMR spectroscopy is performed either on 300 MHz Varian® Mercury-plus or on 400 MHz Varian® Mercury-plus spectrometers. The samples were dissolved in deuterated solvents obtained from Cambridge Isotope Labs®, and transferred to 5 mm ID Wilmad® NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$-$d_3$, 3.30 ppm for $CD_3OD$-$d_4$, 5.32 ppm for $CD_2Cl_2$-$d_4$ and 7.26 ppm for $CDCl_3$-d for $^1H$ spectra. The NMR spectra were consistent with the chemical structures shown.

The final products were sometimes purified by HPLC using the following conditions:

Gilson® HPLC system quipped with two Gilson 333/334 pumps, a Gilson 215 Autosampler, a Gilson® UV model 155 diode array detector (dual wavelength), a phenomenex Gemini 75×30 mm 5 micron column. The eluents were A: water with 0.1% $NH_4OH$ and B: acetonitrile. Gradient elution from 10% B to 90% B over 14 minutes at a flowrate of 100 mL/min. UV triggered collection at 220 nm with sensitivity 0.5.

Preparation of Starting Materials

Preparation of 4-Bromo-but-2-enoyl bromide

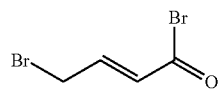

To a solution of 4-Bromo-crotonic acid (700 mg, 4.24 mmol) in DCM (10 mL)/DMF (1 drop) was added oxalyl bromide (2 M in DCM, 2.33 mL, 4.67 mmol, 1.1 equiv). The reaction mixture was heated at 40° C. for 6 h. The reaction was allowed to cool to rt then concentrated in vacuo. The crude material was used in the next step reaction without further purification. $^1H$ NMR ($CD_2Cl_2$-$d_2$) δ 7.22 (m, 1H), 6.28 (d, J=14.6 Hz, 1H), 4.10 (dd, J=1.3, 7.2 Hz, 2H).

Preparation of 3-chloro-4-(3-fluoro-benzyloxy)-phenylamine

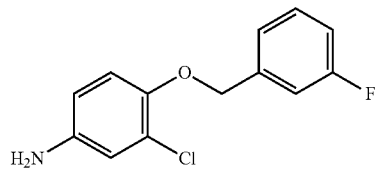 [SMILES: Nc1ccc(OCc2cccc(F)c2)c(Cl)c1]

To 90 mL $CH_3CN$ was added 2-chloro-4-nitrophenol (15 g, 86.4 mmol) followed by potassium carbonate (17.9 g, 129.6 mmol). To the stirring suspension was added via dropping funnel a 10 mL $CH_3CN$ solution of 3-fluoro-benzylbromide (16.3 g, 86.4 mmol). The contents were stirred and heated at 70° C. for 18 h, after which time the bright yellow mixture was allowed to cool to rt. The yellow contents were poured onto water (200 mL) and stirred, upon which solid formation occurs. The solid was filtered and filter cake washed with additional water (50 mL). The collected solid was dried in vacuo, yielding 2-chloro-1-(3-fluoro-benzoyloxy)-4-nitro-benzene (23 g, 94%) as a white solid.

2-Chloro-1-(3-fluoro-benzoyloxy)-4-nitro-benzene (10 g, 35.5 mmol) was suspended in 50 mL acetic acid and 150 mL EtOAc in a 500 mL flask. Iron (9.9 g, 177.5 mmol) was added to this suspension, and the mixture stirred at rt for overnight. The reaction mixture was filtered through a thin pad of Celite®. The filtrate was concentrated in vacuo and neutralized with saturated $Na_2CO_3$ aqueous solution, followed by EtOAc extraction. The organic layer was washed with brine, dried over $Na_2SO_4$, and concentrated in vacuo. The resulting crude material was purified by flash chromatography eluting with 15% EtOAc/hexanes yielding 3-chloro-4-(3-fluoro-benzyloxy)-phenylamine as a brown solid [8.5 g, 95%, TLC $R_f$=0.4, 30% EtOAc/Hex.(3:7)]. $^1$H-NMR (DMSO-$d_6$) δ 4.94 (s, 2H), 5.00 (s, 2H), 6.40 (dd, 1H), 6.60 (s, 1H), 6.87 (d, 1H), 7.10-7.18 (m, 1H), 7.20-7.28 (m, 2H), 7.37-7.44 (m, 1H).

Preparation of 3-Chloro-4-(pyridin-2-ylmethoxy)-phenylamine

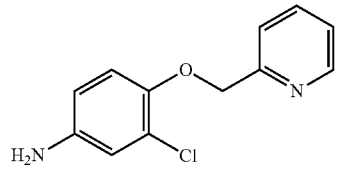 [SMILES: Nc1ccc(OCc2ccccn2)c(Cl)c1]

2-chloro-4-nitro phenol (10 g, 57.6 mmol, 1 equiv), 2-pycolyl chloride hydrogen chloride (9.45 g, 57.6 mmol, 1 equiv), cesium carbonate 41.3 (126.8 mmol, 2.2 equiv) and sodium iodide (8.64 g, 57.6 mmol, 1 equiv) were suspended in 200 mL acetonitrile. The reaction mixture was stirred at 60° C. for 5 h. The resulted suspension was filtered and washed with water (400 mL), yielding 2-(2-chloro-4-nitro-phenoxymethyl)-pyridine (8 g, 52%) as a red solid.

2-(2-chloro-4-nitro-phenoxymethyl)-pyridine (8 g, 30.2 mmol, 1 equiv) and iron (8.44 g, 151.1 mmol, 5 equiv) were mixed in acetic acid (100 mL) and EtOAc (50 mL) and were stirred at rt overnight. The reaction mixture was filtered through a pad of Celite®. The filtrate was concentrated in vacuo and neutralized with saturated $Na_2CO_3$ solution. The solution was extracted with EtOAc and the organic layer was washed with brine and concentrated in vacuo. The resulting crude material was purified by flash chromatography eluting with EtOAc/hexane (3:7) to give 3-Chloro-4-(pyridin-2-yl-methoxy)-phenylamine (3.2 g, 52%) as a white solid. $^1$H-NMR (CDCl$_3$-d) δ 5.18 (s, 2H), 6.50 (dd, 1H), 6.76 (d, 1H), 6.80 (d, 1H), 7.22 (m, 1H), 7.64 (d, 1H), 7.73 (td, 1H), 8.55 (m, 1H); LCMS RT=0.89 min, [M+H]$^+$=235.1.

Preparation of
5-amino-1-N-(3-fluorobenzyl)indazole

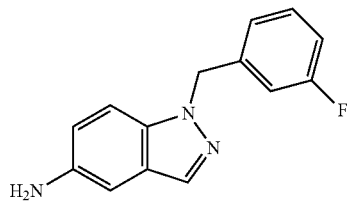

5-nitroindazole (15 g, 92 mmol, 1 eq), 3-fluorobenzylbromide (14.7 mL, 119.5 mmol, 1.3 eq) and potassium carbonate 25.4 g (184 mmol, 2 equiv) were suspended in 150 mL acetonitrile. The reaction mixture was stirred at 70° C. for 12 h, and then allowed to cool to rt. The resultant solid was filtered and washed with CH$_2$Cl$_2$, and the filtrate concentrated in vacuo. The crude mixture of regioisomeric products was purified by column:chromatography (5:1 to 4:1 Hex/EtOAc), yielding 5-nitro-1-N-(3-fluorobenzyl)indazole (7.9 g, 32%) and 5-nitro-2-N-(3-fluorobenzyl)indazole (9.2 g, 37%) as yellow solids.

5-nitro-1-N-(3-fluorobenzyl)indazole (7.9 g, 29.1 mmol, 1 equiv) and iron (8.13 g, 145.6 mmol, 5 equiv) were mixed in 200 mL acetic acid and 50 mL EtOAc, and were stirred at rt for 36 h. The reaction mixture was filtered through a pad of Celite®. The filtrate was concentrated in vacuo to 10 mL volume. The contents were diluted with water (10 mL) and neutralized with saturated Na$_2$CO$_3$ solution. The solution was extracted with EtOAc (3×500 mL), the combined organic layers dried over MgSO$_4$, filtered, and concentrated in vacuo. The resulting crude material was purified by column chromatography eluting with hexanes/EtOAC (4:1 to 3:1) to give 5-amino-1-N-(3-fluorobenzyl)indazole (5.32 g, 76%) as a light brown solid. $^1$H-NMR (DMSO-d$_6$) δ 7.72 (s, 1H), 7.22-7.36 (m, 2H), 6.87-7.05 (m, 3H), 6.70-6.77 (m, 2H), 5.48 (s, 2H), 4.78 (br s, 2H); LCMS RT=1.66 min; [M+H]$^+$=242.2.

1-Pyridin-2-ylmethyl-1H-indazol-5-ylamine was prepared using the same method described above and the appropriate reagents; LC/MS RT=1.03 min; [M+H]$^+$=225.2.

Preparation of to
3-chloro-4-[(6-methylpyridin-2-yl)methoxy]aniline

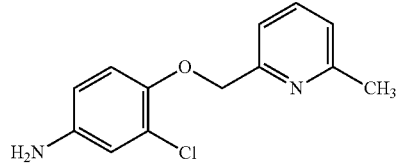 [SMILES: Cc1cccc(COc2ccc(N)cc2Cl)n1]

To 35 mL CH$_3$CN was added (6-Methyl-pyridin-2-yl)-methanol (3.5 g, 28.4 mmol), followed by potassium carbonate (17.9 g, 129.6 mmol), and 2-Chloro-1-fluoro-4-nitrobenzene (6.48 g, 36.9 mmol). The suspension was stirred and heated at 70° C. for 30 h, after which time the bright yellow mixture was allowed to cool to rt. The contents were cooled to rt, filtered, and washed with CH$_2$Cl$_2$. The filtrate was concentrated in vacuo to a a light yellow solid which was triturated with Hex/EtOAc (5:1), yielding 2-[(2-chloro-4-nitrophenoxy)methyl]-6-methylpyridine (4.87 g, 61%) as a white solid.

2-[(2-chloro-4-nitrophenoxy)methyl]-6-methylpyridine (4.87 g, 17.5 mmol) and iron powder (4.87 g, 87.4 mmol) were mixed in 150 mL acetic acid, and were stirred at rt overnight. The reaction mixture was filtered through a pad of Celite®, and washed with EtOAc. The filtrate was concentrated in vacuo and neutralized with saturated Na$_2$CO$_3$ solution. The contents were extracted with EtOAc (5×300 mL). The combined organic layers were washed with brine, dried over MgSO$_4$, filtered, and concentrated in vacuo. The resulting crude material was triturated with Hex/EtOAc (2:1) to afford 3-chloro-4-[(6-methylpyridin-2-yl)methoxy]aniline (3.84 g, 88%) as a white solid. $^1$H-NMR (DMSO) δ 7.70 (dd, 1H), 7.31 (d, 1H), 7.17 (d, 1H), 6.88 (d, 1H), 6.65 (d, 1H), 6.44 (dd, 1H), 5.01 (s, 2H), 4.93 (s, 2H), 2.46 (s, 3H); LCMS RT=0.25 min; [M+H]$^+$=249.2.

Example 1

Preparation of 1-{4-[3-Chloro-4-(pyridin-2-yl-methoxy)-phenylamino]-5,8-dihydro-6H-9-thia-1,3,7 triaza-fluoren-7-yl}-4-morpholin-4-yl-but-2-en-1-one

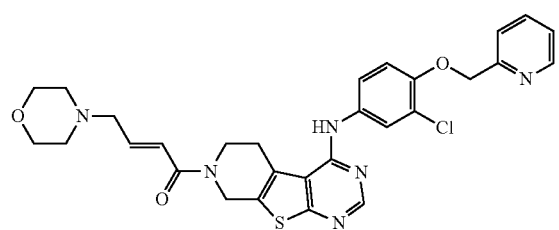 [SMILES: O=C(/C=C/CN1CCOCC1)N1CCc2c(sc3ncnc(Nc4ccc(OCc5ccccn5)c(Cl)c4)c23)C1]

Step 1. Preparation of 2-Amino-4,7-dihydro-5H-thieno[2,3-c]pyridine-3,6-dicarboxylic acid 6-tert-butyl ester 3-ethyl ester

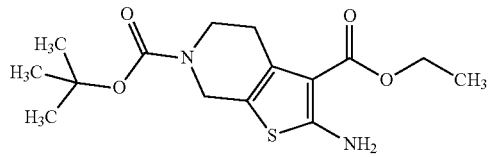

To a 1-Boc-4-piperidone (25.0 g, 123 mmol) in ethanol (100 mL) solution were added ethyl cyanoacetate (14.2 g, 123 mmol, 1 equiv), diethylamine (12.72 mL, 123 mmol, 1 equiv), and sulfur (4.14 g, 129 mmol, 1.05 equiv). The reaction was stirred at room temperature for 16 h then filtered and washed with ethanol (25 mL) to obtain a white solid (33.11 g, 102 mmol, 83%). $^1$H NMR (DMSO-$d_6$) δ 7.31 (broad s, 2H), 4.22 (s, 2H), 4.13 (q, 2H), 3.49 (t, 2H), 2.63 (t, 2H), 1.39 (s, 9H), 1.23 (t, 3H); LCMS RT=3.49 min, [M+H]$^+$=326.7.

Step 2. Preparation of 4-oxo-3,5,6,8-tetrahydro-4H-9-thia-1,3,7-triaza-fluorene-7-carboxylic acid tert-butyl ester

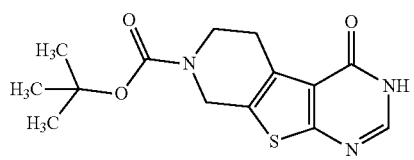 [SMILES: CC(C)(C)OC(=O)N1CCc2c(sc3nc[nH]c(=O)c23)C1]

To a 2-Amino-4,7-dihydro-5H-thieno[2,3-c]pyridine-3,6-dicarboxylic acid 6-tert-butyl ester 3-ethyl ester (5.0 g, 15 mmol) in DMF (50 mL) solution was added formamidine acetate (2.39 g, 23 mmol, 1.5 equiv). The mixture was heated at 100° C. in an oil bath for overnight. The reaction mixture was cooled to rt and then concentrated in vacuo. Ethyl acetate (50 mL) was added to the reaction solid mixture and stirred at rt for 2 h. The mixture was then filtered, rinsed with ethyl acetate (25 mL). The solid was placed in a vacuum oven and dried for overnight to yield a white solid (4.17 g, 90.6%). $^1$H NMR (CD$_3$OD-$d_4$) δ 8.05 (s, 1H), 4.57 (s, 2H), 3.61 (t, 2H), 2.92 (t, 2H), 1.42 (s, 9H); LCMS RT=2.78 min, [M+H]$^+$=308.0.

Step 3. Preparation of 4-Chloro-5,8-dihydro-6H-9-thia-1,3,7-triaza-fluorene-7-carboxylic acid tert-butyl ester

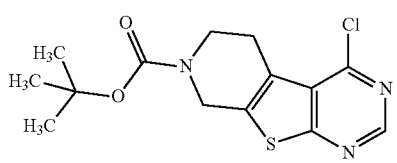 [SMILES: CC(C)(C)OC(=O)N1CCc2c(sc3ncnc(Cl)c23)C1]

To a solution of phosphorous oxychloride (30 mL) was added triethylamine (30 mL) over 15 mins at 0° C. under argon. 4-oxo-3,5,6,8-tetrahydro-4H-9-thia-1,3,7-triaza-fluorene-7-carboxylic acid tert-butyl ester (4.20 g, 14 mmol) was then added to the flask. The reaction mixture was stirred at 0° C. for 30 mins then heated at 65° C. for 2 h. The reaction mixture was cooled to rt before concentrated in vacuo. The residue was coevaporated with toluene (2×200 mL). DCM (50 mL) was added to the solid residue and the reaction mixture was quenched with ice/saturated aqueous NaHCO$_3$. The resulting mixture was extracted with DCM (3×100 mL). The combined organic layers was dried over sodium sulfate, filtered and concentrated in vacuo to yield 4.08 g (12.5 mmol, 89%) of a light yellow solid. 1H-NMR (CD$_2$Cl$_2$-$d_2$) δ 8.74 (s, 1H), 4.74 (s, 2H), 3.78 (t, 2H), 3.19 (t, 2H), 1.49 (s, 9H); LCMS RT=3.53 min, [M+H]$^+$=326.0.

Step 4. Preparation of 4-[3-Chloro-4-(pyridin-2-ylmethoxy)-phenylamino]-5,8-dihydro-6H-9-thia-1,3,7-triaza-fluorene-7-carboxylic acid tert-butyl ester

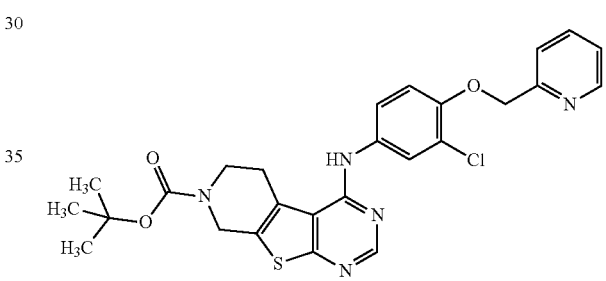

To a 4-Chloro-5,8-dihydro-6H-9-thia-1,3,7-triaza-fluorene-7-carboxylic acid tert-butyl ester (3.08 g, 9.40 mmol, 1.05 equiv) in 40 mL of isopropyl alcohol solution was added 3-Chloro-4-(pyridin-2-ylmethoxy)phenylamine (2.10 g, 9.0 mmol, 1 equiv) at rt. 4 N HCl in dioxane (0.1 mL) was added to the reaction mixture to accelerate the reaction. The reaction mixture was heated at 80° C. for 16 h. The mixture was allowed to cool to rt then filtered and washed with IPA (50 mL). DCM (100 mL) and sat. sodium bicarbonate (100 mL) were added to the solid. The mixture was stirred at rt for 1 h before separated the layers. The organic layer was dried over sodium sulfate, filtered and concentrated in vacuo to yield 4.50 g of crude material. The crude material was purified by flash chromatography (50% THF/DCM) to yield a light yellow (3.60 g, 6.87 mmol, 76%) as product. $^1$H-NMR (DMSO-$d_6$) δ 9.32 (broad s, 1H), 8.67 (d, J=4.0 Hz, 1H), 8.40 (s, 1H), 8.27 (s, 1H), 8.05 (t, 1H), 7.79 (d, J=2.7 Hz, 1H), 7.70 (d, J=8.0 Hz, 1H), 7.53 (t, 1H), 7.24 (d, J=8.9 Hz, 1H), 5.35 (s, 2H), 4.66 (s, 2H), 3.66 (t, 2H), 3.19 (t, 2H), 1.43 (s, 9H); LCMS RT=3.39 min, [M+H]⁺=524.0.

Step 5. Preparation of [3-Chloro-4-(pyridin-2-yl-methoxy)-phenyl]-(5,6,7,8-tetrahydro-9-thia-1,3,7-triaza-fluoren-4-yl)-amine

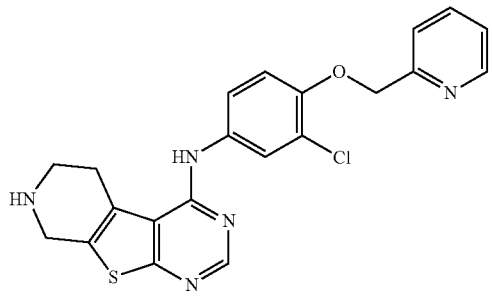 [SMILES: Clc1cc(Nc2ncnc3sc4c(c23)CCNC4)ccc1OCc1ccccn1]

To a 4-[3-Chloro-4-(pyridin-2-ylmethoxy)-phenylamino]-5,8-dihydro-6H-9-thia-1,3,7-triaza-fluorene-7-carboxylic acid tert-butyl ester (3.6 g, 6.87 mmol) in DCM (45 mL) solution was added TFA (5.2 mL, 68.7 mmol, 10 equiv). The reaction mixture was stirred at rt for 8 h. The solution mixture was concentrated in vacuo. To the residue was added sat. NaHCO₃ solution and stirred at rt for 1.5 h. The mixture was then filtered and washed with water. The damp solid was placed in a vacuum oven and dried for overnight to yield a yellow solid (2.0 g, 67%). ¹H NMR (DMSO-d₆) δ 9.41 (broad s, 2H), 8.71 (d, J=5.0 Hz, 1H), 8.40 (s, 1H), 8.11 (t, 1H), 7.75 (m, 2H), 7.57 (m, 1H), 7.53 (dd, J=2.7, 9.0 Hz, 1H), 7.25 (d, J=9.4 Hz, 1H), 5.35 (s, 2H), 4.48 (m, 2H), 3.49 (m, 2H), 3.41 (m, 2H); LCMS RT=2.11 min, [M+Na]⁺=446.1.

Step 6. Preparation of 3-Bromo-1-{4-[3-chloro-4-(pyridin-2-ylmethoxy)-phenylamino]-5,8-dihydro-6H-9-thia-1,3,7-triaza-fluoren-7-yl}-propenone

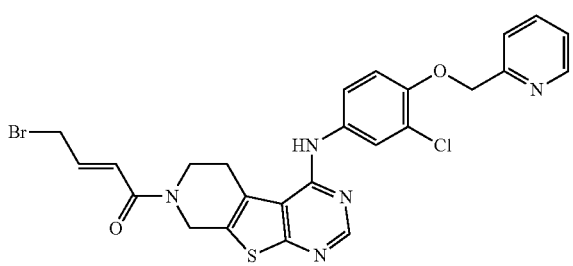 [SMILES: O=C(/C=C/CBr)N1CCc2c(sc3ncnc(Nc4ccc(OCc5ccccn5)c(Cl)c4)c23)C1]

To a [3-Chloro-4-(pyridin-2-ylmethoxy)-phenyl]-(5,6,7,8-tetrahydro-9-thia-1,3,7-triaza-fluoren-4-yl)-amine (266 mg, 0.63 mmol) in THF (4 mL)/NMP (0.8 mL) solution was added DIPEA (0.13 mL, 0.75 mmol, 1.2 equiv) and the solution was cooled to 0° C. To the reaction mixture was dropwise added 4-Bromo-but-2-enoyl bromide (217 mg, 0.75 mmol, 1.2 equiv) in THF (2 mL) solution. The mixture was stirred at 0° C. for 2 h. The reaction mixture was partitioned between sat. NaHCO₃ (25 mL) and EtOAc (50 mL). The organic layer was washed with water (25 mL) and brine (25 mL), dried over sodium sulfate, filtered, concentrated in vacuo. The crude material was used for the next step reaction without further purification. LCMS RT=2.89 min, [M+H]⁺=571.8.

Step 7. Preparation of 1-{4-[3-Chloro-4-(pyridin-2-ylmethoxy)-phenylamino]-5,8-dihydro-6H-9-thia-1,3,7 triaza-fluoren-7-yl}-4-morpholin-4-yl-but-2-en-1-one

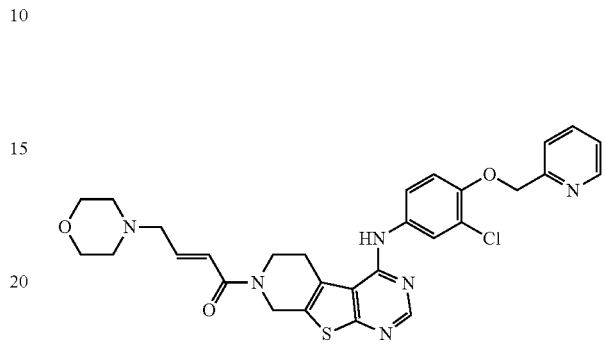

To a solution of 3-Bromo-1-{4-[3-chloro-4-(pyridin-2-yl-methoxy)-phenylamino]-5,8-dihydro-6H-9-thia-1,3,7-triaza-fluoren-7-yl}-propenone (50 mg, 0.09 mmol, 1 equiv) in DMF (0.5 mL) were added sodium iodide (14 mg, 0.09 mmol, 1 equiv), morpholine (76 mg, 0.9 mmol, 10 equiv). The resulting mixture was stirred at rt for 3 days. The reaction mixture was concentrated in vacuo then re-suspended in DCM (10 mL) and treated with satd NaHCO₃ (10 mL) to generate two clear phases. Extracted the aqueous layer with DCM (2×10 mL). The combined organic layers was dried with sodium sulfate, filtered, concentrated in vacuo. The resulting crude material was purified by prep-TLC (10% methanol/DCM) to afforded a yellow solid (12.4 mg, 0.02 mmol, 24%). ¹H-NMR (CD₂Cl₂-d₂) δ 8.50 (d, J=4.8 Hz, 1H), 8.35 (s, 1H), 7.74 (m, 1H), 7.69 (t, 1H), 7.54 (d, J=8.1 Hz, 1H), 7.32 (broad s, 1H), 7.18 (m, 1H), 6.95 (d, J=9.0 Hz, 1H), 6.78 (m, 2H), 6.43 (m, 1H), 5.18 (s, 2H), 4.78 (m, 2H), 3.90 (m, 2H), 3.60 (m, 4H), 3.08 (m, 4H), 2.37 (m, 4H); LCMS RT=2.18 min, [M+H]⁺=577.2.

Example 7

Preparation of N-(3-chloro-4-fluorophenyl)-7-[(2E)-4-(dimethylamino)but-2-enoyl]-5,6,7,8-tetrahydro-pyrido[4',3':4,5]thieno[2,3-d]pyrimidin-4-amine

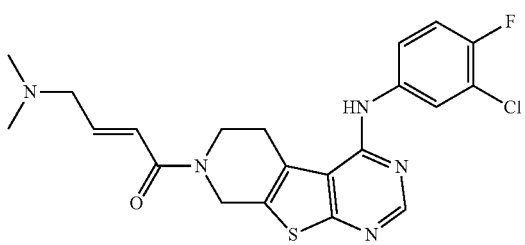 [SMILES: CN(C)C/C=C/C(=O)N1CCc2c(sc3ncnc(Nc4ccc(F)c(Cl)c4)c23)C1]

Step 1. Preparation of (3-Chloro-4-fluoro-phenyl)-(5,6,7,8-tetrahydro-9-thia-1,3,7-triaza-fluoren-4-yl)-amine

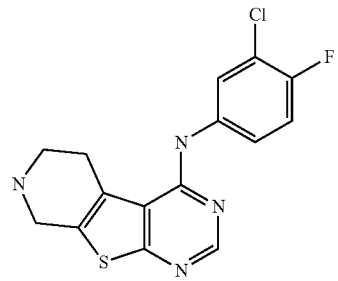 [SMILES: Fc1ccc(Nc2ncnc3sc4c(c23)CCNC4)cc1Cl]

To a mixture of 4-Chloro-5,8-dihydro-6H-9-thia-1,3,7-triaza-fluorene-7-carboxylic acid tert-butyl ester (6.86 g, 0.021 mol) and 3-chloro-4-fluoroaniline (3.2 g, 0.022 mol) in 2-propanol (96 ml) was added 4 N HCl in Dioxane (0.27 ml) and the mixture heated to 80-85° C. overnight. LCMS and TLC (5% MeOH/DCM) indicate that no SM (Boc-protected SM) present. 4 N HCl in Dioxane (10.5 ml, 0.042 mol) added and the heating continued until LCMS indicates no Boc-protected product present. Cooled to RT and conc. to dryness. The mixture was then suspended in dichloromethane (200 ml) and stirred with 1N NaOH (200 ml) for 30 min. Clear biphasic layers obtained. Layers separated and the aqueous washed with dichloromethane (100 ml). Combined organic layers washed with water (2×100 ml), then with brine (100 ml). Dried the organic layer with sodium sulfate, filtered and conc. to dryness. Dried under vacuum at to give 6.61 g (94%) of the product as indicated by LCMS and HNMR. $^1$H NMR (DMSO-d$_6$) δ 8.41 (s, 1H), 8.24 (s, 1H), 7.92 (m, 1H), 7.64 (m, 1H), 7.39 (t, J=9.4 Hz, 1H), 3.94 (broad s, 1H), 3.32 (m, 2H), 3.05 (m, 2H), 3.01 (m, 2H); LCMS RT=2.13 min, [M+H]$^+$=335.

Step 2. 4-Bromo-1-[4-(3-chloro-4-fluoro-phenylamino)-5,8-dihydro-6H-9-thia-1,3,7-triaza-fluoren-7-yl]-but-2-en-1-one

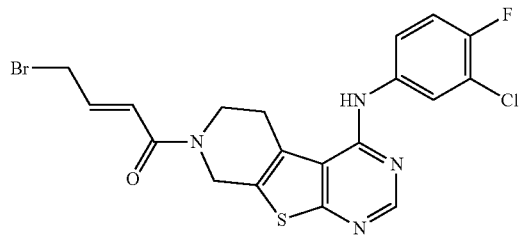 [SMILES: O=C(/C=C/CBr)N1CCc2c(sc3ncnc(Nc4ccc(F)c(Cl)c4)c23)C1]

To a solution of 4-Bromo crotonic acid (2.07 g, 0.012 mol) in dichloromethane (48 ml) at 0-5° C. was added isobutyl chloroformate (1.70 ml, 0.013 mol) followed by 4-methylmorpholine (1.40 ml, 0.013 mol) under nitrogen. This mixture was stirred at this temp. for one hour. The resulting suspension was added to a cooled solution of (3-Chloro-4-fluoro-phenyl)-(5,6,7,8-tetrahydro-9-thia-1,3,7-triaza-fluoren-4-yl)-amine (4.0 g, 0.012 mol) in dichloromethane (200 ml) over a period of 10 min. This mixture was stirred at RT for 1.5 hours. TLC (10% MeOH/DCM) shows no starting material present. The mixture was used as such in further reaction. LCMS RT=3.55 min, [M+H]$^+$=483.04.

Step 3. N-(3-chloro-4-fluorophenyl)-7-[(2E)-4-(dimethylamino)but-2-enoyl]-5,6,7,8-tetrahydropyrido[4',3':4,5]thieno[2,3-d]pyrimidin-4-amine

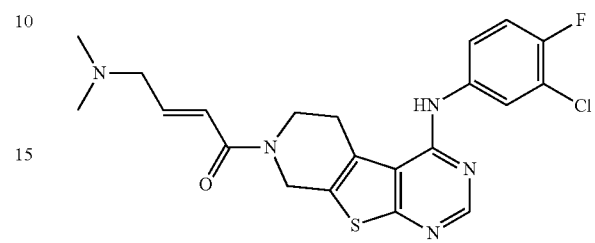

To an ice-bathed cooled solution of 4-Bromo-1-[4-(3-chloro-4-fluoro-phenylamino)-5,8-dihydro-6H-9-thia-1,3,7-triaza-fluoren-7-yl]-but-2-en-1-one (0.125 g, 0.00026 mol) in dichloromethane (1.25 ml) was added dimethylamine (2.0M solution in THF) (0.65 ml, 0.001 mol) over 1-2 min. The resulting mixture was stirred at RT for 2 hours. TLC (10% MeOH/Dichloromethane) indicates no SM present, a new polar spot seen. Conc. the reaction mixture to dryness under vacuum at 30° C. Purified by silica gel chromatography (ISCO system) using a gradient of dichloromethane—30% methanol/dichloromethane. The fractions combined, conc to dryness and the residue dissolved in 10% MeOH/DCM, filtered through a filter paper. The filterate was conc. to dryness and dried under vacuum at RT O/N to give 0.03 g (23%) of desired product. $^1$H-NMR (CD$_3$OD-d$_3$) δ 8.46 (m, 1H), 8.39 (s, 1H), 7.88 (m, 1H), 7.62 (m, 1H), 7.42 (t, 1H), 6.67 (m, 1H), 3.94 (m, 2H), 3.87 (m, 4H), 2.75 (m, 2H), 2.56 (s, 6H); LCMS RT=2.38 min, [M+H]$^+$=446.0.

Example 36

Preparation of N-(3-chloro-4-fluorophenyl)-7-{(2E)-4-[isopropyl(methyl)amino]but-2-enoyl}-5,6,7,8-tetrahydropyrido[4',3':4,5]thieno[2,3-d]pyrimidin-4-amine

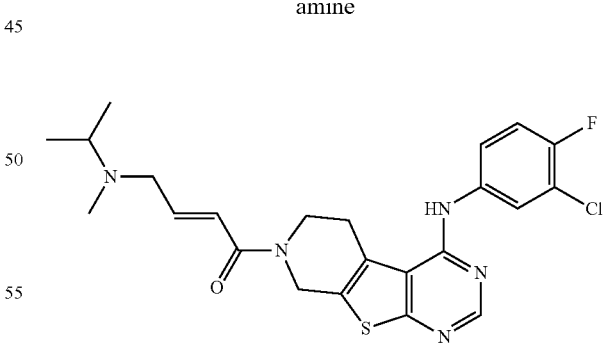

To an ice-bath cooled solution of 4-Bromo-1-[4-(3-chloro-4-fluoro-phenylamino)-5,8-dihydro-6H-9-thia-1,3,7-triaza-fluoren-7-yl]-but-2-en-1-one (0.14 g, 0.291 mmol) in dichloromethane (4.0 ml) was added isopropylmethylamine (0.121 ml, 1.16 m mol) followed by the addition of DIEA (0.056 ml, 0.32 mmol). The resulting mixture was stirred at RT overnight. TLC (10% MeOH/Dichloromethane) indicates no starting material present. The crude mixture was rotavapped to dryness, dissolved in DMF & subjected to HPLC conditions [H2O (containing 0.1% NH₄OH)-MeCN] to give the desired product (26 mg, 19%). ¹H-NMR (DMSO-d₆) δ 8.46 (m, 1H), 8.39 (s, 1H), 7.88 (m, 1H), 7.62 (m, 1H), 7.42 (t, 1H), 6.67 (m, 1H), 3.94 (m, 2H), 3.87 (m, 4H), 2.75 (m, 2H), 2.11 (s, 3H), 0.96 (d, 6H); LCMS RT=2.53 min, [M+H]⁺=474.1.

Using the methods described above and the appropriate starting materials, Examples 2-131, 186 and 188-210 were similarly prepared and listed in Table 1, together with their analytical data and IUPAC names.

Example 132

Preparation of N-[3-chloro-4-(pyridin-2-ylmethoxy) phenyl]-7-(5-piperidin-1-ylpent-2-ynoyl)-5,6,7,8-tetrahydropyrido[4',3':4,5]-thieno[2,3-d]pyrimidin-4-amine

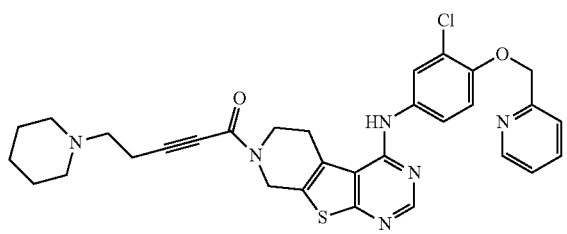 [SMILES: O=C(C#CCCN1CCCCC1)N1CCc2c(sc3ncnc(Nc4ccc(OCc5ccccn5)c(Cl)c4)c23)C1]

To a suspension of [3-Chloro-4-(pyridin-2-ylmethoxy)-phenyl]-(5,6,7,8-tetrahydro-9-thia-1,3,7-triaza-fluoren-4-yl) amine (0.051 g, 0.00028 mol), 5-Piperidin-1-yl-pent-2-ynoic acid (0.100 g, 0.00023 mol), O-(Benzotriazol-1-yl)-N,N,N',N'-tetramethyluronium tetrafluoroborate (0.091 g, 0.00028 mol) in mixture of dichloromethane/tetrahydrofuran (1.2/1.2 ml) was added diisopropylethylamine (0.123 ml, 0.001 mol) slowly over 15 min. The mixture stirred at room temperature for 3 hours. Reaction was judged complete by TLC (Eluent: 10% MeOH/DCM). The reaction mixture was concentrated to dryness under vacuum, dissolved in MeOH (1.5 ml), filtered and subjected to reverse phase HPLC purification to give the desired product (0.087 g, 62.81%)of the desired product. ¹H-NMR (CD₂Cl₂) δ 8.60 (d, 1H), 8.45 (s, 1H), 7.80 (m, 2H), 7.63 (d, 1H), 7.41 (m, 1H), 7.28 (m, 1H), 7.04 (m, 2H), 5.25 (s, 2H), 4.98 (d, 2H), 4.05 (dd, 2H), 3.10 (d, 2H), 2.60 (m, 4H), 2.40 (m, 4H), 1.62 (m, 4H), 1.45 (m, 2H); LCMS RT=2.37 min; [M+H]⁺=587.1.

HPLC separation conditions:

Column—Phenomenex gemini 75×30 mm, 5 micron

Sample dissolved in 1.5 ml of methanol

Eluent—water/acetonitrile/0.1% ammonium hydroxide@30 ml/min.; Gradient 10-90 over 20 minutes Sensitivity 0.25

Using the method described above and the appropriate starting materials, Examples 133-142 were similarly prepared and listed in Table 1, together with their analytical data and IUPAC names.

Example 143

Preparation of N-[3-chloro-4-(pyridin-2-ylmethoxy) phenyl]-7-{2-[(diethylamino)methyl]acryloyl}-5,6,7,8-tetrahydropyrido[4',3':4,5]thieno[2,3-d]pyrimidin-4-amine

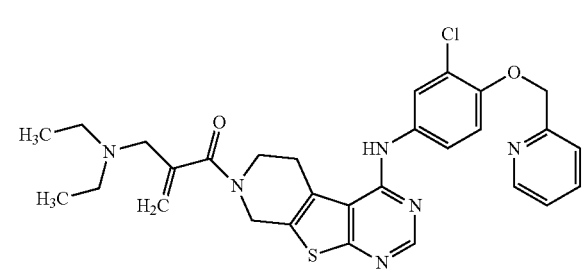 [SMILES: C=C(CN(CC)CC)C(=O)N1CCc2c(sc3ncnc(Nc4ccc(OCc5ccccn5)c(Cl)c4)c23)C1]

To a suspension of [3-Chloro-4-(pyridin-2-ylmethoxy)-phenyl]-(5,6,7,8-tetrahydro-9-thia-1,3,7-triaza-fluoren-4-yl) amine (0.053 g, 0.00034 mol), 2-Diethylaminomethyl-acrylic acid (0.12 g, 0.00028 mol), O-(Benzotriazol-1-yl)-N,N,N',N'-tetramethyluronium tetrafluoroborate (0.109 g, 0.00033 mol) in mixture of dichloromethane/tetrahydrofuran (1.2/1.2 ml) was added diisopropylethylamine (0.148 ml, 0.001 mol) slowly over 15 min. The mixture was stirred at room temperature for 16-18 hours. Reaction was judged complete by TLC (Eluent: 10% MeOH/DCM). The reaction mixture was concentrated to dryness under vacuum, dissolved in MeOH (1.5 ml), filtered and subjected to reverse phase HPLC purification to give the desired product (0.0173 g, 11.0%) of the desired product. ¹H-NMR (CD₂Cl₂) δ 8.60 (d, 1H), 8.45 (s, 1H), 7.80 (m, 2H), 7.63 (d, 1H), 7.41 (m, 1H), 7.28 (m, 1H), 7.04 (m, 2H), 5.38 (d, 2H), 5.25 (s, 2H), 4.85 (s, 2H), 4.05 (m, 2H), 3.20 (m, 4H), 2.52 (br, d, 4H), 0.98 (br, d, 6H); LCMS RT=2.32 min; [M+H]⁺=563.1.

HPLC separation conditions:Column—Phenomenex gemini 75×30 mm, 5 micron Sample dissolved in 1.5 ml of methanol. Eluent—water/acetonitrile/0.1% ammonium hydroxide@30 ml/min.; Gradient 20-80 over 20 minutes Sensitivity 0.1.

Using the method described above and the appropriate starting materials, Examples 144-149 were similarly prepared and listed in Table 1, together with their analytical data and IUPAC names.

Example 150

Preparation of 1-{4-[3-Chloro-4-(pyridin-2-yl-methoxy)-phenylamino]-5,8-dihydro-6H-9-thia-1,3,7 triaza-fluoren-7-yl}-4-morpholin-4-yl-but-2-en-1-one

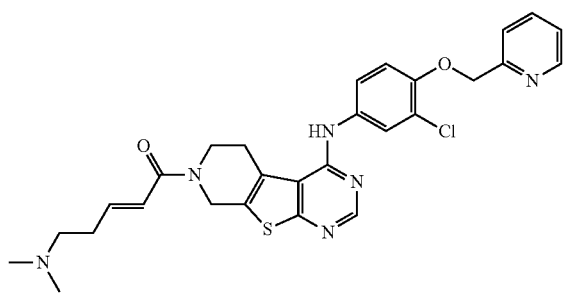 [SMILES: CN(C)CC/C=C/C(=O)N1CCc2c(sc3ncnc(Nc4ccc(OCc5ccccn5)c(Cl)c4)c23)C1]

Step 1: Synthesis of 2-but-3-enyloxy-tetrahydro-pyran

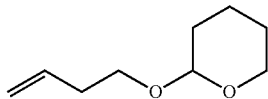

In a 1000 ml rb flask were placed 3-buten-1-ol (7.21 g, 100.00 mmol), 3,4-dihydro-2H-pyran (12.62 g, 150.00 mmol) and pyridinium p-toluenesulfonate (2.51 g, 10.00 mmol) in 350 ml of anhydrous dichloromethane. The reaction mixture was stirred at room temperature for 4 h. Then the reaction mixture was concentrated and the residue was purified by column with Hexane/Ethyl acetate=100/5 to provide 13.90 g of the desired product as an oil (89.0%). $^1$H-NMR (DMSO-d$_6$) δ 5.851-5.742 (m, 1H), 5.103-5.011 (d, 1H), 4.997-4.985 (d, 1H), 4.555-4.537 (t, 1H), 3.745-3.611 (m, 2H), 3.433-3.347 (m, 2H), 2.290-2.236 (m, 2H), 1.698-1.675 (m, 2H), 1.611-1.566 (m, 4H).

Step 2: Synthesis of 5-(tetrahydro-pyran-2-yloxy)-pent-2-enoic acid

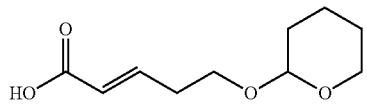 [SMILES: O=C(O)/C=C/CCOC1CCCCO1]

In a 500 ml rb flask were placed acrylic acid (2.85 g, 39.6 mmol) and Grubbs catalyst (1.68 g, 1.98 mmol) in anhydrous dichloromethane (200 ml). To this solution was added 2-but-3-enyloxy-tetrahydro-pyran (7.73 g, 49.50 mmol) and heated at refluxing for 12 hrs. The solvent was removed and the residue was purified on the column with Hexane/Ethyl acetate=100/5 to remove unchanged 2-but-3-enyloxy-tetrahydro-pyran. Then the column was eluted with Ethyl acetate/Methanol=100/1 to provide 6.66 g of a black oil (84%). $^1$H-NMR (DMSO-d$_6$) δ 12.190 (s, 1H), 6.845-6.771 (m, 1H), 5.846-5.800 (d, 1H), 4.565-4.548 (t, 1H), 3.739-3.674 (m, 2H), 3.468-3.398 (m, 2H), 2.481-2.395 (m, 2H), 1.689-1.609 (m, 2H), 1.501-1.259 (m, 4H).

Step 3: Synthesis of 1-[4-[3-chloro-4-(pyridin-2-ylmethoxy)-phenylamino]-5,8-dihydro-6H-9-thia-1,3,7-triaza-fluoren-7-yl}-5-(tetrahydro-pyran-2-yloxy)-pent-2-en-1-one

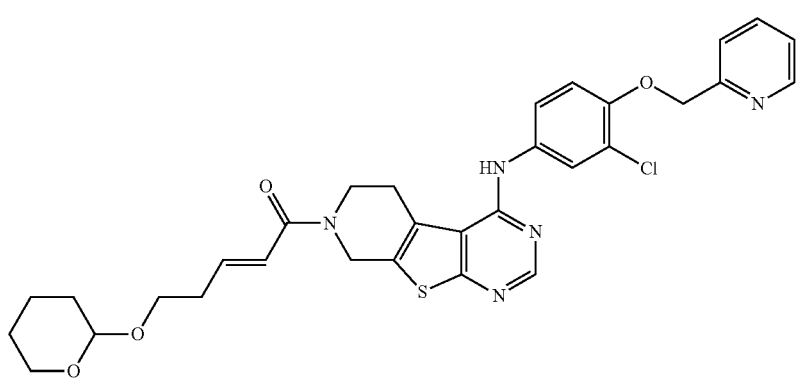 [SMILES: O=C(/C=C/CCOC1CCCCO1)N1CCc2c(sc3ncnc(Nc4ccc(OCc5ccccn5)c(Cl)c4)c23)C1]

In a 100 ml rb flask were placed [3-chloro-4-(pyridine-2-ylmethoxy)-phenyl]-(5,6,7,8-tetrahydro-9-thia-1,3,7-triaza-fluoren-4-yl)-amine (2.0, 4.71 mmol), 5-(tetrahydro-pyran-2-yloxy)-pent-2-enoic acid (0.94 g, 4.71 mmol) and O-(Benzotriazol-1-yl)-N,N,N',N'-tetrafluorobonate (1.81 g, 5.66 mmol) in anhydrous dichloromethane/THF (15 ml/15 ml) and cooled at 0° C. To this cooled suspension was slowly added diisopropylethylamine (1.83 g, 14.15 mmol) (2.5 ml) during 15 minute. Then the reaction mixture was warmed to room temperature and stirred at room temperature for 12 hours. The reaction mixture was concentrated at room temperature (no heating) to remove dichloromethane. To the residue was added water and precipitated grey-white solid was filtered and washed with water. The grey-white solid was further suspended in methyl alcohol, sonicated, filtered and dried to provide 2.26 g of grey-white solid. (80.0%). It will be carried to next step reaction without any purification. $^1$H-NMR (DMSO-d$_6$) δ 8.593-8.575 (m, 1H), 8.391 (s, 1H), 8.191 (s, 1H), 7.872-7.868 (m, 1H), 7.769 (s, 1H) 7.571-7.498 (m, 2H), 7.369-7.329 (m, 1H), 7.236-7.214 (d, 1H), 6.779-6.607 (m, 2H), 5.274 (s, 2H), 4.946-4.835 (d, 2H), 4.572 (s, 1H), 3.928-3.730 (m, 2H), 3.504-3.402 (m, 2H), 3.313-3.204 (m, 4H), 1.673-1.434 (m, 8H). MS m/e 605.9 (M+H), RT=3.02 min Step 4: Synthesis of 1-[4-[3-chloro-4-(pyridin-2-ylmethoxy)-phenylamino]-5,8-dihydro-6H-9-thia-1,3,7-triaza-fluoren-7-yl}-5-hydroxy-pent-2-en-1-one

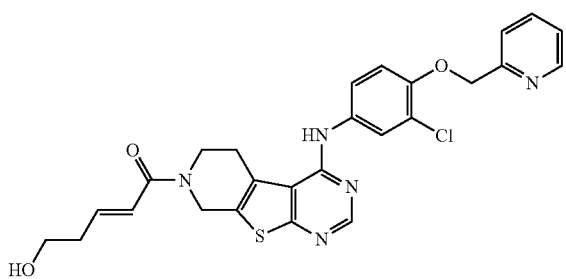 [SMILES: O=C(/C=C/CCO)N1CCc2c(sc3ncnc(Nc4ccc(OCc5ccccn5)c(Cl)c4)c23)C1]

In a 250 ml rb flask were placed 1-[4-[3-chloro-2-ylmethoxy)-phenylamino]-5,8-dihydro-6H-9-thia-1,3,7-triaza-fluoren-7-yl]-5-(tetrahydro-pyran-2-yloxy)-pent-2-en-1-one (2.26 g, 3.73 mmol) and pyridinium p-toluenesulfonate (0.18 g, 0.74 mmol) in ethanol alcohol (100 ml). The reaction mixture was heated at 80 C for 12 hours. Ethyl alcohol was evaporated and to the residue was added methyl alcohol, sonicated and off-white solid was filtered and washed with methyl alcohol, dried to provide 1.72 g of off-white solid. (88.40%). $^1$H-NMR (DMSO-d$_6$) δ 8.587-8.578 (m, 1H), 8.396 (s, 1H), 8.182 (s, 1H), 7.887-7.849 (t, 1H), 7.769 (s, 1H), 7.570-7.501 (m, 2H), 7.368-7.356 (t, 1H), 7.231-7.209 (d, 1H), 6.779-6.607 (m, 2H), 5.271 (s, 2H), 4.944 (s, 1H), 4.834 (s, 1H), 4.661 (s, 1H), 3.925-3.848 (d, 2H), 3.519 (m, 2H), 3.245-3.206 (m, 2H), 2.360 (m, 2H). MS m/e 522.0 (M+H), RT=2.54 min Step 5: Synthesis of methanesulfonic acid 5-{4-[3-chloro-4-(pyridine-2-ylmethoxy)-phenylamino]-5,8-dihydro-6H-9-thia-1,3,7-triaza-fluoren-7-yl}-5-oxo-pent-3-enyl ester

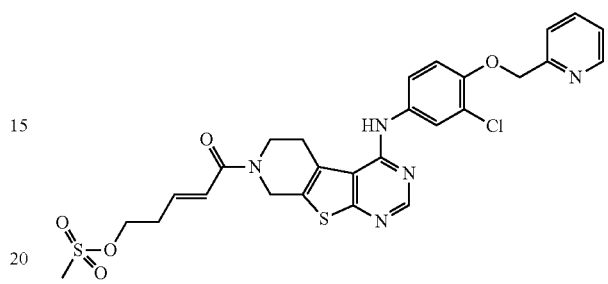

In a 250 ml rb flask were placed 1-[4-[3-chloro-4-(pyridin-2-ylmethoxy)-phenyl amino]-5,8-dihydro-6H-9-thia-1,3,7-triaza-fluoren-7-yl}-5-hydroxy-pent-2-en-1-one (1.00 g, 1.91 mmol) in THF (80 ml) and to the solution was added triethylamine (0.58 g, 5.74 mmol) (0.80 ml) followed by methanesulfonyl chloride (0.54 g, 4.79 mmol) at 0° C. The reaction mixture was stirred at room temperature overnight. THF was evaporated and to the residue was added water and small amount of methyl alcohol, sonicated. The precipitated off-white solid was filtered, washed with methyl alcohol and dried to provide 0.63 g of off-white solid. (55%) $^1$H-NMR (DMSO-d$_6$) δ 8.601-8.585 (m, 1H), 8.394 (s, 1H), 8.196 (s, 1H), 7.906-7.864 (m, 1H), 7.769 (s, 1H), 7.584-7.564 (d, 1H), 7.523-7.501 (d, 1H), 7.388-7.357 (m, 1H), 7.239-7.216 (d, 1H), 6.765-6.703 (m, 2H), 5.280 (s, 2H), 4.957 (s, 1H), 4.843 (s, 1H), 4.366-4.337 (m, 2H), 3.940-3.860 (m, 2H), 3.255-3.189 (m, 6H), 2.655-2.626 (m, 2H). MS m/e 600.0 (M+H), RT=2.78 min Step 6: Synthesis of 1-[4-[3-chloro-4-(pyridin-2-ylmethoxy)-phenylamino]-5,8-dihydro-6H-9-thia-1,3,7-triaza-fluoren-7-yl}-5-dimethylamino-pent-2-en-1-one

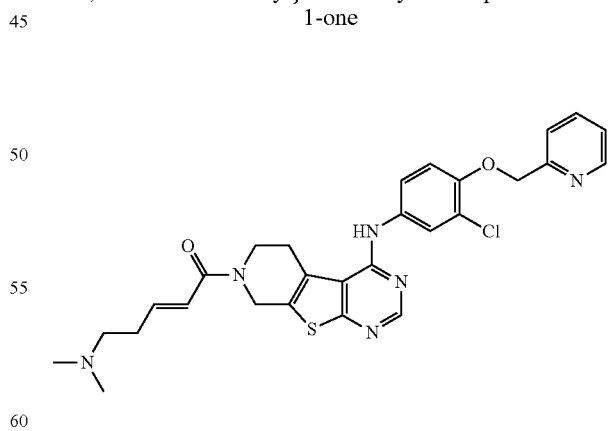

In a 25 ml rb flask were placed methanesulfonic acid 5-{4-[3-chloro-4-(pyridine-2-ylmethoxy)-phenylamino]-5,8-dihydro-6H-9-thia-1,3,7-triaza-fluoren-7-yl}-5-oxo-pent-3-enyl ester (0.15 g, 0.25 mmol) in DMF (5.0 ml) and to the solution was added cesium carbonate (0.16 g, 0.5 mmol) followed by dimethylamine (0.5 ml of 2M solution in THF) and heated at 50° C. overnight. The yellow solution was purified by HPLC twice to provide 27.5 mg of light brown solid (20.0%). ¹H-NMR (DMSO-d$_6$) δ 8.592-8.574 (m, 1H), 8.378 (s, 1H), 8.181 (s, 1H), 7.890-7.847 (m, 1H), 7.781-7.752 (m, 1H), 7.572-7.552 (d, 1H), 7.514-7.492 (m, 1H), 7.372-7.341 (m, 1H), 7.237-7.207 (m, 1H), 5.271 (s, 2H), 4.942-4.761 (m, 2H), 3.922-3.781 (m, 2H), 3.282-3.169 (m, 4H), 2.343 (m, 2H), 2.127-1.977 (m, 8H). MS m/e 549.1 (M+H), RT=2.26 min Using the method described above and the appropriate starting materials, Examples 151-159 were similarly prepared and listed in Table 1, together with their analytical data and IUPAC names.

Example 165

Preparation of N-(3,4-dichlorophenyl)-7-{(2E)-4-[dimethylamino]but-2-enoyl}-5,6,7,8-tetrahydropyrido[4',3':4,5]thieno[2,3-d]pyrimidin-4-amine

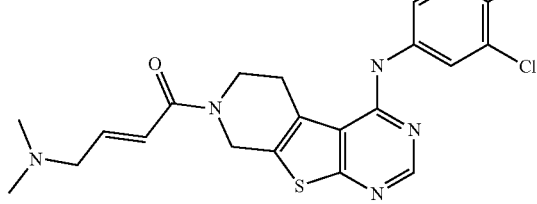

Step 1: Preparation of 4-chloro-5,6,7,8-tetrahydropyrido[4',3':4,5]thieno[2,3-d]pyrimidine

To a solution of tert-butyl 4-chloro-5,8-dihydropyrido[4',3':4,5]thieno[2,3-d]pyrimidine-7(6H)-carboxylate (3500 mg, 10.7 mmol) in THF (100 mL) was added 4 N HCl in 1,4-dioxane (4 N, 6 mL). The reaction mixture was stirred at room temperature for 24 h. The white precipitate was collected and dried under reduced pressure and gave 2000 mg (82%) of the desired product. LCMS RT=0.21 min, [M+1]⁺=226.

Step 2: Preparation of (2E)-4-(4-chloro-5,8-dihydropyrido[4',3':4,5]thieno[2,3-d]pyrimidin-7(6H)-yl)-N,N-dimethyl-4-oxobut-2-en-1-amine

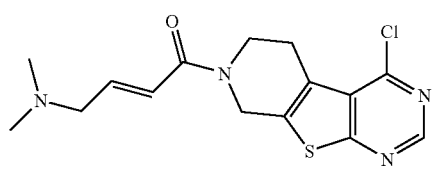 [SMILES: CN(C)C/C=C/C(=O)N1CCc2c(sc3ncnc(Cl)c23)C1]

To a solution of 4-chloro-5,6,7,8-tetrahydropyrido[4',3':4,5]thieno[2,3-d]pyrimidine (1000 mg, 4.0 mmol, 90% pure) in THF (20 mL) were added (2E)-4-(dimethylamino)but-2-enoic acid hydrochloride (730 mg, 4.4 mmol), EDCI (840 mg, 4.4 mmol), DMAP (97 mmol, 0.8 mmol) and diisopropylethylamine (120 mg, 8.0 mmol). The reaction mixture was stirred at room temperature for 16 h. The mixture was then concentrated to dryness under reduced pressure. The residue was purified by ISCO using a 20% ethyl acetate in methanol to obtain 1100 mg (82%) of the desired product. LCMS RT=1.51 min, [M+1]⁺=337.

Step 3: Preparation of N-(3,4-dichlorophenyl)-7-{(2E)-4-[dimethylamino]but-2-enoyl}-5,6,7,8-tetrahydropyrido[4',3':4,5]thieno[2,3-d]pyrimidin-4-amine

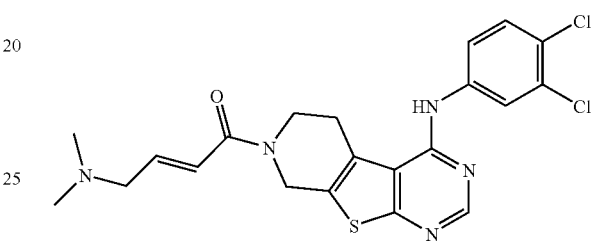

To a solution of (2E)-4-(4-chloro-5,8-dihydropyrido[4',3':4,5]thieno[2,3-d]pyrimidin-7(6H)-yl)-N,N-dimethyl-4-oxobut-2-en-1-amine (50 mg, 0.15 mmol) in ethanol (2 mL) were added HCl in 1,4-dioxane (4N, 0.02 ml) and 3-bromoaniline (26 mg, 0.16 mmol). The reaction was heated (80° C.) for 4 h and then cooled to rt. The mixture was extracted with ethyl acetate (2 mL) and the extract was concentrated to dryness under reduced pressure. The residue was dissolved in a mixture of methanol and acetonitrile and purified by HPLC using a 70% acetonitrile in water to obtain 9 mg (13%) of the desired product. ¹H-NMR (CD$_3$OD-d$_3$) δ 8.42 (s, 1H), 7.99 (m, 1H), 7.57 (m, 1H), 7.46 (m, 1H), 6.80 (m, 1H), 4.93 (m, 2H), 4.04 (t, 2H), 3.20 (m, 4H), 2.31 (s, 3H), 2.29 (s, 3H); LCMS RT=2.60 min, [M+1]⁺=462.3.

Using the method described above and the appropriate starting materials, Examples 161-164 and 166-185 were similarly prepared and listed in Table 1, together with their analytical data and IUPAC names.

Example 187

Preparation of N-(3,4-dichlorophenyl)-7-1(2E)-4-[isopropyl(methyl)amino/but-2-enoyl]-5,6,7,8-tetrahydropyrido[4',3':4,5]thieno[2,3-d]pyrimidin-4-amine

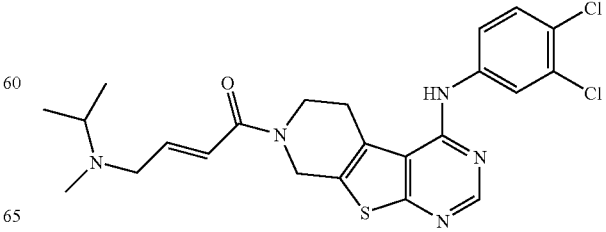

Step 1. Preparation of (3,4-dichloro-phenyl)-(5,6,7,8-tetrahydro-9-thia-1,3,7-triaza-fluoren-4-yl)-amine

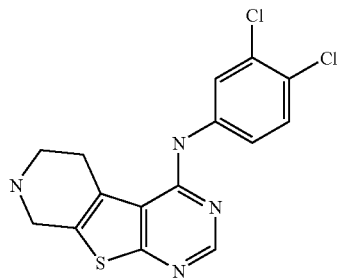 [SMILES: Clc1ccc(Nc2ncnc3sc4c(c23)CCNC4)cc1Cl]

Following the same procedure as described in Example 7, step 1 using 4-Chloro-5,8-dihydro-6H-9-thia-1,3,7-triaza-fluorene-7-carboxylic acid tert-butyl ester (3.5 g, 0.011 mol), 3,4-dichloroaniline (1.9 g, 0.012 mol), 4 N HCl in Dioxane (1.3 ml) in 2-propanol (72 ml) and gave the desired product (3.0 g, 72%). LCMS RT=2.77 min, [M+H]$^+$=351.8.

Step 2. Preparation of N-(3,4-dichlorophenyl)-7-{(2E)-4-[isopropyl(methyl)amino]but-2-enoyl}-5,6,7,8-tetrahydropyrido[4',3':4,5]thieno[2,3-d]pyrimidin-4-amine

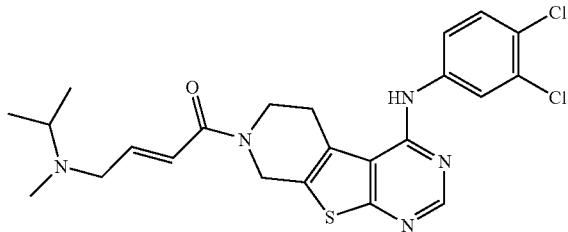 [SMILES: CC(C)N(C)C/C=C/C(=O)N1CCc2c(sc3ncnc(Nc4ccc(Cl)c(Cl)c4)c23)C1]

To 4-Bromo-but-2-enoic acid (638 mg, 3.87 mmol) in CH$_2$Cl$_2$ was added isopropylmethyamine (1.1 ml, 10.3 mmol), the mixture was stirred for 2 hours followed by addition of (3,4-dichloro-phenyl)-(5,6,7,8-tetrahydro-9-thia-1,3,7-triaza-fluoren-4-yl)-amine (1.0 g, 2.57 mmol), EDCI (493 mg, 2.58 mmol), DIPEA (1.8 ml, 10.3 mmol). The resulting mixture was stirred at RT overnight. Solvents were removed and residue was purified by HPLC to gave the desired compound (500 mg, 13%). $^1$H-NMR (DMSO-d$_6$) δ 8.46 (m, 1H), 8.39 (s, 1H), 7.88 (m, 1H), 7.62 (m, 1H), 7.42 (t, 1H), 6.67 (m, 1H), 3.94 (m, 2H), 3.87 (m, 4H), 2.75 (m, 2H), 2.11 (s, 3H), 0.96 (d, 6H); LCMS RT=2.72 min, [M+1]$^+$=490.3.

Analytical Data for Selected Examples

The following analytical data were found for the Examples:

Example 2

N-[3-chloro-4-(pyridin-2-ylmethoxy)phenyl]-7-[(2E)-4-(diethylamino)but-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.50 (d, J=4.50 Hz, 1H), 8.36 (s, 1H), 7.74 (s, 1H), 7.68 (td, J=7.63, 1.37 Hz, 1H), 7.54 (d, J=7.83 Hz, 1H), 7.33 (broad s, 1H), 7.19 (m, 1H), 6.95 (d, J=9.0 Hz, 1H), 6.79 (m, 2H), 6.42 (m, 1H), 5.18 (s, 2H), 4.81 (m, 2H), 3.88 (m, 2H), 3.19 (m, 2H), 3.12 (m, 2H), 2.49 (m, 4H), 0.97 (m, 6H); LCMS RT=2.37 min, [M+H]$^+$=563.2.

Example 3

N-[3-chloro-4-(pyridin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.50 (d, J=4.70 Hz, 1H), 8.36 (s, 1H), 7.75 (s, 1H), 7.69 (td, J=7.68, 1.27 Hz, 1H), 7.54 (d, J=7.83 Hz, 1H), 7.32 (s, 1H), 7.18 (m, 1H), 6.96 (d, J=8.80 Hz, 1H), 6.79 (m 2H), 6.43 (m, 1H), 5.19 (s, 2H), 4.82 (m, 2H), 3.90 (m, 2H), 3.10 (m, 4H), 2.24 (s, 3H), 2.17 (s, 3 H); LCMS RT=2.31 min, [M+H]$^+$=536.2.

Example 4

N-[3-chloro-4-(pyridin-2-ylmethoxy)phenyl]-7-[(2E)-4-piperidin-1-ylbut-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.50 (d, J=4.70 Hz, 1H), 8.36 (s, 1H), 7.75 (d, J=1.76 Hz, 1H), 7.69 (td, J=7.68, 1.66 Hz, 1H), 7.54 (d, J=7.83 Hz, 1H), 7.35 (s, 1H), 7.18 (m, 1H), 6.96 (d, J=8.80 Hz, 1H), 6.82 (s, 1H), 6.75 (s, 1H), 6.42 (m, 1H), 5.19 (s, 2H), 4.81 (m, 2H), 3.91 (m, 2H), 3.11 (m, 4H), 2.39 (m, 4H), 1.56 (m, 4H), 1.37 (m, 2H); LCMS RT=2.39 min, [M+H]$^+$=575.2.

Example 5

N-[3-chloro-4-(pyridin-2-ylmethoxy)phenyl]-7-[(2E)-4-(4-methylpiperazin-1-yl)but-2-enoyl]-5,6,7,8-tetrahydropyrido[4',3':4,5]thieno[2,3-d]pyrimidin-4-amine $^1$H-NMR (CD$_3$OD-d$_3$) δ 8.55 (d, J=4.50 Hz, 1H), 8.32 (s, 1H), 7.91 (t, 1H), 7.78 (m, 1H), 7.70 (d, J=7.83 Hz, 1H), 7.41 (m, 2H), 7.10 (d, J=9.00 Hz, 1H), 6.82 (m, 1H), 6.43 (m, 1H), 5.23 (s, 2H), 5.00 (m, 4H), 4.02 (t, 2H), 3.24 (m, 4H), 2.75 (m, 2H), 2.29 (m, 4H), 2.04 (s, 3H); LCMS RT=2.32 min, [M+H]$^+$=590.2.

Example 6

N-(3-chloro-4-fluorophenyl)-7-[(2E)-4-morpholin-4-ylbut-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.49 (s, 1H), 7.93 (m, 1H), 7.46 (m, 1H), 7.18 (t, 1H), 6.84 (m, 1H), 6.65 (m, 2H), 4.89 (m, 2H), 4.00 (m, 2H), 3.68 (m, 4H), 3.17 (m, 4H), 2.46 (m, 4H); LCMS RT=2.40 min, [M+H]$^+$=488.1.

Example 8

N-(3-chloro-4-fluorophenyl)-7-[(2E)-4-(4-methylpiperazin-1-yl)but-2-enoyl]-5,6,7,8-tetrahydropyrido[4',3':4,5]thieno[2,3-d]pyrimidin-4-amine $^1$H-NMR (CD$_3$OD-d$_3$) δ 8.36 (s, 1H), 7.87 (m, 1H), 7.54 (m, 1H), 7.22 (t, 1H), 6.82 (s, 1H), 6.78 (m, 1H), 4.02 (t, 2H), 3.27 (m, 4H), 3.22 (m, 2H), 2.75 (m, 4H), 2.64 (m, 4H), 2.47 (s, 3H); LCMS RT=2.32 min, [M+H]$^+$=501.1.

Example 9

N-(3-chloro-4-fluorophenyl)-7-[(2E)-4-(diethylamino)but-2-enoyl]-5,6,7,8-tetrahydropyrido[4',3':4,5]thieno[2,3-d]pyrimidin-4-amine $^1$H-NMR (CD$_3$OD-d$_3$) δ 8.39 (s, 1H), 7.87 (m, 1H), 7.54 (m, 1H), 7.24 (t, 1H), 7.13 (dd, J=15.0, 37.0 Hz, 1H), 6.80 (m, 1H), 4.06 (t, 2H), 3.93 (t, 2H), 3.30 (m, 4H), 3.16 (m, 4H), 1.31 (t, 6H); LCMS RT=2.52 min, [M+H]$^+$=474.1.

Example 10

N-{3-chloro-4-[(3-fluorobenzyl)oxy]phenyl}-7-[(2E)-4-morpholin-4-ylbut-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.45 (s, 1H), 7.81 (m, 1H), 7.40 (m, 2H), 7.26 (m, 2H), 7.06 (td, J=8.48, 2.34 Hz, 1H), 7.00 (d, J=8.77 Hz, 1H), 6.84 (m, 2H), 6.55 (m, 1H), 5.17 (s, 2H), 4.88 (m, 2H), 4.03 (m, 2H), 3.69 (m, 4H), 3.17 (m, 4H), 2.46 (m, 4H); LCMS RT=2.86 min, [M+H]$^+$=594.3.

Example 11

N-{3-chloro-4-[(3-fluorobenzyl)oxy]phenyl}-7-[(2E)-4-(dimethylamino)but-2-enoyl]-5,6,7,8-tetrahydropyrido[4',3':4,5]thieno[2,3-d]pyrimidin-4-amine $^1$H-NMR (DMSO-d$_6$) δ 8.38 (s, 1H), 8.19 (m, 1H), 7.76 (d, J=7.60 Hz, 1H), 7.51 (d, J=8.96 Hz, 1H), 7.45 (m, 1H), 7.32-7.15 (m, 5H), 6.77 (m, 1H), 5.23 (s, 2H), 3.90 (m, 2H), 3.57 (m, 2H), 3.32 (m, 4H), 2.51 (s, 6H); LCMS RT=2.83 min, [M+H]$^+$=552.2.

Example 12

N-(3-chloro-4-fluorophenyl)-7-[(2E)-4-piperidin-1-ylbut-2-enoyl]-5,6,7,8-tetrahydropyrido[4',3':4,5]thieno[2,3-d]pyrimidin-4-amine $^1$H-NMR (DMSO-d$_6$) δ 8.42 (s, 1H), 8.34 (m, 1H), 7.86 (m, 1H), 7.60 (m, 1H), 7.39 (t, 1H), 6.69 (m, 2H), 4.94 (s, 1H), 4.83 (s, 1H), 3.87 (m, 2H), 3.23 (m, 2H), 3.06 (m, 2H), 2.31 (m, 4H), 1.47 (m, 4H), 1.36 (m, 2H); LCMS RT=2.55 min, [M+H]$^+$=486.2.

Example 13

N-{3-chloro-4-[(3-fluorobenzyl)oxy]phenyl}-7-[(2E)-4-(diethylamino)but-2-enoyl]-5,6,7,8-tetrahydropyrido[4',3':4,5]thieno[2,3-d]pyrimidin-4-amine $^1$H-NMR (DMSO-d$_6$) δ 8.40 (s, 1H), 8.20 (m, 1H), 7.74 (m, 1H), 7.46 (d, J=7.83 Hz, 1H), 7.43 (m, 1H), 7.30 (m, 2H), 7.21 (d, J=9.2 Hz, 1H), 7.16 (t, 1H), 6.72 (m, 2H), 5.24 (s, 2H), 4.96 (s, 1H), 4.86 (s, 1H), 3.88 (m, 2H), 3.28 (m, 8H), 0.97 (m, 6H); LCMS RT=2.89 min, [M+H]$^+$=580.2.

Example 14

N-{3-chloro-4-[(3-fluorobenzyl)oxy]phenyl}-7-[(2E)-4-(4-methylpiperazin-1-yl)but-2-enoyl]-5,6,7,8-tetrahydropyrido[4',3':4,5]thieno[2,3-d]pyrimidin-4-amine $^1$H-NMR (DMSO-d$_6$) δ 8.40 (s, 1H), 8.22 (s, 1H), 7.78 (m, 1H), 7.54 (d, J=8.61 Hz, 1H), 7.49 (m, 1H), 7.34 (m, 2H), 7.24 (d, J=9.2 Hz, 1H), 7.20 (t, 1H), 6.73 (m, 2H), 5.27 (s, 2H), 4.97 (s, 1H), 4.87 (s, 1H), 3.94 (m, 2H), 3.38 (s, 3H), 3.26 (m, 2H), 3.14 (m, 2H), 2.37 (m, 8H); LCMS RT=3.00 min, [M+H]$^+$=607.3.

Example 15

N-(3-ethynylphenyl)-7-[(2E)-4-morpholin-4-ylbut-2-enoyl]-5,6,7,8-tetrahydropyrido[4',3':4,5]thieno[2,3-d]pyrimidin-4-amine $^1$H-NMR (CD$_2$Cl$_2$-d$_2$) δ 8.50 (s, 1H), 7.87 (m, 1H), 7.69 (m, 1H), 7.36 (t, 1H), 7.27 (d, J=7.6 Hz, 1H), 7.05 (d, J=38.9 Hz, 1H), 6.86 (m, 1H), 6.55 (m, 1H), 4.89 (m, 2H), 4.00 (m, 2H), 3.70 (m, 4H), 3.21 (s, 1H), 3.18 (m, 4H), 2.47 (m, 4H); LCMS RT=2.29 min, [M+H]$^+$=460.2.

Example 16

7-[(2E)-4-(diethylamino)but-2-enoyl]-N-(3-ethynylphenyl)-5,6,7,8-tetrahydropyrido[4',3':4,5]thieno[2,3-d]pyrimidin-4-amine $^1$H-NMR (CD$_2$Cl$_2$-d$_2$) δ 8.49 (s, 1H), 7.87 (m, 1H), 7.69 (m, 1H), 7.36 (t, 1H), 7.27 (d, J=7.6 Hz, 1H), 7.05 (d, J=38.9 Hz, 1H), 6.90 (m, 1H), 6.56 (m, 1H), 4.89 (m, 2H), 4.00 (m, 2H), 3.23 (m, 4H), 3.21 (s, 1H), 2.55 (m, 4H), 1.05 (m, 6H); LCMS RT=2.32 min, [M+H]$^+$=446.1.

Example 17

7-[(2E)-4-(dimethylamino)but-2-enoyl]-N-(3-ethynylphenyl)-5,6,7,8-tetrahydropyrido[4',3':4,5]thieno[2,3-d]pyrimidin-4-amine $^1$H-NMR (CD$_3$OD-d$_3$) δ 8.37 (s, 1H), 7.81 (m, 1H), 7.62 (m, 1H), 7.32 (t, 1H), 7.22 (d, J=7.6 Hz, 1H), 6.89-6.70 (m, 2H), 4.02 (t, 2H), 3.52 (s, 1H), 3.27 (m, 2H), 3.20 (m, 4H), 2.29 (s, 6H); LCMS RT=2.27 min, [M+H]$^+$=418.1.

The names, structures and certain characterizing data for the exemplary compounds of this invention are shown in Table 1 below.

TABLE 1

| Example | | LCMS RT (Min) | LCMS Ion [M + H]+ | IUPAC Name |
|---|---|---|---|---|
| 1 | 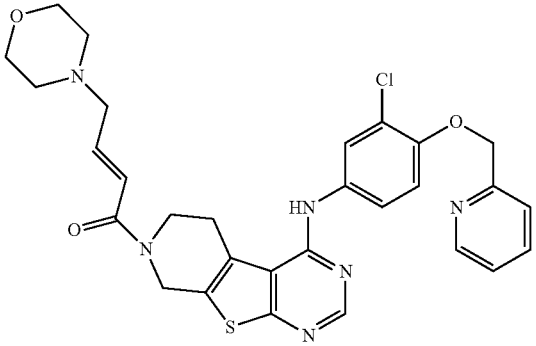 | 2.18 | 577.2 | N-[3-chloro-4-(pyridin-2-ylmethoxy)phenyl]-7-[(2E)-4-morpholin-4-ylbut-2-enoyl]-5,6,7,8-tetrahydropyrido[4',3,:4,5]thieno[2,3-d]pyrimidin-4-amine |
| 2 | 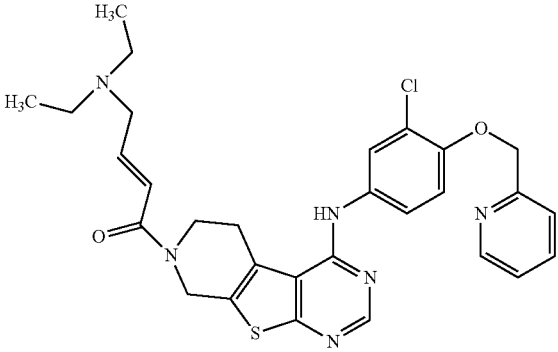 [SMILES: CCN(CC)C/C=C/C(=O)N1CCc2c(sc3ncnc(Nc4ccc(OCc5ccccn5)c(Cl)c4)c23)C1] | 2.37 | 563.2 | N-[3-chloro-4-(pyridin-2-ylmethoxy)phenyl]-7-[(2E)-4-(diethylamino)but-2-enoyl]-5,6,7,8-tetrahydropyrido[4'3':4,5]thieno[2,3-d]pyrimidin-4-amine |
| 3 | 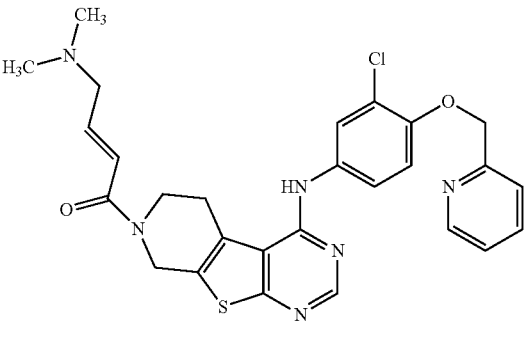 [SMILES: CN(C)C/C=C/C(=O)N1CCc2c(sc3ncnc(Nc4ccc(OCc5ccccn5)c(Cl)c4)c23)C1] | 2.31 | 536.2 | N-[3-chloro-4-(pyridin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine |
| 4 | 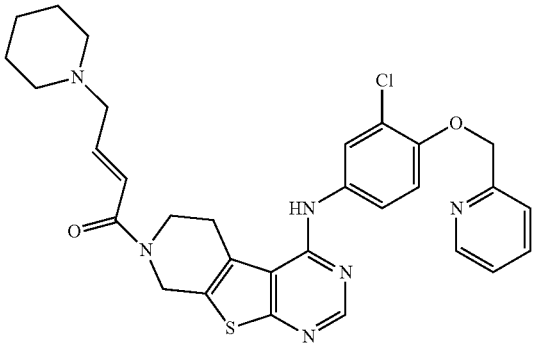 [SMILES: O=C(/C=C/CN1CCCCC1)N1CCc2c(sc3ncnc(Nc4ccc(OCc5ccccn5)c(Cl)c4)c23)C1] | 2.39 | 575.2 | N-[3-chloro-4-(pyridin-2-ylmethoxy)phenyl]-7-[(2E)-4-piperidin-1-ylbut-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 5 | | 2.32 | 590.2 | N-[3-chloro-4-(pyridin-2-ylmethoxy)phenyl]-7-[(2E)-4-(4-methylpiperazin-1-yl)but-2-enoyl]-5,6,7,8-tetrahydropyrido[4',3':4,5]thieno[2,3-d]pyrimidin-4-amine |
| 6 | | 2.4 | 488.1 | N-(3-chloro-4-fluorophenyl)-7-[(2E)-4-morpholin-4-ylbut-2-enoyl]-5,6,7,8-tetrahydropyrido[4',3':4,5]thieno[2,3-d]pyrimidin-4-amine |
| 7 | | 2.38 | 446 | N-(3-chloro-4-fluorophenyl)-7-[(2E)-4-(dimethylamino)but-2-enoyl]-5,6,7,8-tetrahydropyrido[4'3':4,5]thieno[2,3-d]pyrimidin-4-amine |
| 8 | | 2.32 | 501.1 | N-(3-chloro-4-fluorophenyl)-7-[(2E)-4-(4-methylpiperazin-1-yl)but-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 9 | 2.52 | 474.1 | N-(3-chloro-4-fluorophenyl)-7-[(2E)-4-(diethylamino)but-2-enoyl]-5,6,7,8-tetrahydropyrido[4',3':4,5]thieno[2,3-d]pyrimidin-4-amine |
| 10 | 2.86 | 594.3 | N-{3-chloro-4-[(3-fluorobenzyl)oxy]phenyl}-7-[(2E)-4-morpholin-4-ylbut-2-enoyl]-5(6,7,8-tetrahydropyrido[4'3':4,5]thieno[2,3-d]pyrimidin-4-amine |
| 11 | 2.83 | 552.2 | N-{3-chloro-4-[(3-fluorobenzyl)oxy]phenyl}-7-[(2E)-4-(dimethylamino)but-2-enoyl]-5,6,7,8-tetrahydropyrido[4',3':4,5]hieno[2,3-d]pyrimidin-4-amine |
| 12 | 2.55 | 486.2 | N-(3-chloro-4-fluorophenyl)-7-[(2E)-4-piperidin-1-ylbut-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 13 | 2.89 | 580.2 | N-{3-chloro-4-[(3-fluorobenzyl)oxy]phenyl}-7-[(2E)-4-(diethylamino)but-2-enoyl]-5,6,7,8-tetrahydropyrido[4',3':4,5]thieno[2,3-d]pyrimidin-4-amine |
| 14 | 3.00 | 607.3 | N-{3-chloro-4-[(3-fluorobenzyl)oxy]phenyl}-7-[(2E)-4-(4-methylpiperazin-1-yl)but-2-enoyl]-5,6,7,8-tetrahydropyrido[4',3':4,5]thieno[2,3-d]pyrimidin-4-amine |
| 15 | 2.29 | 460.2 | N-(3-ethynylphenyl)-7-[(2E)-4-morpholin-4-ylbut-2-enoyl]-5,6,7,8-tetrahydropyrido[4',3':4,5]thieno[2,3-d]pyrimidin-4-amine |
| 16 | 2.32 | 446.1 | 7-[(2E)-4-(diethylamino)but-2-enoyl]-N-(3-ethynylphenyl)-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 17 | | 2.27 | 418.1 | 7-[(2E)-4-(dimethylamino)but-2-enoyl]-N-(3-ethynylphenyl)-5,6,7,8-tetrahydropyrido[4',3':4,5]thieno[2,3-d]pyrimidin-4-amine |
| 18 | | 2.23 | 473.2 | N-(3-ethynylphenyl)-7-[(2E)-4-(4-methylpiperazin-1-yl)but-2-enoyl]-5,6,7,8-tetrahydropyrido[4',3':4,5]thieno[2,3-d]pyrimidin-4-amine |
| 19 | | 2.92 | 592.2 | N-{3-chloro-4-[(3-fluorobenzyl)oxy]phenyl}-7-[(2E)-4-piperidin-1-ylbut-2-enoyl]-5,6,7,8-tetrahydropyrido[4',3':4,5]thieno[2,3-d]pyrimidin-4-amine |
| 20 | | 2.45 | 458.2 | N-(3-ethynylphenyl)-7-[(2E)-4-piperidin-1-ylbut-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 21 | | 2.52 | 472.2 | N-(3-chloro-4-fluorophenyl)-7-[(2E)-4-pyrrolidin-1-ylbut-2-enoyl]-5,6,7,8-tetrahydropyrido[4',3':4,5]thieno[2,3-d]pyrimidin-4-amine |
| 22 | | 3.27 | 389.3 | 7-acryloyl-N-(3-chloro-4-fluorophenyl)-5,6,7,8-tetrahydropyrido[4',3':4,5]thieno[2,3-d]pyrimidin-4-amine |
| 23 | | 3.38 | 403.3 | 7-[(2E)-but-2-enoyl]-N-(3-chloro-4-fluorophenyl)-5,6,7,8-tetrahydropyrido[4',3':4,5]thieno[2,3-d]pyrimidin-4-amine |
| 24 | | 2.23 | 561.2 | N-[3-chloro-4-(pyridin-2-ylmethoxy)phenyl]-7-[(2E)-4-pyrrolidin-1-ylbut-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 25 | | 2.78 | 578.3 | N-{3-chloro-4-[(3-fluorobenzyl)oxy]phenyl}-7-[(2E)-4-pyrrolidin-1-ylbut-2-enoyl]-5,6,7,8-tetrahydropyrido[4',3':4,5]thieno[2,3-d]pyrimidin-4-amine |
| 26 | | 2.33 | 444.2 | N-(3-ethynylphenyl)-7-[(2E)-4-pyrrolidin-1-ylbut-2-enoyl]-5,6,7,8-tetrahydropyrido[4',3':4,5]thieno[2,3-d]pyrimidin-4-amine |
| 27 | | 3.18 | 361.2 | 7-acryloyl-N-(3-ethynylphenyl)-5,6,7,8-tetrahydropyrido[4',3':4,5]thieno[2,3-d]pyrimidin-4-amine |
| 28 | | 2.84 | 478.1 | 7-acryloyl-N-[3-chloro-4-(pyridin-2-ylmethoxy)phenyl]-5,6,7,8-tetrahydropyrido[4',3':4,5]thieno[2(3-d]pyrimidin-4-amine |

TABLE 1-continued

| Example | | LCMS RT (Min) | LCMS Ion [M + H]+ | IUPAC Name |
|---|---|---|---|---|
| 29 | 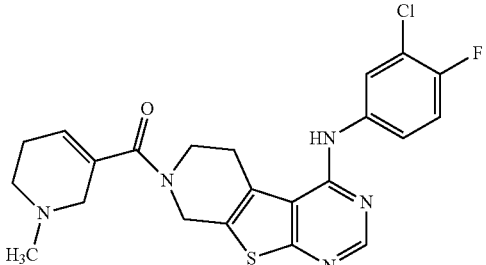 | 2.37 | 458.3 | N-(3-chloro-4-fluorophenyl)-7-[(1-methyl-1,2,5,6-tetrahydropyridin-3-yl)carbonyl]5,6,7,8-tetrahydropyrido[4',3':4,5]thieno[2,3-d]pyrimidin-4-amine |
| 30 | 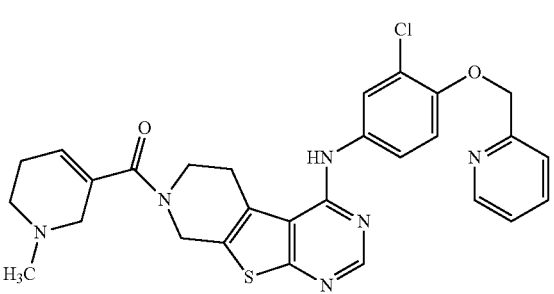 [SMILES: CN1CCC=C(C(=O)N2CCc3c(sc4ncnc(Nc5ccc(OCc6ccccn6)c(Cl)c5)c34)C2)C1] | 2.18 | 547.3 | N-[3-chloro-4-(pyridin-2-ylmethoxy)phenyl]-7-[(1-methyl-1,2,5,6-tetrahydropyridin-3-yl)carbonyl]-5,6,7,8-tetrahydropyrido[4',3':4,5]thieno[2,3-d]pyrimidin-4-amine |
| 31 | 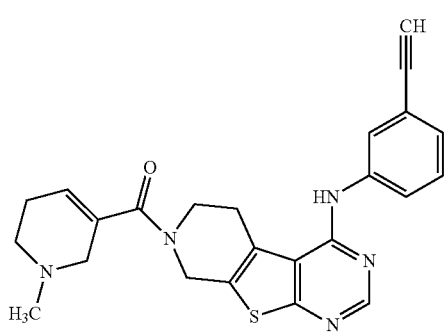 [SMILES: C#Cc1cccc(Nc2ncnc3sc4c(c23)CCN(C(=O)C2=CCCN(C)C2)C4)c1] | 2.43 | 430.1 | N-(3-ethynylphenyl)-7-[(1-methyl-1,2,5,6-tetrahydropyridin-3-yl)carbonyl]-5,6,7,8-tetrahydropyrido[4',3':4,5]thieno[2,3-d]pyrimidin-4-amine |
| 32 | 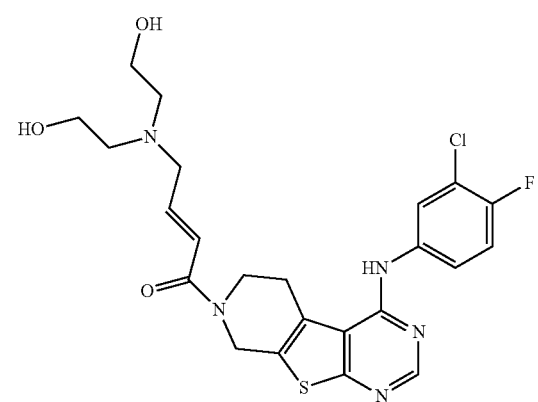 [SMILES: O=C(/C=C/CN(CCO)CCO)N1CCc2c(sc3ncnc(Nc4ccc(F)c(Cl)c4)c23)C1] | 2.87 | 506.1 | 2,2'-{[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]imino}diethanol |

TABLE 1-continued

| Example | LCMS RT (Min) | LCMS Ion [M + H]+ | IUPAC Name |
|---|---|---|---|
| 33 | 2.4 | 531.1 | 2-{4-[(2E)-4-{4-[(3-chloro-4-fluorophenyl)amino]-5,8-dihydropyrido[4'3':4,5]thieno[2,3-d]pyrimidin-7(6H)-yl}-4-oxobut-2-en-1-yl]piperazin-1-yl}ethanol |
| 34 | 2.93 | 469.1 | N-(3-chloro-4-fluorophenyl)-7-[(2E)-4-(1H-imidazol-1-yl)but-2-enoyl]-5,6,7,8-tetrahydropyrido[4',3':4,5]thieno[2,3-d]pyrimidin-4-amine |
| 35 | 2.64 | 490 | N-(3-chloro-4-fluorophenyl)-7-[(2E)-4-(1,3-thiazolidin-3-yl)but-2-enoyl]-5,6,7,8-tetrahydropyrido[4'3':4,5]thieno[2,3-d]pyrimidin-4-amine |
| 36 | 2.53 | 474.1 | N-(3-chloro-4-fluorophenyl)-7-{(2E)-4-[isopropyl(methyl)amino]but-2-enoyl}-5,6,7,8-tetrahydropyrido[4',3':4,5]thieno[2,3-d]pyrimidin-4-amine |
| 37 | 2.56 | 488.1 | N-(3-chloro-4-fluorophenyl)-7-{(2E)-4-[ethyl(isopropyl)amino]but-2-enoyl}-5,6,7,8-tetrahydropyrido[4'3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 38 | 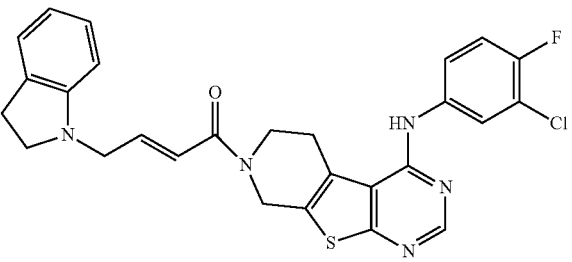 [SMILES: O=C(/C=C/CN1CCc2ccccc21)N1CCc2c(sc3ncnc(Nc4ccc(F)c(Cl)c4)c23)C1] | 3.76 | 520.2 | N-(3-chloro-4-fluorophenyl)-7-[(2E)-4-(2,3-dihydro-1H-indol-1-yl)but-2-enoyl]-5,6,7,8-tetrahydropyrido[4'3':4,5]thieno[2,3-d]pyrimidin-4-amine |
| 39 | 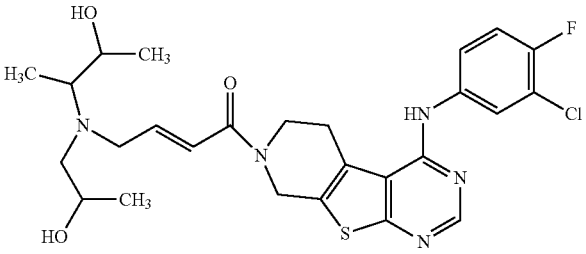 [SMILES: CC(O)CN(C/C=C/C(=O)N1CCc2c(sc3ncnc(Nc4ccc(F)c(Cl)c4)c23)C1)C(C)C(C)O] | 2.39 | 534.3 | 1,1'-{[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]imino}dipropan-2-ol |
| 40 | 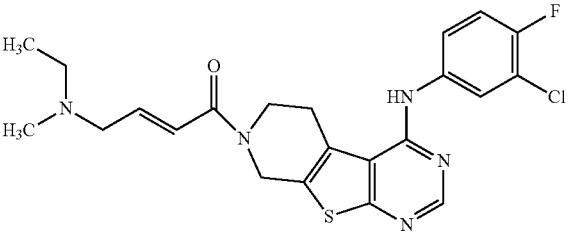 [SMILES: CCN(C)C/C=C/C(=O)N1CCc2c(sc3ncnc(Nc4ccc(F)c(Cl)c4)c23)C1] | 2.38 | 460.3 | N-(3-chloro-4-fluorophenyl)-7-{(2E)-4-[ethyl(methyl)amino]but-2-enoyl}-5,6,7,8-tetrahydropyrido[4',3':4,5]thieno[2,3-d]pyrimidin-4-amine |
| 41 | 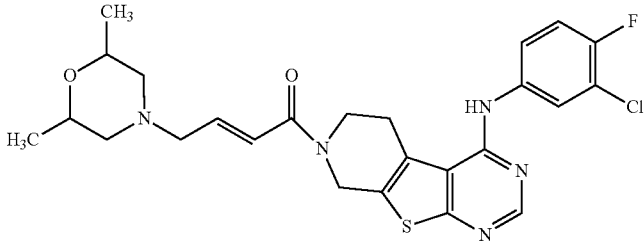 [SMILES: CC1CN(C/C=C/C(=O)N2CCc3c(sc4ncnc(Nc5ccc(F)c(Cl)c5)c34)C2)CC(C)O1] | 2.46 | 516.3 | N-(3-chloro-4-fluorophenyl)-7-[(2E)-4-(2,6-dimethylmorpholin-4-yl)but-2-enoyl]-5(6,7,8-tetrahydropyrido[4'3':4,5]thieno[2,3-d]pyrimidin-4-amine |
| 42 | 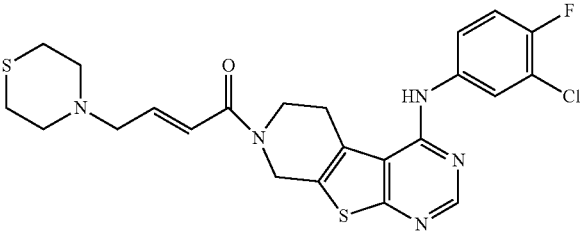 [SMILES: O=C(/C=C/CN1CCSCC1)N1CCc2c(sc3ncnc(Nc4ccc(F)c(Cl)c4)c23)C1] | 2.46 | 504.2 | N-(3-chloro-4-fluorophenyl)-7-[(2E)-4-thiomorpholin-4-ylbut-2-enoyl]-5,6,7,8-tetrahydropyrido[4',3':4,5]thieno[2,3-d]pyrimidin-4-amine |

TABLE 1-continued

| Example | Structure | LCMS RT (Min) | LCMS Ion [M + H]+ | IUPAC Name |
|---|---|---|---|---|
| 43 | | 2.53 | 595.2 | 2,2'-({(2E)-4-[4-{[3-chloro-4-(pyridin-2-ylmethoxy)phenyl]amino}-5,8-dihydropyrido[4',3':4,5]thieno[2,3-d]pyrimidin-7(6H)-yl]-4-oxobut-2-en-1-yl}imino)diethanol |
| 44 | | 3.37 | 609.2 | N-[3-chloro-4-(pyridin-2-ylmethoxy)phenyl]-7-[(2E)-4-(2,3-dihydro-1H-indol-1-yl)but-2-enoyl]-5,6,7,8-tetrahydropyrido[4',3':4,5]thieno[2,3-d]pyrimidin-4-amine |
| 45 | | 2.58 | 569.1 | 7-[(2E)-4-(1,4'-bipiperidin-1-yl)but-2-enoyl]-N-(3-chloro-4-fluorophenyl)-5,6,7,8-tetrahydropyrido[4',3':4,5]thieno[2,3-d]pyrimidin-4-amine |
| 46 | | 2.45 | 603.1 | N-[3-chloro-4-(pyridin-2-ylmethoxy)phenyl]-7-[(2E)-4-(3,5-dimethylpiperidin-1-yl)but-2-enoyl]-5,6,7,8-tetrahydropyrido[4',3':4,5]thieno[2,3-d]pyrimidin-4-amine |
| 47 | | 2.26 | 605.1 | (1-{(2E)-4-[4-{[3-chloro-4-(pyridin-2-ylmethoxy)phenyl]amino}-5,8-dihydropyrido[4',3':4,5]thieno[2,3-d]pyrimidin-7(6H)-yl]-4-oxobut-2-en-1-yl}piperidin-3-yl)methanol |

TABLE 1-continued

| Example | LCMS RT (Min) | LCMS Ion [M + H]+ | IUPAC Name |
|---|---|---|---|
| 48 | 2.34 | 589.1 | N-[3-chloro-4-(pyridin-2-ylmethoxy)phenyl]-7-[(2E)-4-(2,5-dimethylpyrrolidin-1-yl)but-2-enoyl]-5,6,7,8-tetrahydropyrido[4',3':4,5]thieno[2,3-d]pyrimidin-4-amine |
| 49 | 2.27 | 549.1 | N-(3-chloro-4-(pyridin-2-ylmethoxy)phenyl]-7-{(2E)-4-[ethyl(methyl)amino]but-2-enoyl}-5,6,7,8-tetrahydropyrido[4',3':4,5]thieno[2,3-d]pyrimidin-4-amine |
| 50 | 2.63 | 619.2 | 2-(1-{(2E)-4-[4-{[3-chloro-4-(pyridin-2-ylmethoxy)phenyl]amino}-5,8-dihydropyrido[4',3':4,5]thieno[2,3-d]pyrimidin-7(6H)-yl]-4-oxobut-2-en-1-yl}piperidin-2-yl)ethanol |
| 51 | 2.61 | 558.1 | N-[3-chloro-4-(pyridin-2-ylmethoxy)phenyl]-7-[(2E)-4-(1H-imidazol-1-yl)but-2-enoyl]-5,6,7,8-tetrahydropyrido[4',3':4,5]thieno[2,3-d]pyrimidin-4-amine |
| 52 | 2.24 | 623.6 | 1,1'-({(2E)-4-[4-{[3-chloro-4-(pyridin-2-ylmethoxy)phenyl]amino}-5,8-dihydropyrido[4',3':4,5]thieno[2,3-d]pyrimidin-7(6H)-yl]-4-oxobut-2-en-1-yl}imino)dipropan-2-ol |

TABLE 1-continued

| Example | | LCMS RT (Min) | LCMS Ion [M + H]+ | IUPAC Name |
|---|---|---|---|---|
| 53 | 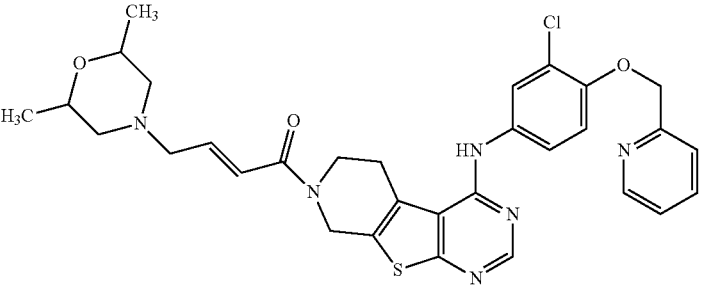 [SMILES: CC1CC(C)CN(C/C=C/C(=O)N2CCc3c(sc4ncnc(Nc5ccc(OCc6ccccn6)c(Cl)c5)c34)C2)C1] | 2.29 | 605.5 | N-[3-chloro-4-(pyridin-2-ylmethoxy)phenyl]-7-((2E)-4-(2,6-dimethylmorpholin-4-yl)but-2-enoyl]-5,6,7,8-tetrahydropyrido[4',3':4,5]thieno[2,3-d]pyrimidin-4-amine |
| 54 | 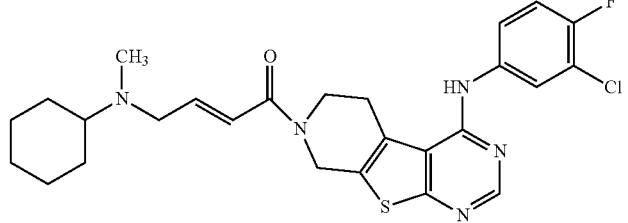 | 2.69 | 514.1 | N-(3-chloro-4-fluorophenyl)-7-{(2E)-4-[cyclohexyl(methyl)amino]but-2-enoyl}-5,6,7,8-tetrahydropyrido[4',3':4,5]thieno[2,3-d]pyrimidin-4-amine |
| 55 | 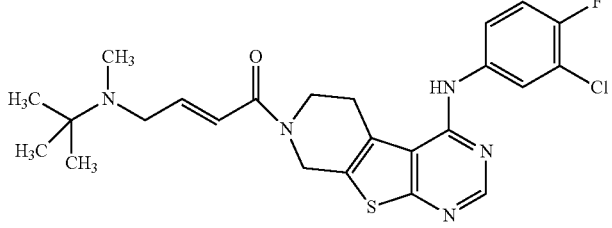 | 2.96 | 488.1 | 7-{(2E)-4-[tert-butyl(methyl)amino]but-2-enoyl}-N-(3-chloro-4-fluorophenyl)-5,6,7,8-tetrahydropyrido[4',3':4,5]thieno[2,3-d]pyrimidin-4-amine |
| 56 | 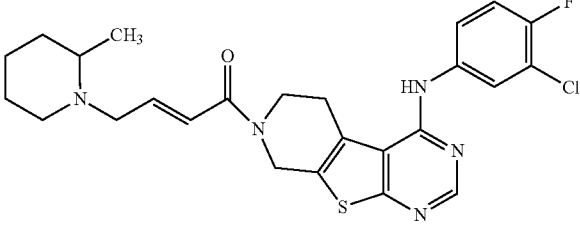 | 2.99 | 500.2 | N-(3-chloro-4-fluorophenyl)-7-[(2E)-4-(2-methylpiperidin-1-yl)but-2-enoyl]-5,6,7,8-tetrahydropyrido[4',3':4,5]thieno[2,3-d]pyrimidin-4-amine |
| 57 | 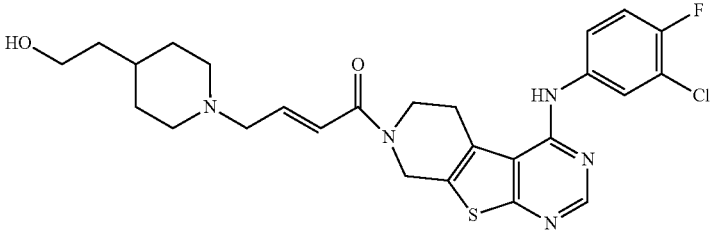 [SMILES: O=C(/C=C/CN1CCC(CCO)CC1)N1CCc2c(sc3ncnc(Nc4ccc(F)c(Cl)c4)c23)C1] | 2.48 | 530.1 | 2-{1-[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]piperidin-4-yl}ethanol |
| 58 | 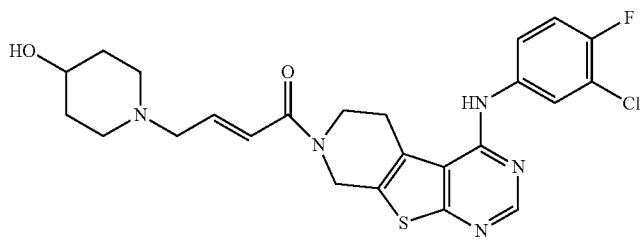 [SMILES: O=C(/C=C/CN1CCC(O)CC1)N1CCc2c(sc3ncnc(Nc4ccc(F)c(Cl)c4)c23)C1] | 2.46 | 502.1 | 1-[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]piperidin-4-ol |

TABLE 1-continued

| Example | LCMS RT (Min) | LCMS Ion [M + H]+ | IUPAC Name |
|---|---|---|---|
| 59 | 2.98 | 486.2 | N-(3-chloro-4-fluorophenyl)-7-[(2E)-4-(2-methylpyrrolidin-1-yl)but-2-enoyl]-5,6,7,8-tetrahydropyrido[4',3':4,5]thieno[2,3-d]pyrimidin-4-amine |
| 60 | 2.61 | 514.1 | N-(3-chloro-4-fluorophenyl)-7-[(2E)-4-(2,6-dimethylpiperidin-1-yl)but-2-enoyl]-5,6,7,8-tetrahydropyrido[4',3':4,5]thieno[2,3-d]pyrimidin-4-amine |
| 61 | 2.71 | 528.1 | N-(3-chloro-4-fluorophenyl)-7-{(2E)-4-[cyclohexyl(ethyl)amino]but-2-enoyl}-5,6,7,8-tetrahydropyrido[4',3':4,5]thieno[2,3-d]pyrimidin-4-amine |
| 62 | 3.05 | 620.2 | 2-(4-{(2E)-4-[4-{[3-chloro-4-(pyridin-2-ylmethoxy)phenyl]amino}-5,8-dihydropyrido[4',3':4,5]thieno[2,3-d]pyrimidin-7(6H)-yl]-4-oxobut-2-en-1-yl}piperazin-1-yl)ethanol |
| 63 | 3.11 | 563.2 | N-[3-chloro-4-(pyridin-2-ylmethoxy)phenyl]-7-{(2E)-4-[isopropyl(methyl)amino]but-2-enoyl}-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 64 | 2.41 | 589.1 | N-[3-chloro-4-(pyridin-2-ylmethoxy)phenyl]-7-[(2E)-4-(2-methylpiperidin-1-yl)but-2-enoyl]-5,6,7,8-tetrahydropyrido[4',3':4,5]thieno[2(3-d]pyrimidin-4-amine |
| 65 | 2.37 | 577 | 7-{(2E)-4-[tert-butyl(methyl)amino]but-2-enoyl}-N-[3-chloro-4-(pyridin-2-ylmethoxy)phenyl]-5,6,7,8-tetrahydropyrido[4',3':4,5]thieno[2,3-d]pyrimidin-4-amine |
| 66 | 2.42 | 577.1 | N-[3-chloro-4-(pyridin-2-ylmethoxy)phenyl]-7-{(2E)-4-[isobutyl(methyl)amino]but-2-enoyl}-5,6,7,8-tetrahydropyrido[4',3':4,5]thieno[2,3-d]pyrimidin-4-amine |
| 67 | 3.17 | 589.2 | N-[3-chloro-4-(pyridin-2-ylmethoxy)phenyl]-7-[(2E)-4-(3-methylpiperidin-1-yl)but-2-enoyl]-5,6,7,8-tetrahydropyrido[4',3':4,5]thieno[2,3-d]pyrimidin-4-amine |
| 68 | 2.4 | 589.1 | 7-[(2E)-4-azepan-1-ylbut-2-enoyl]-N-[3-chloro-4-(pyridin-2-ylmethoxy)phenyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 69 | | 2.5 | 516.1 | {1-[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]piperidin-3-yl}methanol |
| 70 | | 2.77 | 577.2 | N-[3-chloro-4-(pyridin-2-ylmethoxy)phenyl]-7-{(2E)-4-[ethyl(isopropyl)amino]but-2-enoyl}-5,6,7,8-tetrahydropyrido[4',3':4,5]thieno[2,3-d]pyrimidin-4-amine |
| 71 | | 2.64 | 500.1 | N-(3-chloro-4-fluorophenyl)-7-[(2E)-4-(3-methylpiperidin-1-yl)but-2-enoyl]-5,6,7,8-tetrahydropyrido[4',3':4,5]thieno[2,3-d]pyrimidin-4-amine |
| 72 | | 2.46 | 564.2 | N-[3-chloro-4-(pyrazin-2-ylmethoxy)phenyl]-7-[(2E)-4-(diethylamino)but-2-enoyl]-5,6,7,8-tetrahydropyrido[4',3':4,5]thieno[2,3-d]pyrimidin-4-amine |
| 73 | | 2.2 | 577.4 | N-{3-chloro-4-[(6-methylpyridin-2-yl)methoxy]phenyl}-7-[(2E)-4-(diethylamino)but-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 74 | 2.16 | 549.3 | N-{3-chloro-4-[(6-methylpyridin-2-yl)methoxy]phenyl}-7-[(2E)-4-(dimethylamino)but-2-enoyl]-5,6,7,8-tetrahydropyrido[4',3':4,5]thieno[2,3-d]pyrimidin-4-amine |
| 75 | 2.2 | 589.4 | N-{3-chloro-4-[(6-methylpyridin-2-yl)methoxy]phenyl}-7-[(2E)-4-piperidin-1-ylbut-2-enoyl]-5,6,7,8-tetrahydropyrido[4',3':4,5]thieno[2,3-d]pyrimidin-4-amine |
| 76 | 2.17 | 563.3 | N-{3-chloro-4-[(6-methylpyridin-2-yl)methoxy]phenyl}-7-{(2E)-4-[ethyl(methyl)amino]but-2-enoyl}-5,6,7,8-tetrahydropyrido[4',3':4,5]thieno[2,3-d]pyrimidin-4-amine |
| 77 | 2.19 | 577.3 | N-{3-chloro-4-[(6-methylpyridin-2-yl)methoxy]phenyl}-7-{(2E)-4-[isopropyl(methyl)amino]but-2-enoyl}-5,6,7,8-tetrahydropyrido[4',3':4,5]thieno[2,3-d]pyrimidin-4-amine |
| 78 | 2.18 | 575.3 | N-{3-chloro-4-[(6-methylpyridin-2-yl)methoxy]phenyl}-7-[(2E)-4-pyrrolidin-1-ylbut-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 79 | 2.4 | 576.4 | N-[3-chloro-4-(pyrazin-2-ylmethoxy)phenyl]-7-[(2E)-4-piperidin-1-ylbut-2-enoyl]-5,6,7,8-tetrahydropyrido[4'3':4,5]thieno[2,3-d]pyrimidin-4-amine |
| 80 | 2.35 | 578.4 | N-[3-chloro-4-(pyrazin-2-ylmethoxy)phenyl]-7-[(2E)-4-morpholin-4-ylbut-2-enoyl]-5,6,7,8-tetrahydropyrido[4'3':4,5]thieno[2,3-d]pyrimidin-4-amine |
| 81 | 2.42 | 550.4 | N-[3-chloro-4-(pyrazin-2-ylmethoxy)phenyl]-7-{(2E)-4-[ethyl(methyl)amino]but-2-enoyl}-5,6,7,8-tetrahydropyrido[4',3':4,5]thieno[2,3-d]pyrimidin-4-amine |
| 82 | 2.47 | 564.4 | N-[3-chloro-4-(pyrazin-2-ylmethoxy)phenyl]-7-{(2E)-4-[isopropyl(methyl)amino]but-2-enoyl}-5,6,7,8-tetrahydropyrido[4'3':4,5]thieno[2,3-d]pyrimidin-4-amine |
| 83 | 2.45 | 562.3 | N-[3-chloro-4-(pyrazin-2-ylmethoxy)phenyl]-7-[(2E)-4-pyrrolidin-1-ylbut-2-enoyl]-5,6,7,8-tetrahydropyrido[4'3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 84 | | 2.15 | 591.4 | N-{3-chloro-4-[(6-methylpyridin-2-yl)methoxy]phenyl}-7-[(2E)-4-morpholin-4-ylbut-2-enoyl]-5,6,7,8-tetrahydropyrido[4',3':4,5]thieno[2,3-d]pyrimidin-4-amine |
| 85 | | 2.31 | 536.3 | N-[3-chloro-4-(pyrazin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine |
| 86 | | 2.02 | 563.3 | N-[3-chloro-4-(pyridin-3-ylmethoxy)phenyl]-7-[(2E)-4-(diethylamino)but-2-enoyl]-5,6,7,8-tetrahydropyrido[4',3':4,5]thieno[2,3-d]pyrimidin-4-amine |
| 87 | | 2 | 535.3 | N-[3-chloro-4-(pyridin-3-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine |
| 88 | | 2.08 | 575.3 | N-[3-chloro-4-(pyridin-3-ylmethoxy)phenyl]-7-[(2E)-4-piperidin-1-ylbut-2-enoyl]-5,6,7,8-tetrahydropyrido[4'3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 89 | | 2.02 | 577.3 | N-[3-chloro-4-(pyridin-3-ylmethoxy)phenyl]-7-[(2E)-4-morpholin-4-ylbut-2-enoyl]-5,6,7,8-tetrahydropyrido[4',3':4,5]thieno[2,3-d]pyrimidin-4-amine |
| 90 | | 2.03 | 549.3 | N-[3-chloro-4-(pyridin-3-ylmethoxy)phenyl]-7-{(2E)-4-[ethyl(methyl)amino]but-2-enoyl}-5,6,7,8-tetrahydropyrido[4',3':4,5]thieno[2,3-d]pyrimidin-4-amine |
| 91 | | 2.07 | 563.3 | N-[3-chloro-4-(pyridin-3-ylmethoxy)phenyl]-7-{(2E)-4-[isopropyl(methyl)amino]but-2-enoyl}-5,6,7,8-tetrahydropyrido[4',3':4,5]thieno[2,3-d]pyrimidin-4-amine |
| 92 | | 2.86 | 542.2 | 7-[(2E)-4-(dimethylamino)but-2-enoyl]-N-[1-(3-fluorobenzyl)-1H-indazol-5-yl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 93 | 2.6 | 523.2 | N-(1-benzyl-1H-indol-5-yl)-7-[(2E)-4-(dimethylamino)but-2-enoyl]-5,6,7,8-tetrahydropyrido[4',3':4,5]thieno[2,3-d]pyrimidin-4-amine |
| 94 | 2.63 | 551.2 | N-(1-benzyl-1H-indol-5-yl)-7-[(2E)-4-(diethylamino)but-2-enoyl]-5,6,7,8-tetrahydropyrido[4',3':4,5]thieno[2,3-d]pyrimidin-4-amine |
| 95 | 2.52 | 552.2 | N-(1-benzyl-1H-indazol-5-yl)-7-[(2E)-4-(diethylamino)but-2-enoyl]-5,6,7,8-tetrahydropyrido[4',3':4,5]thieno[2,3-d]pyrimidin-4-amine |
| 96 | 2.64 | 563.2 | N-(1-benzyl-1H-indol-5-yl)-7-[(2E)-4-piperidin-1-ylbut-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 97 | | 2.47 | 524.5 | N-(1-benzyl-1H-indazol-5-yl)-7-[(2E)-4-(dimethylamino)but-2-enoyl]-5,6,7,8-tetrahydropyrido[4',3':4,5]thieno[2,3-d]pyrimidin-4-amine |
| 98 | | 2.96 | 541.2 | 7-[(2E)-4-(dimethylamino)but-2-enoyl]-N-[1-(3-fluorobenzyl)-1H-indol-5-yl]-5,6,7,8-tetrahydropyrido[4',3':4,5]thieno[2,3-d]pyrimidin-4-amine |
| 99 | | 2.98 | 570.3 | 7-[(2E)-4-(diethylamino)but-2-enoyl]-N-[1-(3-fluorobenzyl)-1H-indazol-5-yl]5,6,7,8-tetrahydropyrido[4',3':4,5]thieno[2,3-d]pyrimidin-4-amine |
| 100 | | 2.99 | 569.2 | 7-[(2E)-4-(diethylamino)but-2-enoyl]-N-[1-(3-fluorobenzyl)-1H-indol-5-yl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 101 | 2.97 | 582.3 | N-[1-(3-fluorobenzyl)-1H-indazol-5-yl]-7-[(2E)-4-piperidin-1-ylbut-2-enoyl]-5,6,7,8-(etrahydropyrido[4',3':4,5]thieno[2,3-d)pyrimidin-4-amine |
| 102 | 2.91 | 584.3 | N-[1-(3-fluorobenzyl)-1H-indazol-5-yl]-7-[(2E)-4-morpholin-4-ylbut-2-enoyl]-5,6,7,8-tetrahydropyrido[4',3':4,5]thieno[2,3-d]pyrimidin-4-amine |
| 103 | 2.87 | 566.3 | N-(1-benzyl-1H-indazol-5-yl)-7-[(2E)-4-morpholin-4-ylbut-2-enoyl]-5,6,7,8-tetrahydropyrido[4',3':4,5]thieno[2,3-d]pyrimidin-4-amine |
| 104 | 2.94 | 564.3 | N-(1-benzyl-1H-indazol-5-yl)-7-[(2E)-4-piperidin-1-ylbut-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 105 | 2.85 | 565.3 | N-(1-benzyl-1H-indol-5-yl)-7-[(2E)-4-morpholin-4-ylbut-2-enoyl]-5,6,7,8-tetrahydropyrido[4',3':4,5]thieno[2,3-d]pyrimidin-4-amine |
| 106 | 2.92 | 581.3 | N-[1-(3-fluorobenzyl)-1H-indol-5-yl]-7-[(2E)-4-piperidin-1-ylbut-2-enoyl]-5,6,7,8-tetrahydropyrido[4',3':4,5]thieno[2,3-d]pyrimidin-4-amine |
| 107 | 2.78 | 552.2 | N-(1-benzyl-1H-indazol-5-yl)-7-{(2E)-4-[isopropyl(methyl)amino]but-2-enoyl}-5,6,7,8-tetrahydropyrido[4',3':4,5]thieno[2,3-d]pyrimidin-4-amine |
| 108 | 2.99 | 583.3 | N-[1-(3-fluorobenzyl)-1H-indol-5-yl]-7-[(2E)-4-morpholin-4-ylbut-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 109 | 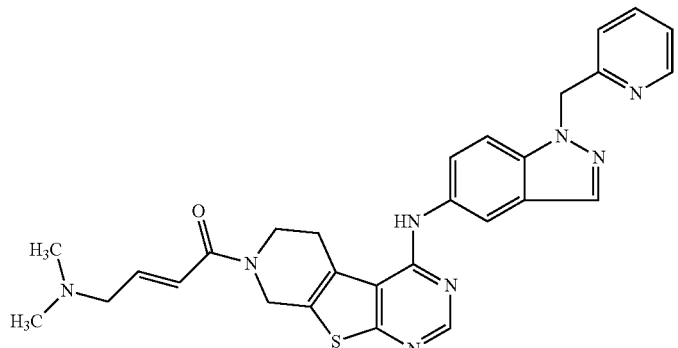 | 2.03 | 525.1 | 7-[(2E)-4-(dimethylamino)but-2-enoyl]-N-[1-(pyridin-2-ylmethyl)-1H-indazol-5-yl]-5,6,7,8-tetrahydropyrido[4',3':4,5]thieno[2,3-d]pyrimidin-4-amine |
| 110 | 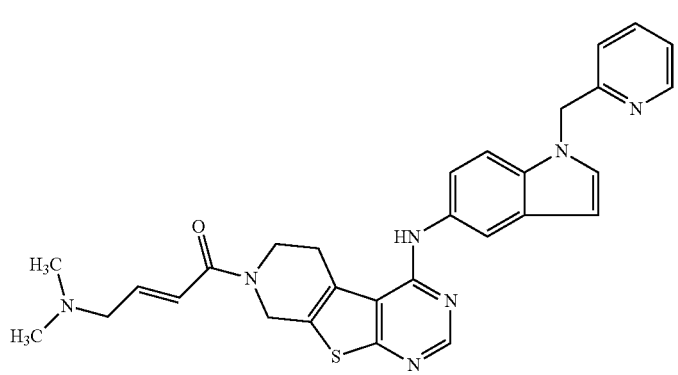 [SMILES: CN(C)C/C=C/C(=O)N1CCc2c(sc3ncnc(Nc4ccc5c(ccn5Cc5ccccn5)c4)c23)C1] | 2.13 | 553.1 | 7-[(2E)-4-(dimethylamino)but-2-enoyl]-N-[1-(pyridin-2-ylmethy)-1H-indol-5-yl]-5,6,7,8-tetrahydropyrido[4',3':4,5]thieno[2,3-d]pyrimidin-4-amine |
| 111 | 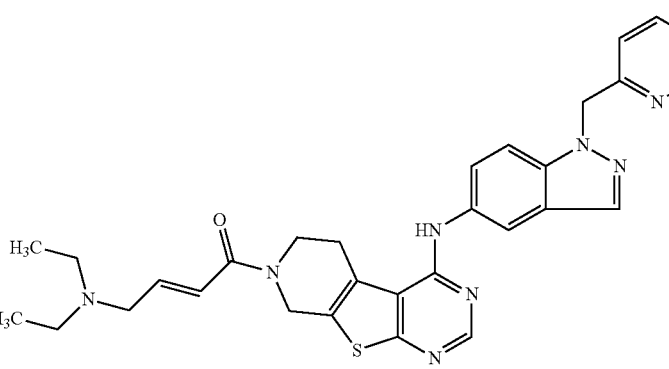 | 2.13 | 553.1 | 7-[(2E)-4-(diethylamino)but-2-enoyl]-N-[1-(pyridin-2-ylmethyl)-1H-indazol-5-yl]-5,6,7,8-tetrahydropyrido[4',3':4,5]thieno[2,3-d]pyrimidin-4-amine |
| 112 | 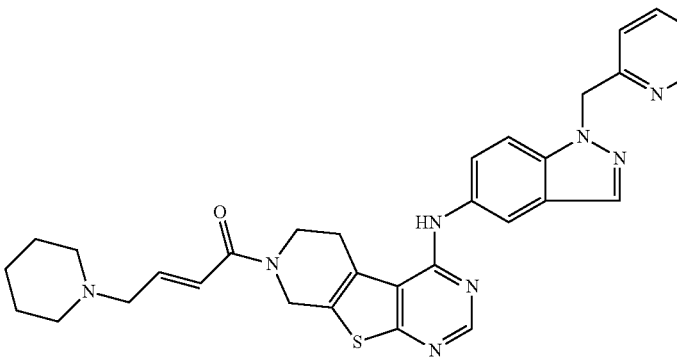 | 0.36 | 565.3 | 7-[(2E)-4-piperidin-1-ylbut-2-enoy]-N-[1-(pyridin-2-ylmethyl)-1H-indazol-5-yl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 113 | 2.49 | 567.3 | 7-[(2E)-4-morpholin-4-ylbut-2-enoyl]-N-[1-(pyridin-2-ylmethyl)-1H-indazol-5-yl]-5,6,7,8-tetrahydropyrido[4',3':4,5]thieno[2,3-d]pyrimidin-4-amine |
| 114 | 2.69 | 564.3 | 7-[(2E)-4-piperidin-1-ylbut-2-enoyl]-N-[1-(pyridin-2-ylmethyl)-1H-indol-5-yl]-5,6,7,8-tetrahydropyrido[4',3':4,5]thieno[2,3-d]pyrimidin-4-amine |
| 115 | 2.59 | 556.2 | 7-{(2E)-4-[ethyl(methyl)amino]but-2-enoyl}-N-[1-(3-fluorobenzyl)-1H-indazol-5-yl]-5,6,7,8-tetrahydropyrido[4',3':4,5]thieno[2,3-d]pyrimidin-4-amine |
| 116 | 1.07 | 553.3 | 7-{(2E)-4-[isopropyl(methyl)amino]but-2-enoyl}-N-[1-(pyridin-2-ylmethyl)-1H-indazol-5-yl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 117 | | 1.61 | 552.3 | 7-{(2E)-4-[isopropyl(methyl)amino]but-2-enoyl}-N-[1-(pyridin-2-ylmethyl)-1H-indol-5-yl]-5,6,7,8-tetrahydropyrido[4',3':4,5]thieno[2,3-d]pyrimidin-4-amine |
| 118 | | 3.3 | 551.3 | N-(1-benzyl-1H-indol-5-yl)-7-{(2E)-4-[isopropyl(methyl)amino]but-2-enoyl}-5,6,7,8-tetrahydropyrido[4',3':4,5]thieno[2,3-d]pyrimidin-4-amine |
| 119 | | 0.95 | 539.3 | 7-{(2E)-4-[ethyl(methyl)amino]but-2-enoyl}-N-[1-(pyridin-2-ylmethyl)-1H-indazol-5-yl]-5,6,7,8-tetrahydropyrido[4',3':4,5]thieno[2,3-d]pyrimidin-4-amine |
| 120 | | 1.1 | 566.3 | 7-[(2E)-4-morpholin-4-ylbut-2-enoyl]-N-[1-(pyridin-2-ylmethyl)-1H-indol-5-yl]-5,6,7,8-tetrahydropyrido[4',3':4,5]thieno[2,3-d]pyrimidin-4-amine |

TABLE 1-continued

| Example | Structure | LCMS RT (Min) | LCMS Ion [M + H]+ | IUPAC Name |
|---|---|---|---|---|
| 121 | | 1.28 | 552.3 | 7-[(2E)-4-(diethylamino)but-2-enoyl]-N-[1-(pyridin-2-ylmethyl)-1H-indol-5-yl]-5,6,7,8-tetrahydropyrido[4',3':4,5]thieno[2,3-d]pyrimidin-4-amine |
| 122 | | 3.34 | 569.3 | N-[1-(3-fluorobenzyl)-1H-indol-5-yl]-7-{(2E)-4-[isopropyl(methyl)amino]but-2-enoyl}-5,6,7,8-tetrahydropyrido[4',3':4,5]thieno[2,3-d]pyrimidin-4-amine |
| 123 | | 3.27 | 570.3 | N-[1-(3-fluorobenzyl)-1H-indazol-5-yl]-7-{(2E)-4-[isopropyl(methyl)amino]but-2-enoyl}-5,6,7,8-tetrahydropyrido[4',3':4,5]thieno[2,3-d]pyrimidin-4-amine |
| 124 | | 2.53 | 584.3 | 7-{(2E)-4-[tert-butyl(methyl)amino]but-2-enoyl}-N-[1-(3-fluorobenzyl)-1H-indazol-5-yl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 125 | | 2.65 | 583.4 | 7-{(2E)-4-[tert-butyl(methyl)amino]but-2-enoyl}-N-[1-(3-fluorobenzyl)-1H-indol-5-yl]-5,6,7,8-tetrahydropyrido[4',3':4,5]thieno[2,3-d]pyrimidin-4-amine |
| 126 | | 2.5 | 566.4 | N-(1-benzyl-1H-indazol-5-yl)-7-{(2E)-4-[tert-butyl(methyl)amino]but-2-enoyl}-5,6,7,8-tetrahydropyrido[4',3':4,5]thieno[2,3-d]pyrimidin-4-amine |
| 127 | | 2.11 | 538.3 | 7-{(2E)-4-[ethyl(methyl)amino]but-2-enoyl}-N-[l-(pyridin-ylmethyl)1H-indol-5-yl]-5,6,7,8-tetrahydropyrido[4',3':4,5]thieno[2,3-d]pyrimidin-4-amine |
| 128 | | 1.04 | 567.2 | 7-{(2E)-4-[tert-butyl(methyl)amino]but-2-enoyl}-N-[1-(pyridin-2-ylmethyl)-1H-indazol-5-yl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 129 | 1.41 | 566.2 | 7-{(2E)-4-[tert-butyl(methyl)amino]but-2-enoyl}-N-[1-(pyridin-2-ylmethyl)-1H-indol-5-yl]-5,6,7,8-tetrahydropyrido[4',3':4,5]thieno[2,3-d]pyrimidin-4-amine |
| 130 | 2.49 | 556.1 | 7-{(2E)-4-[ethyl(methyl)amino]but-2-enoyl}-N-[1-(3-fluorobenzyl)-1H-indol-5-yl]-5,6,7,8-tetrahydropyrido[4',3':4,5]thieno[2,3-d]pyrimidin-4-amine |
| 131 | 3.01 | 565.2 | N-(1-benzyl-1H-indol-5-yl)-7-{(2E)-4-[tert-butyl(methyl)amino]but-2-enoyl}-5,6,7,8-tetrahydropyrido[4',3':4,5]thieno[2,3-d]pyrimidin-4-amine |
| 132 | 2.37 | 587.1 | N-[3-chloro-4-(pyridin-2-ylmethoxy)phenyl]-7-(5-piperidin-1-ylpent-2-ynoyl)-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 133 | | 2.45 | 416.1 | 7-[4-(dimethylamino)but-2-ynoyl]-N-(3-ethynylphenyl)-5,6,7,8-tetrahydropyrido[4',3':4,5]thieno[2,3-d]pyrimidin-4-amine |
| 134 | | 2.56 | 444.1 | N-(3-chloro-4-fluorophenyl)-7-[4-(dimethylamino)but-2-ynoyl]-5,6,7,8-tetrahydropyrido[4',3':4,5]thieno[2,3-d]pyrimidin-4-amine |
| 135 | | 2.38 | 533.1 | N-[3-chloro-4-(pyridin-2-ylmethoxy)phenyl]-7-[4-(dimethylamino)but-2-ynoyl]-5,6,7,8-tetrahydropyrido[4',3':4,5]thieno[2,3-d]pyrimidin-4-amine |
| 136 | | 2.4 | 575.1 | N-[3-chloro-4-(pyridin-2-ylmethoxy)phenyl]-7-(4-morpholin-4-ylbut-2-ynoyl)-5,6,7,8-tetrahydropyrido[4',3':4,5]thieno[2,3-d]pyrimidin-4-amine |
| 137 | | 2.49 | 486.3 | N-(3-chloro-4-fluorophenyl)-7-(4-morpholin-4-ylbut-2-ynoyl)-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 138 | 2.39 | 458.3 | N-(3-ethynylphenyl)-7-(4-morpholin-4-ylbut-2-ynoyl)-5,6,7,8-tetrahydropyrido[4',3':4,5]thieno[2,3-d]pyrimidin-4-amine |
| 139 | 2.87 | 592.3 | N-{3-chloro-4-[(3-fluorobenzyl)oxy]phenyl}-7-(4-morpholin-4-ylbut-2-ynoyl)-5,6,7,8-tetrahydropyrido[4',3':4,5]thieno[2,3-d]pyrimidin-4-amine |
| 140 | 2.5 | 498.3 | N-(3-chloro-4-fluorophenyl)-7-(5-piperidin-1-ylpent-2-ynoyl)-5,6,7,8-tetrahydropyrido[4',3':4,5]thieno[2,3-d]pyrimidin-4-amine |
| 141 | 2.39 | 470.3 | N-(3-ethynylphenyl)-7-(5-piperidin-1-ylpent-2-ynoyl)-5,6,7,8-tetrahydropyrido[4',3':4,5]thieno[2,3-d]pyrimidin-4-amine |
| 142 | 2.96 | 604.1 | N-{3-chloro-4-[(3-fluorobenzyl)oxy]phenyl}-7-(5-piperidin-1-ylpent-2-ynoyl)-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 143 | 2.32 | 563.1 | N-[3-chloro-4-(pyridin-2-ylmethoxy)phenyl]-7-{2-[(diethylamino)methyl]acryloyl}-5,6,7,8-tetrahydropyrido[4',3':4,5]thieno[2,3-d]pyrimidin-4-amine |
| 144 | 2.27 | 577.1 | N-[3-chloro-4-(pyridin-2-ylmethoxy)phenyl]-7-2-(morpholin-ylmethyl)acryloyl]-5,6,7,8-tetrahydropyrido[4',3':4,5]thieno[2,3-d]pyrimidin-4-amine |
| 145 | 2.44 | 488.1 | N-(3-chloro-4-fluorophenyl)-7-[2-(morpholin-4-ylmethyl)acryloyl]-5,6,7,8-tetrahydropyrido[4',3':4,5]thieno[2,3-d]pyrimidin-4-amine |
| 146 | 3.08 | 594.2 | N-{3-chloro-4-[(3-fluorobenzyl)oxy]phenyl}-7-[2-(morpholin-4-ylmethyl)acryloyl]-5,6,7,8-tetrahydropyrido[4',3':4,5]thieno[2,3-d]pyrimidin-4-amine |
| 147 | 2.52 | 474.1 | N-(3-chloro-4-fluorophenyl)-7-{2-[(diethylamino)methyl]acryloyl}-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 148 | | 2.87 | 446.2 | 7-{2-[(diethylamino)methyl]acryloyl}-N-(3-ethynylphenyl)-5,6,7,8-tetrahydropyrido[4',3':4,5]thieno[2,3-d]pyrimidin-4-amine |
| 149 | | 3.11 | 580.3 | N-{3-chloro-4-[(3-fluorobenzyl)oxy]phenyl}-7-{2-[(diethylamino)methyl]acryloyl}-5,6,7,8-tetrahydropyrido[4',3':4,5]thieno[2,3-d]pyrimidin-4-amine |
| 150 | | 2.26 | 549.1 | N-[3-chloro-4-(pyridin-2-ylmethoxy)phenyl]-7-[(2E)-5-(dimethylamino)pent-2-enoyl]-5,6,7,8-tetrahydropyrido[4',3':4,5]thieno[2,3-d]pyrimidin-4-amine |
| 151 | | 2.95 | 433.1 | (3E)-5-{4-[(3-chloro-4-fluorophenyl)amino]-5,8-dihydropyrido[4',3':4,5]thieno[2,3-d]pyrimidin-7(6H)-yl}-5-oxopent-3-en-1-ol |
| 152 | | 2.93 | 486.2 | N-(3-chloro-4-fluorophenyl)-7-[(2E)-5-pyrrolidin-1-ylpent-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 153 | 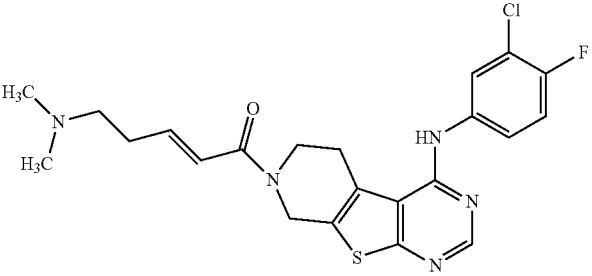 [SMILES: CN(C)CC/C=C/C(=O)N1CCc2c(sc3ncnc(Nc4ccc(F)c(Cl)c4)c23)C1] | 2.46 | 460 | N-(3-chloro-4-fluorophenyl)-7-[(2E)-5-(dimethylamino)pent-2-enoyl]-5(6,7,8-tetrahydropyrido[4',3':4,5]thieno[2,3-d]pyrimidin-4-amine |
| 154 | 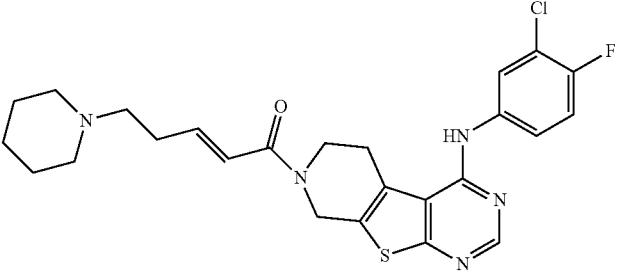 [SMILES: O=C(/C=C/CCN1CCCCC1)N1CCc2c(sc3ncnc(Nc4ccc(F)c(Cl)c4)c23)C1] | 2.56 | 500.1 | N-(3-chloro-4-fluorophenyl)-7-[(2E)-5-piperidin-1-ylpent-2-enoyl]-5,6,7,8-tetrahydropyrido[4',3':4,5]thieno[2,3-d]pyrimidin-4-amine |
| 155 | 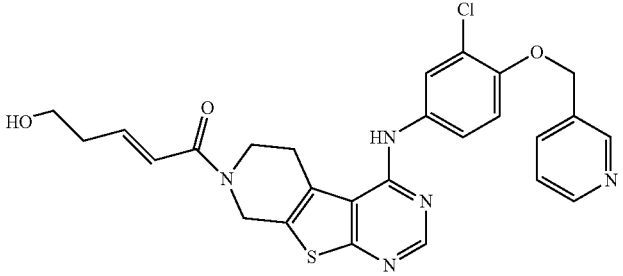 [SMILES: O=C(/C=C/CCO)N1CCc2c(sc3ncnc(Nc4ccc(OCc5cccnc5)c(Cl)c4)c23)C1] | 2.54 | 522 | (3E)-5-[4-{[3-chloro-4-(pyridin-2-ylmethoxy)phenyl]amino}-5,8-dihydropyrido[4',3':4,5]thieno[2,3-d]pyrimidin-7(6H)-yl]-5-oxopent-3-en-1-ol |
| 156 | 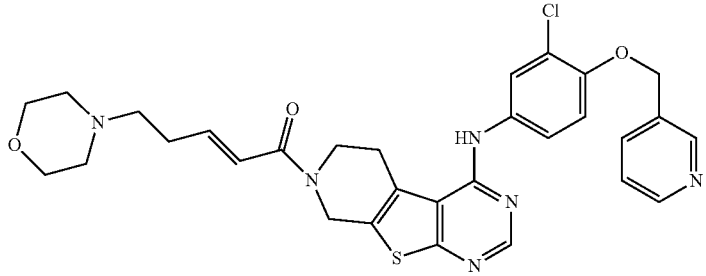 [SMILES: O=C(/C=C/CCN1CCOCC1)N1CCc2c(sc3ncnc(Nc4ccc(OCc5cccnc5)c(Cl)c4)c23)C1] | 2.17 | 591.4 | N-[3-chloro-4-(pyridin-2-ylmethoxy)phenyl]-7-[(2E)-5-morpholin-4-ylpent-2-enoyl]-5,6,7,8-tetrahydropyrido[4',3':4,5]thieno[2,3-d]pyrimidin-4-amine |
| 157 | 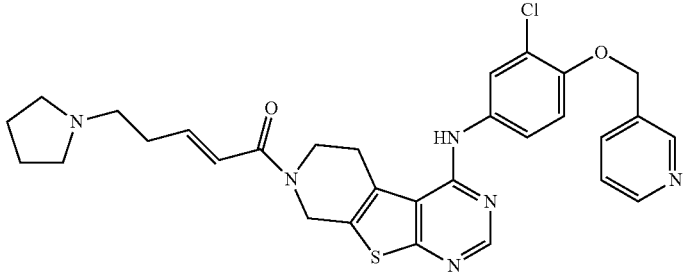 [SMILES: O=C(/C=C/CCN1CCCC1)N1CCc2c(sc3ncnc(Nc4ccc(OCc5cccnc5)c(Cl)c4)c23)C1] | 2.31 | 575.1 | N-[3-chloro-4-(pyridin-2-ylmethoxy)phenyl]-7-[(2E)-5-pyrrolidin-1-ylpent-2-enoyl]-5,6,7,8-tetrahydropyrido[4',3':4,5]thieno[2,3-d]pyrimidin-4-amine |

| Example | | LCMS RT (Min) | LCMS Ion [M + H]+ | IUPAC Name |
|---|---|---|---|---|
| 158 | | 2.33 | 589.1 | N-[3-chloro-4-(pyridin-2-ylmethoxy)phenyl]-7-[(2E)-5-piperidin-1-ylpent-2-enoyl]-5,6,7,8-tetrahydropyrido[4',3':4,5]thieno[2,3-d]pyrimidin-4-amine |
| 159 | | 2.29 | 563.1 | N-[3-chloro-4-(pyridin-2-ylmethoxy)phenyl]-7-{(2E)-5-[ethyl(methyl)amino]pent-2-enoyl}-5,6,7,8-tetrahydropyrido[4',3':4,5]thieno[2,3-d]pyrimidin-4-amine |
| 160 | | 2.49 | 472 | N-(3-bromophenyl)-7-[(2E)-4-(dimethylamino)but-2-enoyl]-5,6,7,8-tetrahydropyrido[4',3':4,5]thieno[2,3-d]pyrimidin-4-amine |
| 161 | | 2.06 | 394.3 | 7-[(2E)-4-(dimethylamino)but-2-enoyl]-N-phenyl-5,6,7,8-tetrahydropyrido[4',3':4,5]thieno[2,3-d]pyrimidin-4-amine |
| 162 | | 2.29 | 430.1 | N-(2,4-difluorophenyl)-7-[(2E)-4-(dimethylamino)but-enoyl]-5,6,7,8-tetrahydropyrido[4',3':4,5]thieno[2,3-d]pyrimidin-4-amine |
| 163 | | 2.52 | 428.1 | N-(4-chlorophenyl)-7-[(2E)-4-(dimethylamino)but-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 164 | 2.83 | 428.1 | N-(3-chlorophenyl)-7-[(2E)-4-(dimethylamino)but-2-enoyl]-5,6,7,8-tetrahydropyrido[4',3':4,5]thieno[2,3-d]pyrimidin-4-amine |
| 165 | 2.6 | 462.3 | N-(3,4-dichlorophenyl)-7-[(2E)-4-(dimethylamino)but-2-enoyl]-5,6,7,8-tetrahydropyrido[4',3':4,5]thieno[2,3-d]pyrimidin-4-amine |
| 166 | 2.23 | 426.3 | 7-[(2E)-4-(dimethylamino)but-2-enoyl]-N-(5-fluoro-2-methylphenyl)-5,6,7,8-tetrahydropyrido[4',3':4,5]thieno[2,3-d]pyrimidin-4-amine |
| 167 | 2.38 | 422.4 | 7-[(2E)-4-(dimethylamino)but-2-enoyl]-N-(3,5-dimethylphenyl)-5,6,7,8-tetrahydropyrido[4',3':4,5]thieno[2,3-d]pyrimidin-4-amine |
| 168 | 2.28 | 438.3 | 7-[(2E)-4-(dimethylamino)but-2-enoyl]-N-(3-ethoxyphenyl)-5,6,7,8-tetrahydropyrido[4',3':4,5]thieno[2,3-d]pyrimidin-4-amine |
| 169 | 2.1 | 408.3 | N-benzyl-7-[(2E)-4-(dimethylamino)but-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 170 | | 2.39 | 446.2 | N-(4-chloro-2-fluorophenyl)-7-[(2E)-4-(dimethylamino)but-2-enoyl]-5,6,7,8-tetrahydropyrido[4',3':4,5]thieno[2,3-d]pyrimidin-4-amine |
| 171 | | 2.27 | 426.3 | 7-[(2E)-4-(dimethylamino)but-2-enoyl]-N-(2-fluoro-4-methylphenyl)-5,6,7,8-tetrahydropyrido[4',3':4,5]thieno[2,3-d]pyrimidin-4-amine |
| 172 | | 2.68 | 507.9 | N-(4-bromo-3-chlorophenyl)-7-[(2E)-4-(dimethylamino)but-2-enoyl]-5,6,7,8-tetrahydropyrido[4',3':4,5]thieno[2,3-d]pyrimidin-4-amine |
| 173 | | 2.49 | 453.1 | 2-chloro-4-({7-[(2E)-4-(dimethylamino)but-2-enoyl]-5,6,7,8-tetrahydropyrido[4',3':4,5]thieno[2,3-d]pyrimidin-4-yl}amino)benzonitrile |
| 174 | | 2.69 | 462 | N-(3,5-dichlorophenyl)-7-[(2E)-4-(dimethylamino)but-2-enoyl]-5,6,7,8-tetrahydropyrido[4',3':4,5]thieno[2,3-d]pyrimidin-4-amine |
| 175 | | 2.09 | 412.3 | 7-[(2E)-4-(dimethylamino)but-2-enoyl]-N-(4-fluorophenyl)-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 176 | | 2.4 | 492.2 | N-(3-bromo-4-fluorophenyl)-7-[(2E)-4-(dimethylamino)but-2-enoyl]-5,6,7,8-tetrahydropyrldo[4',3':4,5]thieno[2,3-d]pyrimidin-4-amine |
| 177 | | 2.55 | 408.2 | 7-[(2E)-4-(dimelhylamino)but-2-enoyl]-N-(3-methylphenyl)-5,6,7,8-tetrahydropyrido[4',3':4,5]thieno[2,3-d]pyrimidin-4-amine |
| 178 | | 2.7 | 422.2 | 7-[(2E)-4-(dimethylamino)but-2-enoyl]-N-(3-ethylphenyl)-5,6,7,8-tetrahydropyrido[4',3':4,5]thieno[2,3-d]pyrimidin-4-amine |
| 179 | | 2.42 | 424.2 | 7-[(2E)-4-(dimethylamino)but-2-enoyl]-N-(3-methoxyphenyl)-5,6,7,8-tetrahydropyrido[4',3':4,5]thieno[2,3-d]pyrimidin-4-amine |
| 180 | | 2.82 | 446.1 | N-(4-chloro-3-fluorophenyl)-7-[(2E)-4-(dimethylamino)but-2-enoyl]-5,6,7,8-tetrahydropyrido[4',3':4,5]thieno[2,3-d]pyrimidin-4-amine |
| 181 | | 2.93 | 446.1 | N-(3-chloro-5-fluorophenyl)-7-[(2E)-4-(dimethylamino)but-2-enoyl]-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 182 | (structure) | 2.45 | 426.2 | 7-[(2E)-4-(dimethylamino)but-2-enoyl]-N-(4-fluoro-3-methylphenyl)-5,6,7,8-tetrahydropyrido[4',3':4,5]thieno[2,3-d]pyrimidin-4-amine |
| 183 | (structure) | 2.8 | 442.2 | N-(4-chloro-3-methylphenyl)-7-[(2E)-4-(dimethylamino)but-2-enoyl]-5,6,7,8-tetrahydropyrido[4',3':4,5]thieno[2,3-d]pyrimidin-4-amine |
| 184 | (structure) | 2.82 | 474.1 | N-(4-bromophenyl)-7-[(2E)-4-(dimethylamino)but-2-enoyl]-5,6,7,8-tetrahydropyrido[4',3':4,5]thieno[2,3-d]pyrimidin-4-amine. |
| 185 | (structure) | 2.81 | 434.2 | N-(2,3-dihydro-1H-inden-5-yl)-7-[(2E)-4-(dimethylamino)but-2-enoyl]-5,6,7,8-tetrahydropyrido[4',3':4,5]thieno[2,3-d]pyrimidin-4-amine |
| 186 | (structure) | 2.52 | 486.2 | N-(3-bromophenyl)-7-{(2E)-4-[ethyl(methyl)amino]but-2-enoyl}-5,6,7,8-tetrahydropyrido[4',3':4,5]thieno[2,3-d]pyrimidin-4-amine |
| 187 | (structure) | 2.72 | 490.3 | N-(3,4-dichlorophenyl)-7-{(2E)-4-[isopropyl(methyl)amino]but-2-enoyl}-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 188 | 2.77 | 490.3 | N-(3,4-dichlorophenyl)-7-[(2E)-4-(diethylamino)but-2-enoyl]-5,6,7,8-tetrahydropyrido[4',3':4,5]thieno[2,3-d]pyrimidin-4-amine |
| 189 | 2.61 | 500.3 | N-(3-bromophenyl)-7-{(2E)-4-[isopropyl(methyl)amino]but-2-enoyl}-5,6,7,8-tetrahydropyrido[4',3':4,5]thieno[2,3-d]pyrimidin-4-amine |
| 190 | 2.65 | 476.1 | N-(3,4-dichlorophenyl)-7-{(2E)-4-[ethyl(methyl)amino]but-2-enoyl}-5,6,7,8-tetrahydropyrido[4',3':4,5]thieno[2,3-d]pyrimidin-4-amine |
| 191 | 2.7 | 504.3 | N-(3,4-dichlorophenyl)-7-[{2E)-4-morpholin-4-ylbut-2-enoyl]-5,6,7,8-tetrahydropyrido[4',3':4,5]thieno[2,3-d]pyrimidin-4-amine |
| 192 | 2.73 | 488.3 | N-(3,4-dichlorophenyl)-7-[(2E)-4-pyrrolidin-1-ylbut-2-enoyl]-5,6,7,8-tetrahydropyrido[4',3':4,5]thieno[2,3-d]pyrimidin-4-amine |
| 193 | 2.56 | 514.3 | N-(3-bromophenyl)-7-[(2E)-4-morpholin-4-ylbut-2-enoyl]-5,6,7,8-tetrahydropyrido[4',3':4,5]thieno[2,3-d]pyrimidin-4-amine |

TABLE 1-continued

| Example | LCMS RT (Min) | LCMS Ion [M + H]+ | IUPAC Name |
|---|---|---|---|
| 194 | 2.85 | 498.2 | N-(3-bromophenyl)-7-[(2E)-4-pyrrolidin-1-ylbut-2-enoyl]-5,6,7,8-tetrahydropyrido[4',3':4,5]thieno[2,3-d]pyrimidin-4-amine |
| 195 | 3.05 | 502.2 | N-(3,4-dichlorophenyl)-7-[(2E)-4-piperidin-1-ylbut-2-enoyl]-5,6,7,8-tetrahydropyrido[4',3':4,5]thieno[2,3-d]pyrimidin-4-amine |
| 196 | 2.92 | 512.2 | N-(3-bromophenyl)-7-[(2E)-4-piperidin-1-ylbut-2-enoyl]-5,6,7,8-tetrahydropyrido[4',3':4,5]thieno[2,3-d]pyrimidin-4-amine |
| 197 | 2.51 | 500.1 | N-(3-bromophenyl)-7-[(2E)-4-(diethylamino)but-2-enoyl]-5,6,7,8-tetrahydropyrido[4',3':4,5]thieno[2,3-d]pyrimidin-4-amine |
| 198 | 2.55 | 513.9 | N-(3-bromophenyl)-7-{(2E)-4-[tert-butyl(methyl)amino]but-2-enoyl}-5,6,7,8-tetrahydropyrido[4',3':4,5]thieno[2,3-d]pyrimidin-4-amine |
| 199 | 2.69 | 503.9 | 7-{(2E)-4-[tert-butyl(methyl)amino]but-2-enoyl}-N-(3,4-dichlorophenyl)-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 200 | 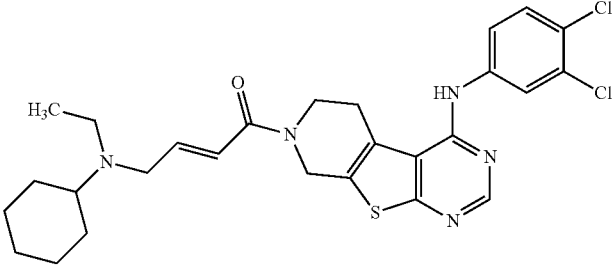 [SMILES: CCN(C/C=C/C(=O)N1CCc2c(sc3ncnc(Nc4ccc(Cl)c(Cl)c4)c23)C1)C1CCCCC1] | 2.84 | 544.1 | 7-{(2E)-4-[cyclohexyl(ethyl)amino]but-2-enoyl}-N-(3,4-dichlorophenyl)-5,6,7,8-tetrahydropyrido[4',3':4,5]thieno[2,3-d]pyrimidin-4-amine |
| 201 | 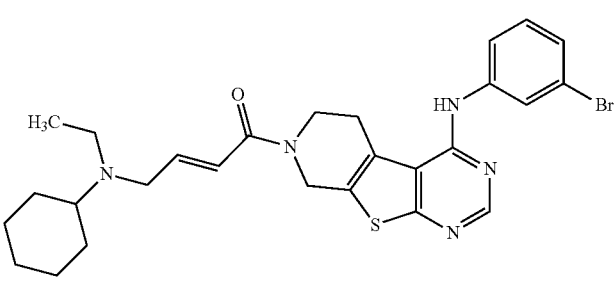 [SMILES: CCN(C/C=C/C(=O)N1CCc2c(sc3ncnc(Nc4cccc(Br)c4)c23)C1)C1CCCCC1] | 3.08 | 554.2 | N-(3-bromophenyl)-7-{(2E)-4-[cyclohexyl(ethyl)amino]but-2-enoyl}-5,6,7,8-tetrahydropyrido[4',3':4,5]thieno[2,3-d]pyrimidin-4-amine |
| 202 | 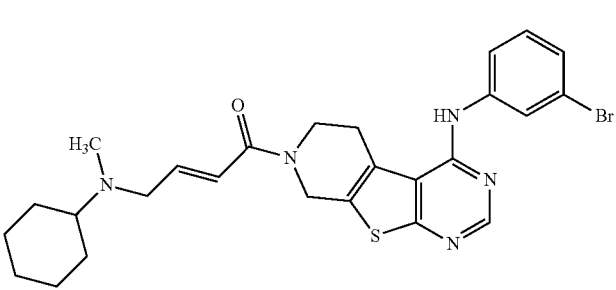 [SMILES: CN(C/C=C/C(=O)N1CCc2c(sc3ncnc(Nc4cccc(Br)c4)c23)C1)C1CCCCC1] | 2.59 | 540.3 | N-(3-bromophenyl)-7-{(2E)-4-[cyclohexyl(methyl)amino]but-2-enoyl}-5,6,7,8-tetrahydropyrido[4',3':4,5]thieno[2,3-d]pyrimidin-4-amine |
| 203 | 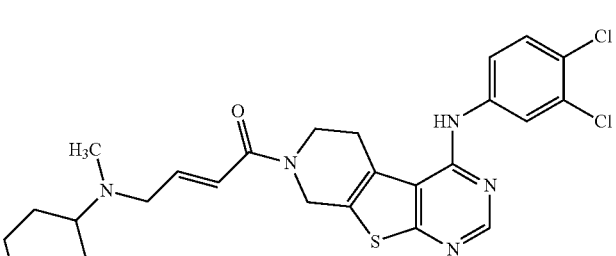 | 2.73 | 530.3 | 7-{(2E)-4-[cyclohexyl(methyl)amino]but-2-enoyl}-N-(3,4-dichlorophenyl)-5,6,7,8-tetrahydropyrido[4',3':4,5]thieno[2,3-d]pyrimidin-4-amine |
| 204 | 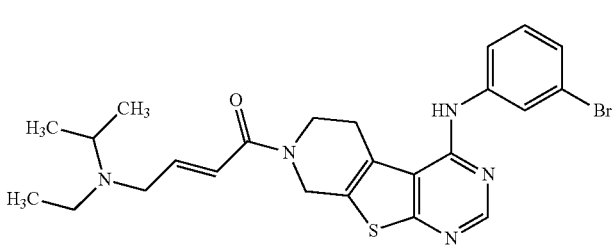 [SMILES: CCN(C/C=C/C(=O)N1CCc2c(sc3ncnc(Nc4cccc(Br)c4)c23)C1)C(C)C] | 2.53 | 514.3 | N-(3-bromophenyl)-7-{(2E)-4-[ethyl(isopropyl)amino]but-2-enoyl}-5,6,7,8-tetrahydropyrido[4',3':4,5]thieno[2,3-d]pyrimidin-4-amine |

TABLE 1-continued

| Example | | LCMS RT (Min) | LCMS Ion [M + H]+ | IUPAC Name |
|---|---|---|---|---|
| 205 | | 2.67 | 504.3 | N-(3,4-dichlorophenyl)-7-{(2E)-4-[ethyl(isopropyl)amino]but-2-enoyl}-5,6,7,8-tetrahydropyrido[4',3':4,5]thieno[2,3-d]pyrimidin-4-amine |
| 206 | | 2.65 | 502.3 | N-(3,4-dichlorophenyl)-7-[(2E)-4-(2-methylpyrrolidin-1-yl)but-2-enoyl]-5,6,7,8-tetrahydropyrido[4',3':4,5]thieno[2,3-d]pyrimidin-4-amine |
| 207 | | 2.5 | 512.3 | N-(3-bromophenyl)-7-[(2E)-4-(2-methylpyrrolidin-1-yl)but-2-enoyl]-5,6,7,8-tetrahydropyrido[4',3':4,5]thieno[2,3-d]pyrimidin-4-amine |
| 208 | | 2.56 | 528.3 | N-(3-bromophenyl)-7-[(2E)-4-(diisopropylamino)but-2-enoyl]-5,6,7,8-tetrahydropyrido[4',3':4,5]thieno[2,3-d]pyrimidin-4-amine |
| 209 | | 2.72 | 518.3 | N-(3,4-dichlorophenyl)-7-[(2E)-4-(diisopropylamino)but-2-enoyl]-5,6,7,8-tetrahydropyrido[4',3':4,5]thieno[2,3-d]pyrimidin-4-amine |
| 210 | | 2.69 | 516.4 | N-(3,4-dichlorophenyl)-7-[(2E)-4-(2-methylpiperidin-1-yl)but-2-enoyl]-5,6,7,8-tetrahydropyrido[4',3':4,5]thieno[2,3-d]pyrimidin-4-amine |

B. Physiological Activity

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays.

Many of the compounds and compositions described herein, exhibit anti-proliferative activity with $IC_{50} \leqq 50$ µM in either of the following specified cell lines and are thus useful to prevent or treat the disorders associated with hyper-proliferation. The following assay is one of the methods by which compound activity relating to treatment of the disorders identified herein can be determined.

The tumor cell proliferation assay used to test the compounds of the present invention involves a readout called Cell Titer-Glow® Luminescent Cell Viability Assay developed by Promega® (Cunningham, BA "A Growing Issue: Cell Proliferation Assays, Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay in A431 and BT474 Cell Lines

A431 cells [human epidermoid carcinoma, ATCC # HTB-20, overexpressing HER1 (EGFR, ErbB1)] and N87 [human gastric carcinoma, ATCC # CRL-1555, overexpressing HER2 (ErbB2) and HER1 (EGFR, ErbB1)] were plated at a density of $2.5 \times 10^3$ cells/well in 96 well black-clear bottom tissue culture plates in RPMI media with 10% Fetal Bovine Serum and incubated at 37° C. Twenty-four hours later, test compounds are added at a final concentration range from as high 100 µm to as low 64 µM depend on the activities of the tested compounds in serial dilutions at a final DMSO concentration of 0.1%. Cells were incubated for 72 hours at 37° C. in complete growth media after addition of the test compound. After 72 hours of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR2 using Luminescence protocol, and analyzed with Analyze5 software to generate $IC_{50}$ values. Representative compounds of this invention showed inhibition of tumor cell proliferation in this assay.

Activities in A431 cell lines: Examples 1-7, 9-22, 26, 59, 92, 105-108, 110, 114, 115, 118, 123, 124, 126, 150, 157-158, 160, 194-199, 205, and 206 have $IC_{50}$ below 200 nM; Examples 8, 24, 25, 36, 40, 41, 46, 47, 49, 51, 54, 56, 60-69, 85, 87, 93-95, 97-104, 109, 111-113, 116, 117, 119-122, 125, and 125-129, 132-135, 138-143, 147, 149, 159, 161-165, 170, 172, 176, 180, 182-192, 200-204, and 207-209 have $IC_{50}$ in the range of 200-1000 nM; 23, 27-39, 42-45, 48, 50, 52, 53, 57, 58, 70, 72-84, 86, 88, 89, 90, 91, 96, 136, 137, 144-146, 148, 151-155, 166-169, 171, 173-175, 177-179, 181, and 193 have $IC_{50}$ in the range of 1 uM-10 uM.

Activities in N87 cell lines: Examples 1-22, 24-28, 32, 33, 36, 37, 39-51, 53-70, 72-129, 131-144, 146-150, 152-165, and 167-210 have $IC_{50}$ below 200 nM; Examples 23, 29, 30, 31, 35, 38, 52, 145, 151, and 166 have $IC_{50}$ in the range of 200-5000 nM.

In Vitro Tumor Cell Proliferation Assay in H1975 Cells

H1975 cells [human non small cell lung carcinoma, ATCC # CRL-5908, expressing mutant HER1 [(EGFR, ErbB1) (L858R,T790M] were plated at a density of $3 \times 10^3$ cells/well in 96 well black-clear bottom tissue culture plates in RPMI media with 10% Fetal Bovine Serum and incubated at 37° C. Twenty-four hours later, test compounds are added at a final concentration range from as high 10 uM to as low 64 pM depending on the activities of the tested compounds in serial dilutions at a final DMSO concentration of 0.1%. Cells were incubated for 72 hours at 37° C. in complete growth media after addition of the test compound. After 72 hours of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR2 using Luminescence protocol, and analyzed with Analyze5 software to generate $IC_{50}$ values. Representative compounds of this invention showed inhibition of tumor cell proliferation in this assay.

Activities in H 1975 cell lines: Examples 21, 24, 26, 28, 36, 59, 65, 70, 92, 93, 98, 107, 110, 1114, 115, 117, 118, 122-124, 126, 129, 135, 150, 160, 165, 183, 187, 194, 195, 199, 205, and 206 have $IC_{50}$ below 200 nM; Examples 1, 3, 4, 7, 12, 16, 17, 20, 22, 25, 27, 40, 45-47, 49, 50, 54-57, 60-64, 66-69, 72, 75, 77, 79, 81-83, 85-91, 94-97, 99-101, 104-106, 108, 109, 111-113, 116, 119, 121, 125, 127, 128, 132-134, 139-143, 149, 157-159, 161, 163, 164, 172, 176, 186, 188-190, 192, 196-198, 200-202, 204, 207, 208, and 209 have $IC_{50}$ in the range 200-1000 nM; Examples 2, 5, 6, 8, 9, 10, 11, 13-15, 19, 23, 29, 30-35, 37-39, 41-44, 48, 51-53, 58, 73, 74, 76, 78, 80, 84, 102, 103, 136-136, 144-148, 151-156, 162, 166-171, 173-175, 177-182, 184, 185, 191, 193, and 203 have $IC_{50}$ in the range of 1 uM-10 uM.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A compound of formula (I)

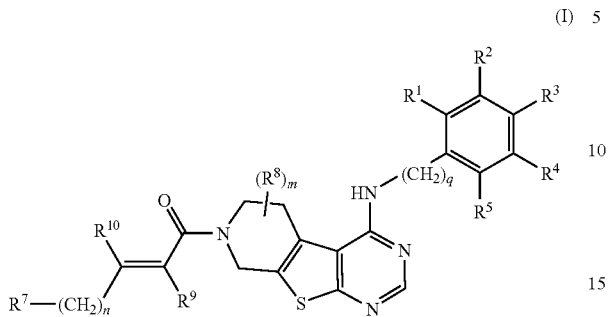

wherein
m is 0, 1, or 2;
n is 0, 1, 2, or 3;
q is 0 or 1;
$R^1$ represents H, $(C_1-C_4)$alkyl, or halo;
either
(a)
$R^2$ is selected from the group consisting of H, —CN, halo, $(C_1-C_4)$alkyl, —O$(C_1-C_4)$alkyl, $(C_2-C_4)$alkenyl, and $(C_2-C_4)$alkynyl; and
$R^3$ is selected from the group consisting of H, halo, —CN, $(C_1-C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1-C_4)$alkyl and halo; or
(b)
$R^2$ and $R^3$ are joined, and taken together with the carbon atoms to which they are attached, form a fused five- or six-membered saturated or unsaturated carbocycle, or form a fused heterocycle in which the combined $R^2$ and $R^3$ groups are represented by the formula

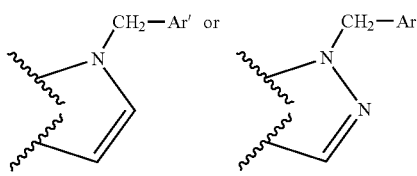

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;
$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;
$R^5$ represents H or halo;
when n is 0, $R^7$ is H;
when n is 1, 2 or 3, $R^7$ represents:
H;
hydroxyl;
—$NR^{12}R^{13}$ wherein
$R^{12}$ represents H or $(C_1-C_6)$alkyl which optionally bears 1 or 2 hydroxyl or mono- or di- $((C_1-C_4)$alkyl)amino groups; and $R^{13}$ represents H, $(C_1-C_6)$alkyl, or $(C_3-C_6)$cycloalkyl, said alkyl and cycloalkyl groups optionally bearing 1 or 2 hydroxyl or mono- or di- $((C_1-C_4)$alkyl) amino groups;

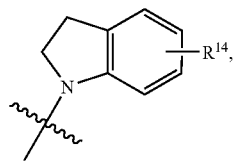

in which $R^{14}$ is hydroxyl, $(C_1-C_4)$alkyl, $(C_1-C_4)$alkoxy, or mono-or di- $((C_1-C_4)$alkyl)amino, each alkyl substituent in turn optionally bearing a hydroxyl substituent;

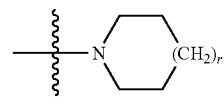

which optionally bears 1 or 2 hydroxyl, $(C_1-C_4)$alkyl, $(C_1-C_4)$alkoxy, or mono- or di- $((C_1-C_4)$alkyl)amino substituents, each alkyl substituent in turn optionally bearing a hydroxyl substituent; and
wherein r is 0, 1, or 2;

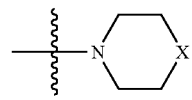

which optionally bears 1 or 2 $(C_1-C_4)$alkyl substituents, each alkyl substituent in turn optionally bearing a hydroxyl substituent; and wherein
X represents O, $S(O)_s$, or $NR^{15}$, in which s is 0, 1 or 2; and
$R^{15}$ represents $(C_1-C_4)$alkyl;

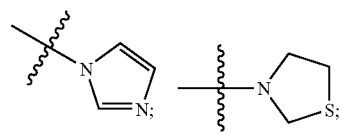

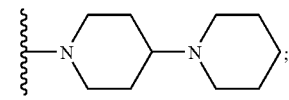

or
when n =2, $R^7$ and $R^9$ are optionally joined, and taken together with the carbon atoms to which they are attached and the intervening carbon atoms, form a ring of structure

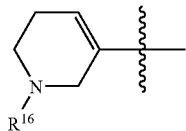

wherein $R^{16}$ represents $(C_1$-$C_4)$alkyl;

$R^8$ represents halo, hydroxyl, or $(C_1$-$C_4)$alkyl; and either (a)

$R^9$ represents H or —$CH_2$—Y, wherein Y is mono- or di-$((C_1$-$C_4)$alkyl)amino, or

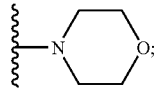

and $R^{10}$ represents H;

or (b)

$R^9$ and $R^{10}$ are taken together to form a bond, resulting in an acetylenic linkage;

or a pharmaceutically acceptable salt thereof.

2. The compound of claim 1, wherein m is 0, or a pharmaceutically acceptable salt thereof.

3. The compound of claim 2, wherein n is 1, or a pharmaceutically acceptable salt thereof 4. The compound of claim 3, wherein q is 0, or a pharmaceutically acceptable salt thereof 5. The compound of claim 1, wherein $R^1$ is hydrogen or fluoro;

$R^2$ is selected from the group consisting of H, —CN, halo, $(C_1$-$C_4)$alkyl, and $(C_2$-$C_4)$alkynyl;

$R^3$ is selected from the group consisting of H, halo, and *—$O(CH_2)_p$Ar, wherein Ar is phenyl, pyridyl, or pyrazinyl, and wherein Ar can optionally be substituted with 1 or 2 halogens, and wherein p is 0 or 1;

$R^4$ is selected from the group consisting of H, —CN, and halo;

$R^5$ is hydrogen;

$R^7$ is —$NR^{12}R^{13}$ wherein $R^{12}$ represents H or $(C_1$-$C_6)$alkyl; and $R^{13}$ represents H or $(C_1$-$C_6)$alkyl;

or a pharmaceutically acceptable salt thereof.

6. The compound of claim 1, wherein $R^1$ is H;

$R^2$ is selected from the group consisting of H, halo, and ethynyl;

$R^3$ is selected from the group consisting of H, halo, —CN, methyl, and *—$O(CH_2)_p$Ar, wherein Ar is phenyl, pyridyl, or pyrazinyl, and wherein Ar can alternatively be substituted with 0, 1 or 2 halogens, and wherein p is 0 or 1;

$R^4$ is selected from the group consisting of H, halo, and $(C_1$-$C_4)$alkyl;

$R^5$ is hydrogen; and $R^7$ is a mono- or di- $((C_1$-$C_4)$alkyl)amino group;

or a pharmaceutically acceptable salt thereof.

7. The compound of claim 6, wherein $R^2$ is ethynyl;

$R^3$ is selected from the group consisting of H, halo, and *—$O(CH_2)_p$Ar, wherein Ar is phenyl, pyridyl, or pyrazinyl, and wherein Ar can alternatively be substituted with 0, 1 or 2 halogens, and wherein p is 0 or 1; and $R^4$ is hydrogen;

or a pharmaceutically acceptable salt thereof.

8. The compound of claim 1, wherein $R^2$ is halo; and $R^3$ is selected from the group consisting of H, halo, and *—$O(CH_2)_p$Ar, wherein Ar is phenyl, pyridyl, or pyrazinyl, and wherein Ar can alternatively be substituted with 0, 1 or 2 halogens, and wherein p is 0 or 1;

or a pharmaceutically acceptable salt thereof.

9. The compound of claim 8, wherein $R^3$ is halo;

or a pharmaceutically acceptable salt thereof.

10. A compound selected from the group consisting of

N-[3-chloro-4-(pyridin-2-ylmethoxy)phenyl]-7-[(2E)-4-(diethylamino)but-2-enoyl]-5,6,7,8-tetrahydropyrido[4',3':4,5]thieno[2,3-d]pyrimidin-4-amine;

N-[3-chloro-4-(pyridin-2-ylmethoxy)phenyl]-7-[(2E)-4-(dimethylamino)but-2-enoyl]-5,6,7,8-tetrahydropyrido[4',3':4,5]thieno[2,3-d]pyrimidin-4-amine;

N-(3-chloro-4-fluorophenyl)-7-[(2E)-4-(dimethylamino)but-2-enoyl]-5,6,7,8-tetrahydropyrido[4',3':4,5]thieno[2,3-d]pyrimidin-4-amine;

N-(3-chloro-4-fluorophenyl)-7-[(2E)-4-(diethylamino)but-2-enoyl]-5,6,7,8-tetrahydropyrido[4',3':4,5]thieno[2,3-d]pyrimidin-4-amine;

7-[(2E)-4-(diethylamino)but-2-enoyl]-N-(3-ethynylphenyl)-5,6,7,8-tetrahydropyrido[4',3':4,5]thieno[2,3-d]pyrimidin-4-amine;

7-[(2E)-4-(dimethylamino)but-2-enoyl]-N-(3-ethynylphenyl)-5,6,7,8-tetrahydropyrido[4',3':4,5]thieno[2,3-d]pyrimidin-4-amine;

N-(3-chloro-4-fluorophenyl)-7- {(2E)-4-[isopropyl(methyl)amino]but-2-enoyl}-5,6,7,8-tetrahydropyrido[4',3':4,5]thieno[2,3-d]pyrimidin-4-amine;

N-(3-chloro-4-fluorophenyl)-7- {(2E)-4-[ethyl(isopropyl)amino]but-2-enoyl}-5,6,7,8 -tetrahydropyrido[4',3':4,5]thieno[2,3-d]pyrimidin-4-amine;

N-(3,4-dichlorophenyl)-7-[(2E)-4-(dimethylamino)but-2-enoyl]-5,6,7,8-tetrahydropyrido[4',3':4,5]thieno[2,3-d]pyrimidin-4-amine; and N-(3,4-dichlorophenyl)-7- {(2E)-4-[isopropyl(methyl)amino]but-2-enoyl}-5,6,7,8-tetrahydropyrido[4',3':4,5]thieno[2,3-d]pyrimidin-4-amine.

11. A process for preparing a compound as described in claim 1, comprising (i) reacting a compound of formula (7)

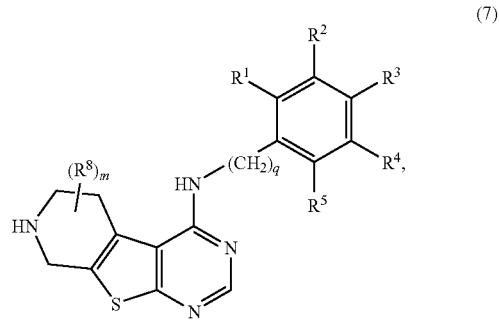

with a compound of formula (10)

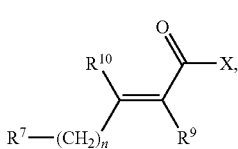

wherein X is hydroxy, chloro or bromo, or
(ii) reacting a compound of formula (9)

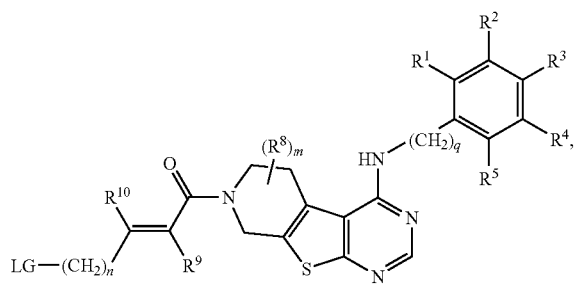

wherein LG is a leaving group, with a compound of formula $R^7$—H; or
(iii) reacting a compound of the formula (14):

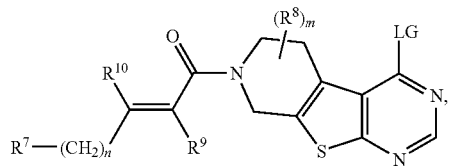

wherein LG is a leaving group,
with a compound of the formula (15):

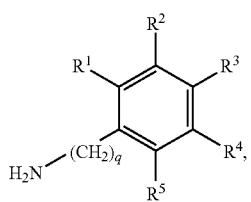

wherein LG is a leaving group,
under conditions such that a compound as described in claim 1 is prepared.

12. A pharmaceutical composition comprising a compound as defined in claim 1, together with a pharmaceutically acceptable carrier.

13. The pharmaceutical composition of claim 12, in a form suitable for intravenous administration.

14. A process for preparing a pharmaceutical composition, comprising combining at least one compound as defined in claim 1 with at least one pharmaceutically acceptable carrier, and bringing the resulting combination into a suitable administration form.

15. A compound of formula (7)

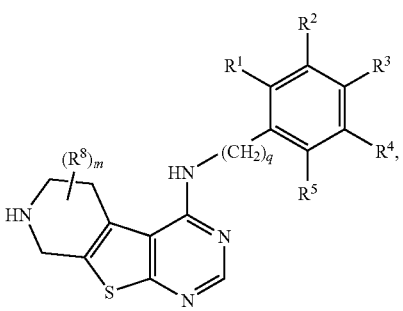

wherein m is 0, 1, or 2;

q is 0 or 1;

$R^1$ represents H, $(C_1-C_4)$alkyl, or halo;

either (a)

$R^2$ is selected from the group consisting of H, —CN, halo, $(C_1-C_4)$alkyl, —O$(C_1-C_4)$alkyl, $(C_2-C_4)$alkenyl, and $(C_2-C_4)$alkynyl;

$R^3$ is selected from the group consisting of H, halo, —CN, $(C_1-C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1-C_4)$alkyl and halo; or (b)

$R^2$ and $R^3$ are joined, and taken together with the carbon atoms to which they are attached, form a fused five- or six-membered saturated or unsaturated carbocycle, or form a fused heterocycle in which the combined $R^2$ and $R^3$ groups are represented by the formula

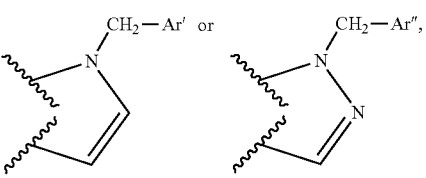

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;

$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;

$R^5$ represents H or halo; and $R^8$ represents halo, hydroxyl, or $(C_1-C_4)$alkyl.

16. A compound of formula (9)

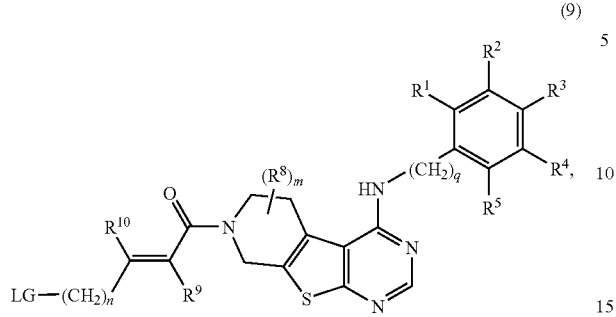

wherein
m is 0, 1, or 2;
n is 0, 1, 2, or 3;
q is 0 or 1;
$R^1$ represents H, $(C_1-C_4)$alkyl, or halo;
either
(a)
$R^2$ is selected from the group consisting of H, —CN, halo, $(C_1-C_4)$alkyl, —O$(C_1-C_4)$alkyl, $(C_2-C_4)$alkenyl, and $(C_2-C_4)$alkynyl ; and
$R^3$ is selected from the group consisting of H, halo, —CN, $(C_1-C_4)$alkyl, ethynyl, propargyl, and *—O$(CH_2)_p$Ar, wherein p is 0, 1, or 2, and Ar represents phenyl, pyridyl, thiazolyl, thiophenyl, or pyrazinyl, and wherein Ar optionally bears 1 or 2 substituents selected from the group consisting of $(C_1-C_4)$alkyl and halo; or
(b)
$R^2$ and $R^3$ are joined, and taken together with the carbon atoms to which they are attached, form a fused five- or six-membered saturated or unsaturated carbocycle, or form a fused heterocycle in which the combined $R^2$ and $R^3$ groups are represented by the formula

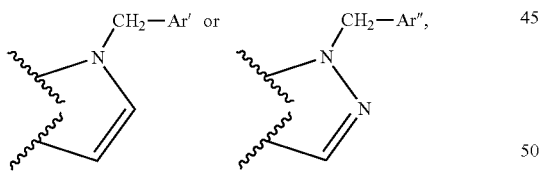

wherein Ar' and Ar" each represents phenyl, pyridyl, thiazolyl, thienyl, or pyrazinyl and wherein Ar' and Ar" each optionally bears 1 or 2 substituents selected from the group consisting of $(C_1-C_4)$alkyl and halo;
$R^4$ is selected from the group consisting of H, —CN, $(C_1-C_4)$alkyl, —O$(C_1-C_4)$alkyl, halo, $(C_2-C_4)$alkenyl, and $(C_2-C_4)$alkynyl;
$R^5$ represents H or halo;
$R^8$ represents halo, hydroxyl, or $(C_1-C_4)$alkyl;
either
(a)
$R^9$ represents H or —CH$_2$—Y, wherein Y is mono- or di- $((C_1-C_4)$alkyl)amino, or

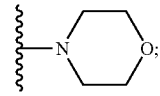

and
$R^{10}$ represents H;
or
(b)
$R^9$ and $R^{10}$ are taken together to form a bond, resulting in an acetylenic linkage;
and
LG is a leaving group.

17. A compound of formula (14):

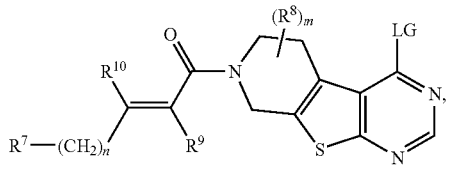

wherein
m is 0, 1, or 2;
n is 0, 1, 2, or 3; q is 0 or 1;
when n is 0, $R^7$ is H;
when n is 1, 2 or 3, $R^7$ represents:
H;
hydroxyl;
—NR$^{12}$R$^{13}$ wherein
$R^{12}$ represents H or $(C_1-C_6)$alkyl which optionally bears 1 or 2 hydroxyl or mono- or di- $((C_1-C_4)$alkyl)amino groups; and
$R^{13}$ represents H, $(C_1-C_6)$alkyl, or $(C_3-C_6)$cycloalkyl, said alkyl and cycloalkyl groups optionally bearing 1 or 2 hydroxyl or mono- or di- $((C_1-C_4)$alkyl)amino groups;

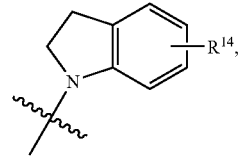

in which $R^{14}$ is hydroxyl, $(C_1-C_4)$alkyl, $(C_1-C_4)$alkoxy, or mono- or di- $((C_1-C_4)$alkyl)amino, each alkyl substituent in turn optionally bearing a hydroxyl substituent;

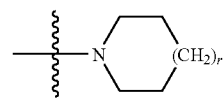

which optionally bears 1 or 2 hydroxyl, $(C_1-C_4)$alkyl, $(C_1-C_4)$alkoxy, or mono- or di- $((C_1-C_4)$alkyl)amino substituents, each alkyl substituent in turn optionally bearing a hydroxyl substituent; and wherein r is 0, 1, or 2;

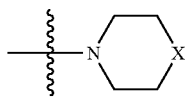

which optionally bears 1 or 2 $(C_1\text{-}C_4)$alkyl substituents, each alkyl substituent in turn optionally bearing a hydroxyl substituent; and wherein X represents O, S(O)s, or $NR^{15}$, in which s is 0, 1 or 2; and $R^{15}$ represents $(C_1\text{-}C_4)$alkyl;

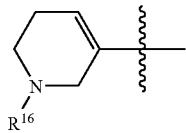

or when n=2, $R^7$ and $R^9$ are optionally joined, and taken together with the carbon atoms to which they are attached and the intervening carbon atoms, form a ring of structure wherein $R^{16}$ represents $(C_1\text{-}C_4)$alkyl;

$R^8$ represents halo, hydroxyl, or $(C_1\text{-}C_4)$alkyl;

either (a) $R^9$ represents H or —CH$_2$—Y, wherein Y is mono- or di-$((C_1\text{-}C_4)$alkyl)amino, or

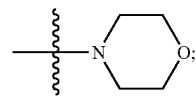

and $R^{10}$ represents H;

or (b) $R^9$ and $R^{10}$ are taken together to form a bond, resulting in an acetylenic linkage; and LG is a leaving group.

18. A method of treating a cancer selected from non-small cell lung cancer, gastric cancer, and epidermoid cancer in a patient in need of such treatment, comprising administering to the patient an effective amount of a compound as defined in claim 1.

19. The method of claim 18, wherein the cancer is non-small cell lung cancer.

20. The method of claim 18, wherein the cancer is gastric cancer.

21. The method of claim 18, wherein the cancer is epidermoid cancer.

* * * * *